United States Patent
Baxter, III et al.

(10) Patent No.: US 10,898,197 B2
(45) Date of Patent: Jan. 26, 2021

(54) RELEASABLE COUPLING FEATURES FOR PROXIMAL PORTIONS OF LINEAR SURGICAL STAPLER

(71) Applicant: ETHICON LLC, Guaynabo, PR (US)

(72) Inventors: Chester O. Baxter, III, Loveland, OH (US); Jason Jones, Cincinnati, OH (US); Michael J. Stokes, Cincinnati, OH (US); Anil K. Nalagatla, Mason, OH (US); Hector Chow, Montgomery, OH (US); Matthew S. Corbin, Loveland, OH (US); Omar J. Vakharia, Cincinnati, OH (US); Wells D. Haberstich, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 353 days.

(21) Appl. No.: 15/889,376

(22) Filed: Feb. 6, 2018

(65) Prior Publication Data

US 2019/0239883 A1 Aug. 8, 2019

(51) Int. Cl.
*A61B 17/115* (2006.01)
*A61B 17/072* (2006.01)
(Continued)

(52) U.S. Cl.
CPC ...... *A61B 17/115* (2013.01); *A61B 17/07207* (2013.01); *A61B 17/1114* (2013.01);
(Continued)

(58) Field of Classification Search
CPC ............ A61B 17/115; A61B 17/07207; A61B 17/1114; A61B 17/2833; A61B 17/2841; A61B 2017/07278; A61B 2017/07285
(Continued)

(56) References Cited

U.S. PATENT DOCUMENTS 960,300 A 6/1910 Fischer
3,078,465 A 2/1963 Bobrov
(Continued)

FOREIGN PATENT DOCUMENTS

DE 38 19 292 C1 7/1989
EP 0033548 B1 5/1986
(Continued)

OTHER PUBLICATIONS

European Search Report, Extended, and Written Opinion dated May 13, 2019 for Application No. EP 19155448.4, 8 pgs.
(Continued)

*Primary Examiner* — Michelle Lopez
(74) *Attorney, Agent, or Firm* — Frost Brown Todd LLC

(57) ABSTRACT

A surgical stapler includes an anvil half having an anvil channel member and a cartridge half having a cartridge channel member. A latching lever is coupled to the cartridge channel member and is pivotable between a closed position in which the lever fixes the anvil channel member relative to the cartridge channel member, and an open position in which the lever permits relative movement between the channel members. A locking member coupled to a proximal portion of the cartridge half is movable between a locked position when the lever is in the closed position and an unlocked position when the lever is in the open position. In the locked position the locking member captures the projection and locks the anvil half proximal portion to the cartridge half proximal portion. In the unlocked position the locking member releases the projection and permits separation of the proximal portions.

20 Claims, 30 Drawing Sheets

(51) Int. Cl.
*A61B 17/28* (2006.01)
*A61B 17/11* (2006.01)
*A61B 17/3205* (2006.01)
*A61B 17/00* (2006.01)

(52) U.S. Cl.
CPC ...... *A61B 17/2833* (2013.01); *A61B 17/2841* (2013.01); *A61B 17/3205* (2013.01); *A61B 2017/00477* (2013.01); *A61B 2017/00557* (2013.01); *A61B 2017/00876* (2013.01); *A61B 2017/07278* (2013.01); *A61B 2017/07285* (2013.01)

(58) Field of Classification Search
USPC .................................................. 227/176.1
See application file for complete search history.

(56) References Cited

U.S. PATENT DOCUMENTS

| | | |
|---|---|---|
| 3,079,606 A | 3/1963 | Bobrov et al. |
| 3,315,863 A | 4/1967 | O'Dea |
| 3,317,105 A | 5/1967 | Astafjev et al. |
| 3,490,675 A | 1/1970 | Green et al. |
| 4,111,206 A | 9/1978 | Vishnevsky et al. |
| 4,241,861 A | 12/1980 | Fleischer |
| 4,290,542 A | 9/1981 | Fedotov et al. |
| D272,851 S | 2/1984 | Green et al. |
| D272,852 S | 2/1984 | Green et al. |
| 4,429,695 A | 2/1984 | Green |
| 4,520,817 A | 6/1985 | Green |
| 4,596,351 A | 6/1986 | Fedotov et al. |
| 4,605,001 A | 8/1986 | Rothfuss et al. |
| D285,836 S | 9/1986 | Hunt et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A * | 1/1987 | Chow .............. A61B 17/07207 227/176.1 |
| 4,869,415 A | 9/1989 | Fox |
| 4,892,244 A | 1/1990 | Fox et al. |
| 4,955,898 A | 9/1990 | Matsutani et al. |
| 5,065,929 A | 11/1991 | Schulze et al. |
| 5,083,695 A | 1/1992 | Foslien et al. |
| 5,129,570 A | 7/1992 | Schulze et al. |
| 5,141,144 A | 8/1992 | Foslien et al. |
| 5,156,614 A | 10/1992 | Green et al. |
| 5,173,133 A | 12/1992 | Morin et al. |
| 5,221,036 A | 6/1993 | Takase |
| 5,417,361 A | 5/1995 | Williamson, IV |
| 5,445,304 A | 8/1995 | Plyley et al. |
| 5,452,837 A | 9/1995 | Williamson, IV et al. |
| 5,465,896 A | 11/1995 | Allen et al. |
| 5,489,058 A | 2/1996 | Plyley et al. |
| 5,505,363 A | 4/1996 | Green et al. |
| 5,535,935 A | 7/1996 | Vidal et al. |
| 5,542,594 A | 8/1996 | McKean et al. |
| 5,562,241 A | 10/1996 | Knodel et al. |
| 5,586,711 A | 12/1996 | Plyley et al. |
| 5,636,779 A | 6/1997 | Palmer |
| 5,651,491 A | 7/1997 | Heaton et al. |
| 5,653,373 A | 8/1997 | Green et al. |
| 5,655,698 A | 8/1997 | Yoon |
| 5,657,921 A | 8/1997 | Young et al. |
| 5,673,842 A | 10/1997 | Bittner et al. |
| 5,680,983 A | 10/1997 | Plyley et al. |
| 5,718,359 A | 2/1998 | Palmer et al. |
| 5,785,232 A | 7/1998 | Vidal et al. |
| 5,816,471 A | 10/1998 | Plyley et al. |
| 5,871,135 A | 2/1999 | Williamson, IV et al. |
| 5,908,427 A | 6/1999 | McKean et al. |
| 5,988,479 A | 11/1999 | Palmer |
| 6,045,560 A | 4/2000 | McKean et al. |
| 6,131,789 A | 10/2000 | Schulze et al. |
| 6,155,473 A | 12/2000 | Tompkins et al. |
| 6,206,903 B1 | 3/2001 | Ramans |
| 7,032,799 B2 | 4/2006 | Viola et al. |
| 7,055,730 B2 | 6/2006 | Ehrenfels et al. |
| 7,121,446 B2 | 10/2006 | Arad et al. |
| 7,140,527 B2 | 11/2006 | Ehrenfels et al. |
| 7,188,758 B2 | 3/2007 | Viola et al. |
| 7,207,471 B2 | 4/2007 | Heinrich et al. |
| 7,210,609 B2 | 5/2007 | Leiboff et al. |
| 7,238,195 B2 | 7/2007 | Viola |
| 7,278,563 B1 | 10/2007 | Green |
| 7,293,685 B2 | 11/2007 | Ehrenfels et al. |
| 7,326,232 B2 | 2/2008 | Viola et al. |
| 7,334,717 B2 | 2/2008 | Rethy et al. |
| 7,407,078 B2 | 8/2008 | Shelton, IV et al. |
| 7,419,081 B2 | 9/2008 | Ehrenfels et al. |
| 7,422,139 B2 | 9/2008 | Shelton, IV et al. |
| 7,431,730 B2 | 10/2008 | Viola |
| 7,472,815 B2 | 1/2009 | Shelton, IV et al. |
| 7,472,816 B2 | 1/2009 | Holsten et al. |
| 7,490,749 B2 | 2/2009 | Schall et al. |
| 7,543,729 B2 | 6/2009 | Ivanko |
| 7,568,604 B2 | 8/2009 | Ehrenfels et al. |
| 7,571,845 B2 | 8/2009 | Viola |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,410 B2 | 12/2009 | Marczyk |
| 7,641,091 B2 | 1/2010 | Olson et al. |
| 7,665,647 B2 | 2/2010 | Shelton, IV et al. |
| 7,717,312 B2 | 5/2010 | Beetel |
| 7,721,933 B2 | 5/2010 | Ehrenfels et al. |
| 7,722,610 B2 | 5/2010 | Viola et al. |
| 7,740,160 B2 | 6/2010 | Viola |
| 7,744,628 B2 | 6/2010 | Viola |
| 7,766,209 B2 | 8/2010 | Baxter, III et al. |
| 7,810,691 B2 | 10/2010 | Boyden et al. |
| 7,815,092 B2 | 10/2010 | Whitman et al. |
| 7,828,189 B2 | 11/2010 | Holsten et al. |
| 7,837,081 B2 | 11/2010 | Holsten et al. |
| 7,866,528 B2 | 1/2011 | Olson et al. |
| 7,905,381 B2 | 3/2011 | Baxter, III et al. |
| 7,931,182 B2 | 4/2011 | Boyden et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,997,469 B2 | 8/2011 | Olson et al. |
| 8,006,888 B2 | 8/2011 | Viola |
| 8,028,884 B2 | 10/2011 | Sniffin et al. |
| 8,070,035 B2 | 12/2011 | Holsten et al. |
| 8,074,861 B2 | 12/2011 | Ehrenfels et al. |
| 8,091,754 B2 | 1/2012 | Ehrenfels et al. |
| 8,113,407 B2 | 2/2012 | Holsten et al. |
| 8,127,975 B2 | 3/2012 | Olson et al. |
| 8,152,041 B2 | 4/2012 | Kostrzewski |
| 8,157,153 B2 | 4/2012 | Shelton, IV et al. |
| 8,231,040 B2 | 7/2012 | Zemlok et al. |
| 8,245,901 B2 | 8/2012 | Stopek |
| 8,256,655 B2 | 9/2012 | Sniffin et al. |
| 8,257,634 B2 | 9/2012 | Scirica |
| 8,267,300 B2 | 9/2012 | Boudreaux |
| 8,272,552 B2 | 9/2012 | Holsten et al. |
| 8,292,146 B2 | 10/2012 | Holsten et al. |
| 8,292,148 B2 | 10/2012 | Viola |
| 8,308,043 B2 | 11/2012 | Bindra et al. |
| 8,336,753 B2 | 12/2012 | Olson et al. |
| 8,348,129 B2 | 1/2013 | Bedi et al. |
| 8,418,907 B2 | 4/2013 | Johnson et al. |
| 8,464,922 B2 | 6/2013 | Marczyk |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,505,801 B2 | 8/2013 | Ehrenfels et al. |
| 8,544,712 B2 | 10/2013 | Jankowski |
| 8,579,178 B2 | 11/2013 | Holsten et al. |
| 8,636,193 B2 | 1/2014 | Whitman et al. |
| 8,636,939 B2 | 1/2014 | Czernik et al. |
| 8,679,156 B2 | 3/2014 | Smith et al. |
| 8,708,210 B2 | 4/2014 | Zemlok et al. |
| 8,728,118 B2 | 5/2014 | Hinman et al. |

(56) References Cited

U.S. PATENT DOCUMENTS

| | | |
|---|---|---|
| 8,789,740 B2 | 7/2014 | Baxter, III et al. |
| 8,905,287 B2 | 12/2014 | Racenet et al. |
| 8,915,930 B2 | 12/2014 | Huitema et al. |
| 9,016,541 B2 | 4/2015 | Viola et al. |
| 9,119,617 B2 | 9/2015 | Souls et al. |
| 9,364,219 B2 | 6/2016 | Olson et al. |
| 9,402,629 B2 | 8/2016 | Ehrenfels et al. |
| 9,439,649 B2 | 9/2016 | Shelton, IV et al. |
| 9,451,959 B2 | 9/2016 | Patankar et al. |
| 9,474,525 B2 | 10/2016 | Smith et al. |
| 9,498,213 B2 | 11/2016 | Marczyk et al. |
| 9,561,030 B2 | 2/2017 | Zhang et al. |
| 9,629,812 B2 | 4/2017 | Widenhouse et al. |
| 9,636,113 B2 | 5/2017 | Wenchell |
| 9,636,128 B2 | 5/2017 | Zemlok et al. |
| 9,681,873 B2 | 6/2017 | Smith et al. |
| 9,693,775 B2 | 7/2017 | Agarwal et al. |
| 9,750,502 B2 | 9/2017 | Scirica et al. |
| 9,867,616 B2 | 1/2018 | Marczyk |
| 2006/0180633 A1 | 8/2006 | Emmons |
| 2007/0119901 A1 | 5/2007 | Ehrenfels et al. |
| 2007/0145096 A1 | 6/2007 | Viola et al. |
| 2009/0255974 A1 | 10/2009 | Viola |
| 2009/0308907 A1 | 12/2009 | Nalagatla et al. |
| 2010/0133317 A1 | 6/2010 | Shelton, IV et al. |
| 2011/0290856 A1 | 12/2011 | Shelton, IV et al. |
| 2012/0046689 A1 | 2/2012 | Criscuolo et al. |
| 2012/0286022 A1 | 11/2012 | Olson et al. |
| 2013/0186935 A1 | 7/2013 | Edoga et al. |
| 2013/0190732 A1 | 7/2013 | Slisz et al. |
| 2014/0103091 A1 | 4/2014 | Whitman et al. |
| 2015/0327855 A1 | 11/2015 | Katre et al. |
| 2016/0157890 A1 | 6/2016 | Drake et al. |
| 2016/0262756 A1 | 9/2016 | Patankar et al. |
| 2018/0055512 A1 | 3/2018 | Stokes et al. |

FOREIGN PATENT DOCUMENTS

| | | |
|---|---|---|
| EP | 0178940 B1 | 1/1991 |
| EP | 0669104 A1 | 8/1995 |
| EP | 0770355 A1 | 5/1997 |
| EP | 1382303 B1 | 6/2006 |
| EP | 1702567 A2 | 9/2006 |
| EP | 1728475 A2 | 12/2006 |
| EP | 1977701 B1 | 12/2011 |
| EP | 2452636 A2 | 5/2012 |
| EP | 2305137 B1 | 12/2012 |
| EP | 2308390 B1 | 12/2012 |
| EP | 1693007 B1 | 10/2013 |
| EP | 1862129 B1 | 4/2014 |
| EP | 2550920 B1 | 1/2015 |
| EP | 2532313 B1 | 4/2016 |
| EP | 2532312 B1 | 12/2016 |
| EP | 3155988 A1 | 4/2017 |
| GB | 927936 A | 6/1963 |
| JP | 2001-502575 A | 2/2001 |
| JP | 2007-000657 A | 1/2007 |
| SU | 599799 A1 | 4/1978 |
| WO | WO 1999/045849 A1 | 9/1999 |
| WO | WO 2002/030297 A2 | 4/2002 |
| WO | WO 2003/030742 A2 | 4/2003 |
| WO | WO 2003/094743 A1 | 11/2003 |
| WO | WO 2003/094745 A1 | 11/2003 |
| WO | WO 2003/094746 A1 | 11/2003 |
| WO | WO 2003/094747 A1 | 11/2003 |
| WO | WO 2003/079909 A3 | 3/2004 |
| WO | WO 2004/032763 A2 | 4/2004 |
| WO | WO 2007/127283 A2 | 11/2007 |
| WO | WO 2013/109445 A2 | 7/2013 |
| WO | WO 2015/065482 A1 | 5/2015 |
| WO | WO 2015/065485 A1 | 5/2015 |

OTHER PUBLICATIONS

International Search Report and Written Opinion dated May 10, 2019 for Application No. PCT/IB2019/050359, 15 pgs.
U.S. Appl. No. 15/889,363, filed Feb. 6, 2018.
U.S. Appl. No. 15/889,370, filed Feb. 6, 2018.
U.S. Appl. No. 15/889,374, filed Feb. 6, 2018.
U.S. Appl. No. 15/889,388, filed Feb. 6, 2018.
U.S. Appl. No. 15/889,390, filed Feb. 6, 2018.

* cited by examiner

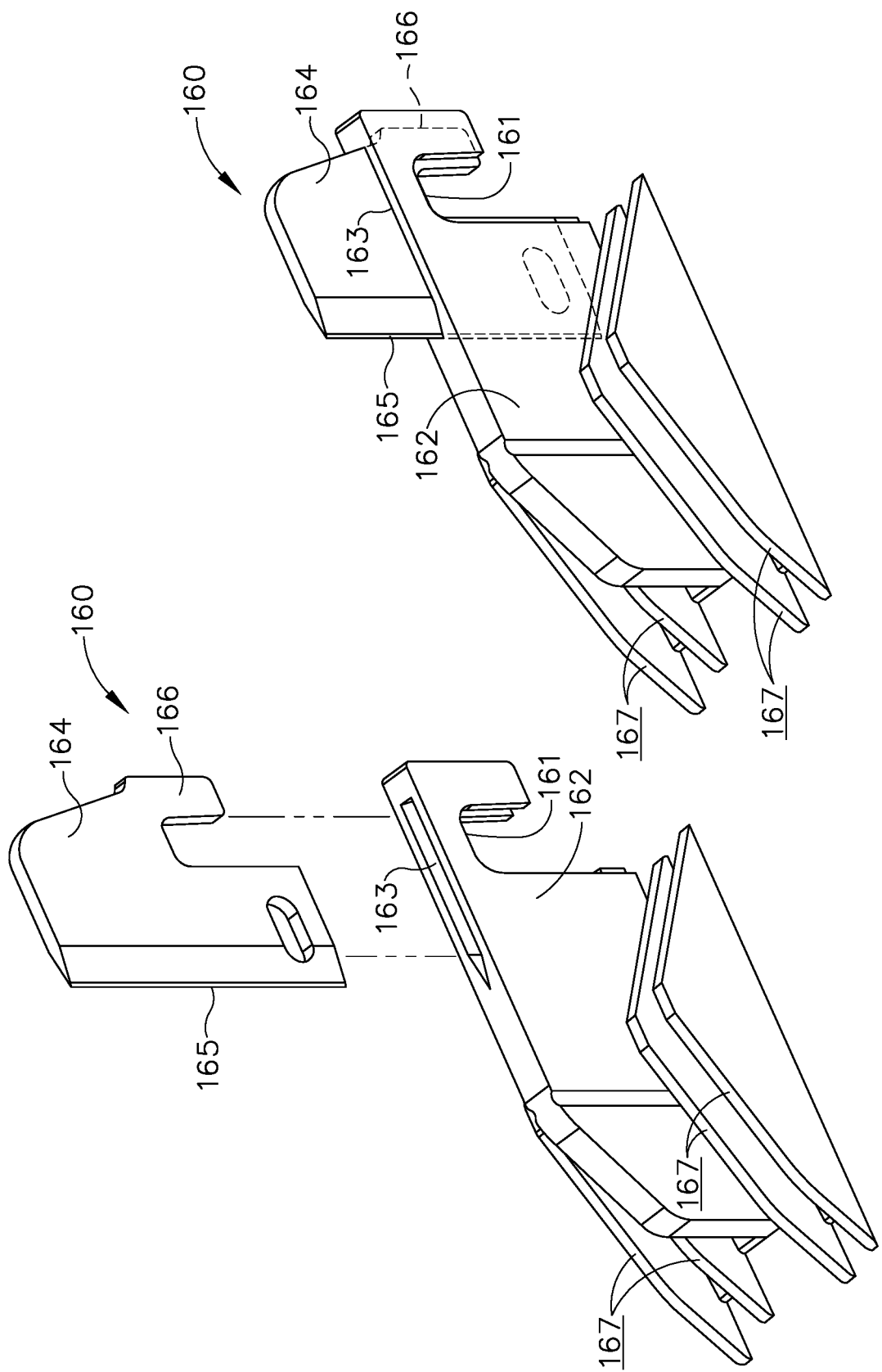

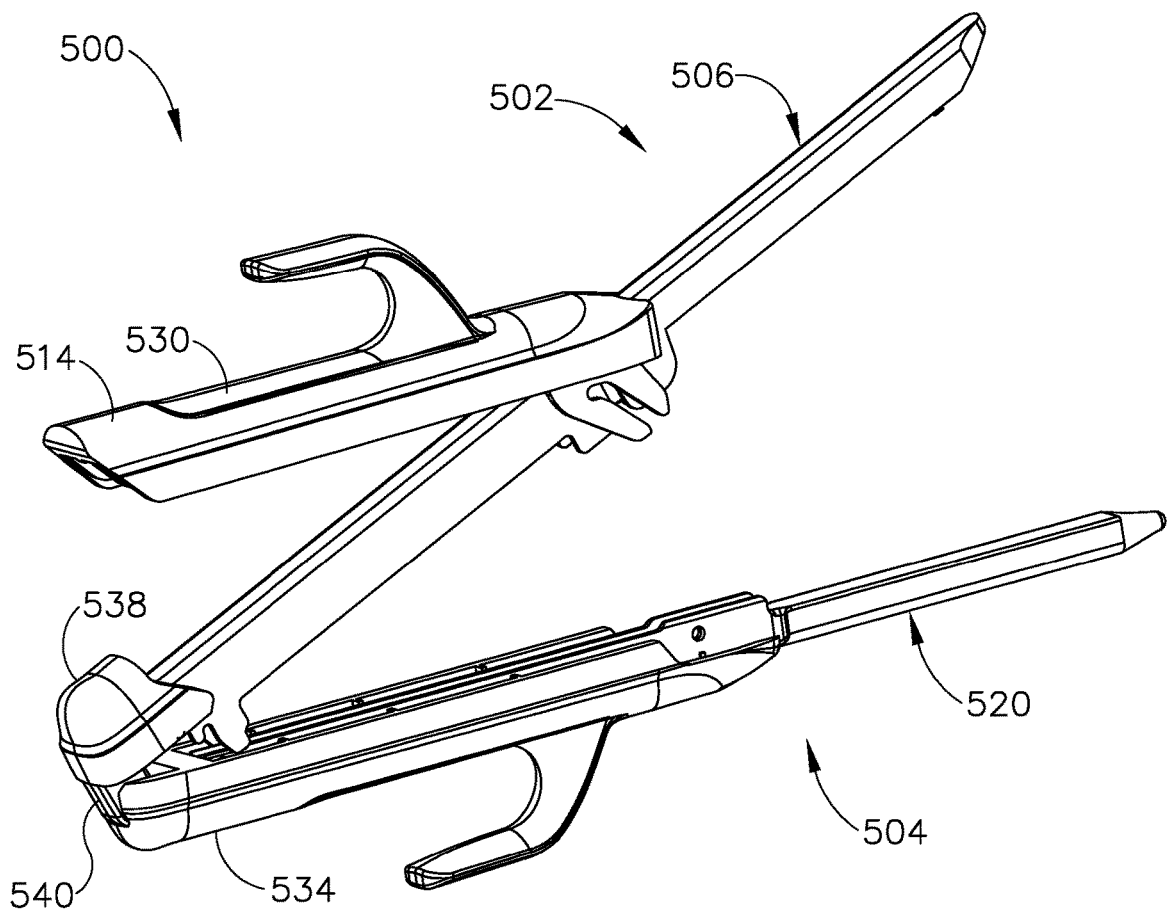
Fig.16C
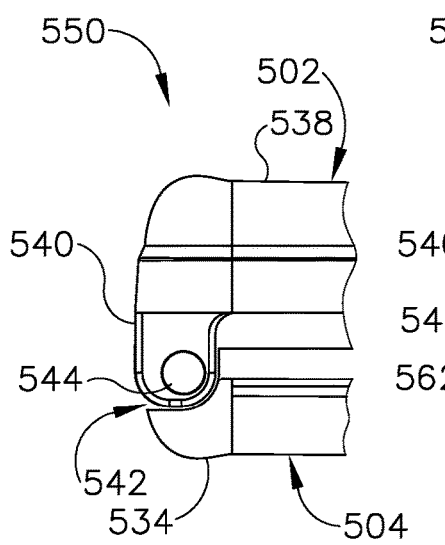 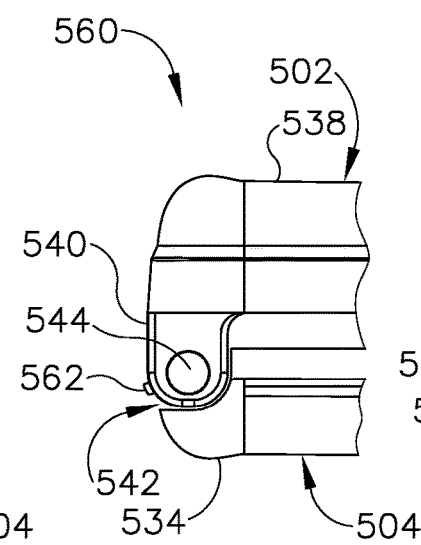 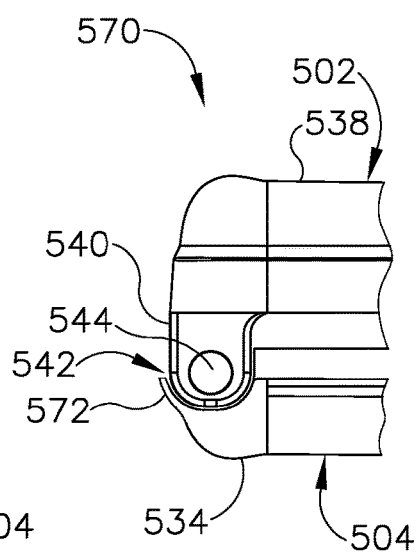
Fig.17   Fig.18   Fig.19

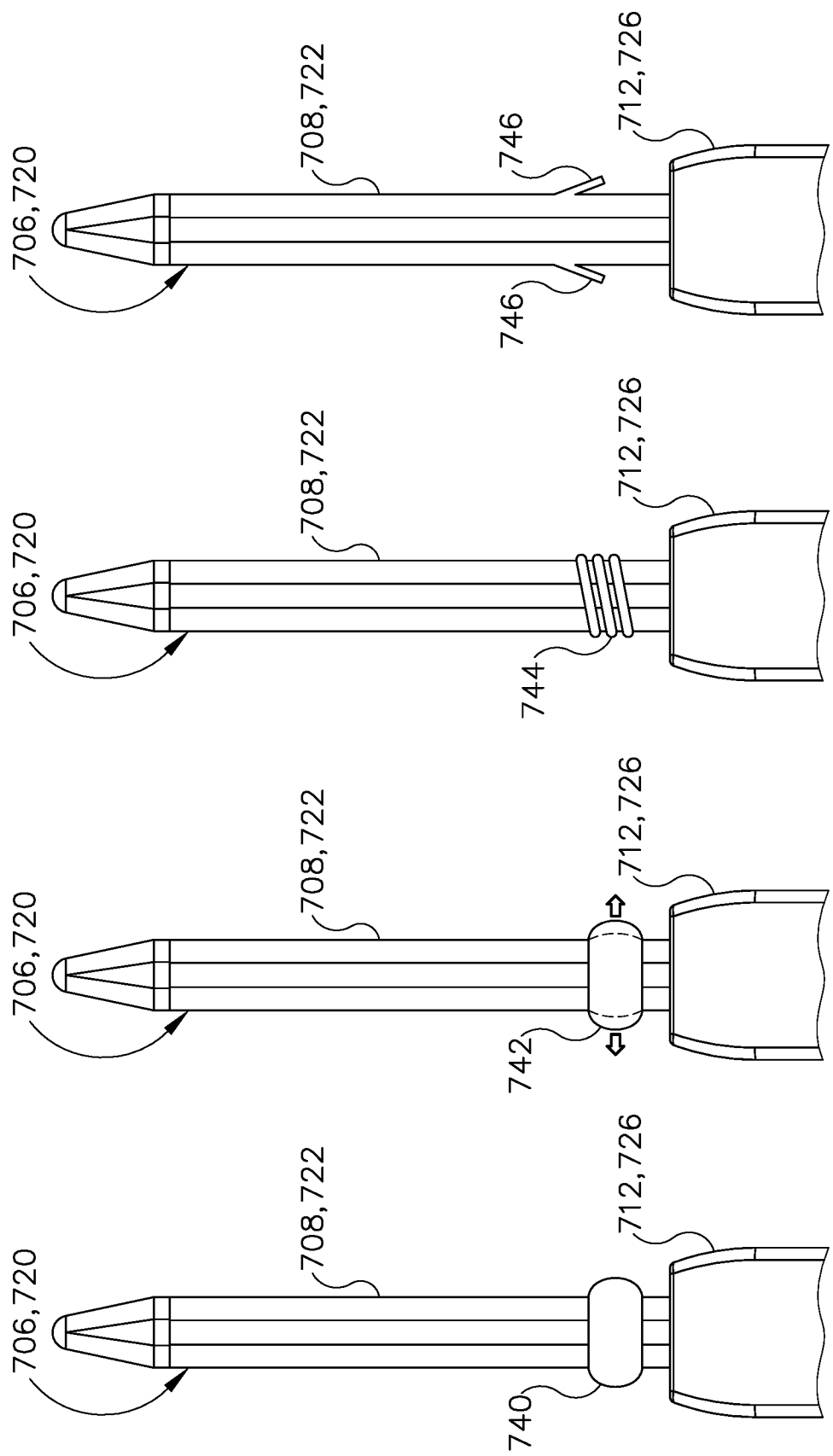

RELEASABLE COUPLING FEATURES FOR PROXIMAL PORTIONS OF LINEAR SURGICAL STAPLER

BACKGROUND

In some surgical operations, such as a gastrointestinal anastomosis, it may be desirable to clamp down on one or more layers of tissue, cut through the clamped layers of tissue and drive staples through the layers of tissue to substantially seal the severed layers of tissue together near the severed ends of the tissue layers. One such instrument that may be used in such operations is a linear cutting stapler. A linear cutting stapler generally includes a first jaw, a second jaw, a lever for clamping the first jaw relative to the second jaw, an anvil associated with either the first jaw or the second jaw, a staple cartridge associated with the jaw opposing the staple anvil, and a firing assembly movable relative to the rest of the linear cutting stapler. Typically, the first jaw and the second jaw may pivot relative each other in order to grasp tissue between the jaws. Staples are arranged in the staple cartridge such that a portion of firing assembly may actuate through the staple cartridge to drive staples out of staple cartridge, through tissue, and against anvil while also severing tissue captured between the staple cartridge and the staple anvil.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 7 depicts an exploded view of a staple sled assembly of the surgical stapling instrument of FIG. 1;

FIG. 8 depicts a perspective view of the staple sled assembly of FIG. 7;

FIG. 16C depicts a perspective view of the surgical stapling instrument of FIG. 15, showing the proximal ends of the first and second instrument halves coupled together;

FIG. 17 depicts a side elevational view of a proximal end of a first variation of the surgical stapling instrument of FIG. 15, showing the instrument with a first exemplary feature configured to facilitate separation of the magnetic alignment members of the instrument halves;

FIG. 18 depicts a side elevational view of the proximal end of a second variation of the surgical stapling instrument of FIG. 15, showing the instrument with a second exemplary feature configured to facilitate separation of the magnetic alignment members of the instrument halves;

FIG. 19 depicts a side elevational view of a third variation of the proximal end of the surgical stapling instrument of FIG. 15, showing the instrument with a third exemplary feature configured to facilitate separation of the magnetic alignment members of the instrument halves;

FIG. 23 depicts a bottom elevational view of a distal portion of a half of the surgical stapling instrument of FIG. 22, showing the instrument half with the respective tissue retaining feature according to a first exemplary configuration;

FIG. 24 depicts a bottom elevational view of a distal portion of a half of the surgical stapling instrument of FIG. 22, showing the instrument half with the respective tissue retaining feature according to a second exemplary configuration;

FIG. 25 depicts a bottom elevational view of a distal portion of a half of the surgical stapling instrument of FIG. 22, showing the instrument half with the respective tissue retaining feature according to a third exemplary configuration;

FIG. 26 depicts a bottom elevational view of a distal portion of a half of the surgical stapling instrument of FIG. 22, showing the instrument half with the respective tissue retaining feature according to a fourth exemplary configuration;

Figure 1:
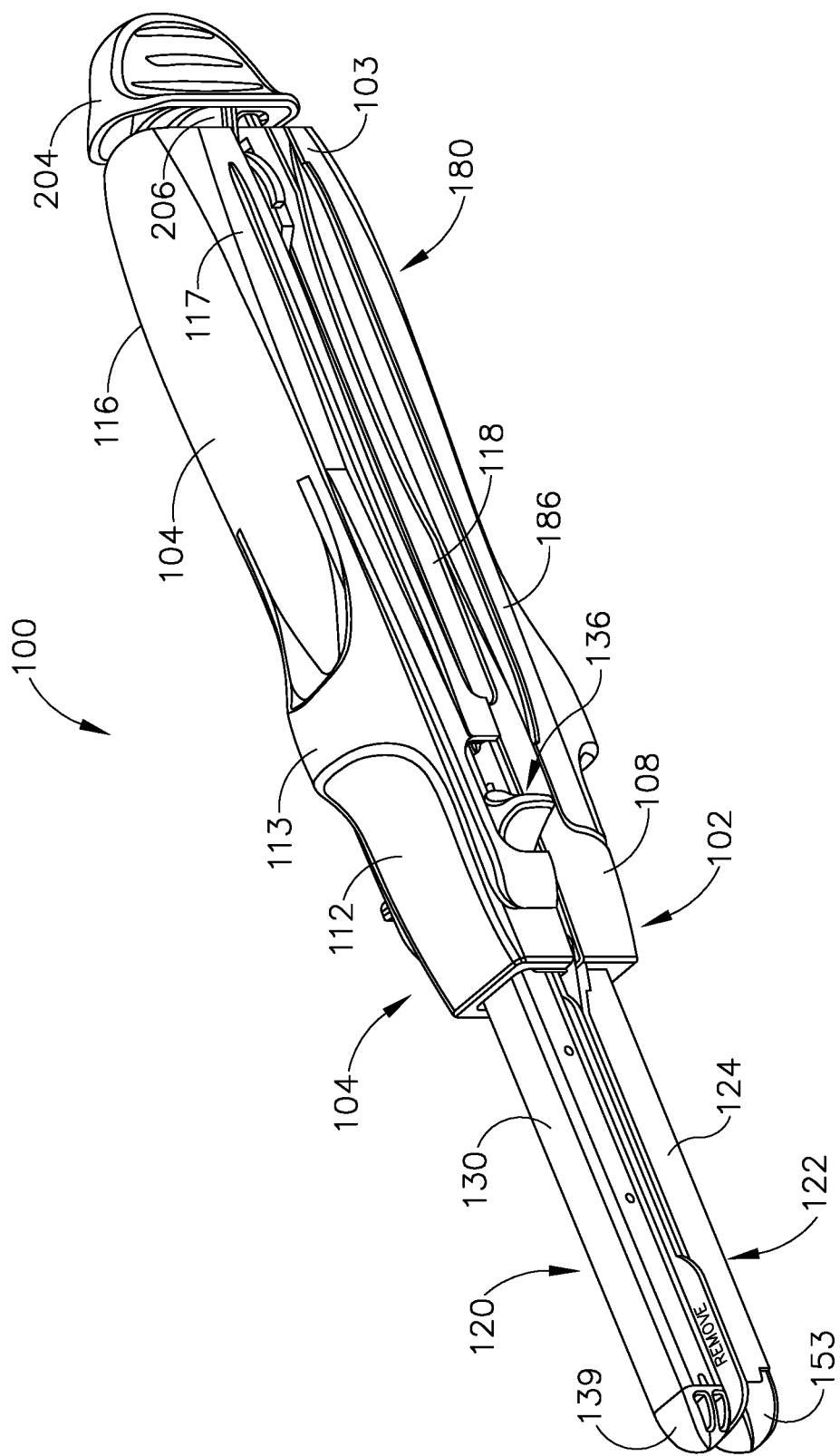
FIG. 1 depicts a perspective view of an exemplary surgical stapling instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal,"

"distal," "upper," and "lower" are thus relative terms and not intended to unnecessarily limit the invention described herein.

I. Exemplary Linear Cutting Stapler

A. Overview of Features of Linear Cutting Stapler

FIG. 1 depicts an exemplary surgical linear cutting stapler (100) that may be used for any suitable procedure, such as a gastrointestinal anastomosis. Linear cutting stapler (100) includes a first portion (102) having a staple cartridge channel (122), a second portion (104) having an anvil channel (130), a staple cartridge assembly (150) that may selectively couple with cartridge channel (122) of first portion (102), and a firing assembly (200). As will be described in greater detail below, first portion (102) and staple cartridge assembly (150) may pivotably couple with second portion (104) to form an end effector (120) capable of clamping, severing, and stapling tissue captured between opposing halves of end effector (120).

As best seen in FIGS. 3-6, firing assembly (200) includes an actuating beam (202), a staple sled assembly (160) housed within staple cartridge assembly (150), an actuator (204) (also referred to as a "firing knob"), and a pivot arm (206). Actuating beam (202) extends from a distal end (201) to a proximal end (203). Actuating beam (202) is slidably housed within first portion (102). Pivot arm (206) connects actuator (204) with distal end (201) of actuating beam (202). Actuator (204) and pivot arm (206) may pivot from a proximal position (shown in FIG. 1) to either lateral side of actuating beam (202) (shown in FIG. 11A), thereby enabling an operator to actuate firing assembly (200) from either a first side (116) or a second side (117) of instrument (100) when portions (102, 104) are properly coupled and end effector (120) is in the fully closed position. It should be understood when instrument (100) is properly coupled and end effector (120) is in the fully closed position, first portion (102) and second portion (104) define a slot (118) dimensioned to accommodate translation of actuator (204). In the current example, as will be described in greater detail below, actuating beam (202) is operable to couple with staple sled assembly (160) when staple cartridge assembly (150) is suitably coupled with first portion (102) such that actuator (204) may slide along first side (116) or second side (117) of instrument (100), thereby driving actuating beam (202) and staple sled assembly (160) distally through cartridge assembly (150) to fire instrument (100).

While in the present example, actuator (204) is configured to pivot to either side (116, 117) of instrument (100) to drive actuating beam (202), this is merely optional, as actuator (204) may slidably couple with first portion (102) or second portion (104) through any means apparent to one having ordinary skill in the art in view of the teachings herein. In one example, actuator (204) may strictly associate with first side (116) or second side (117) such that actuator (204) may not pivot when end effector (120) is in the fully closed position. In another example, there may be an actuator (204) positioned on both first side (116) and second side (117), such that instrument (100) may include two actuators (204).

Figure 3:
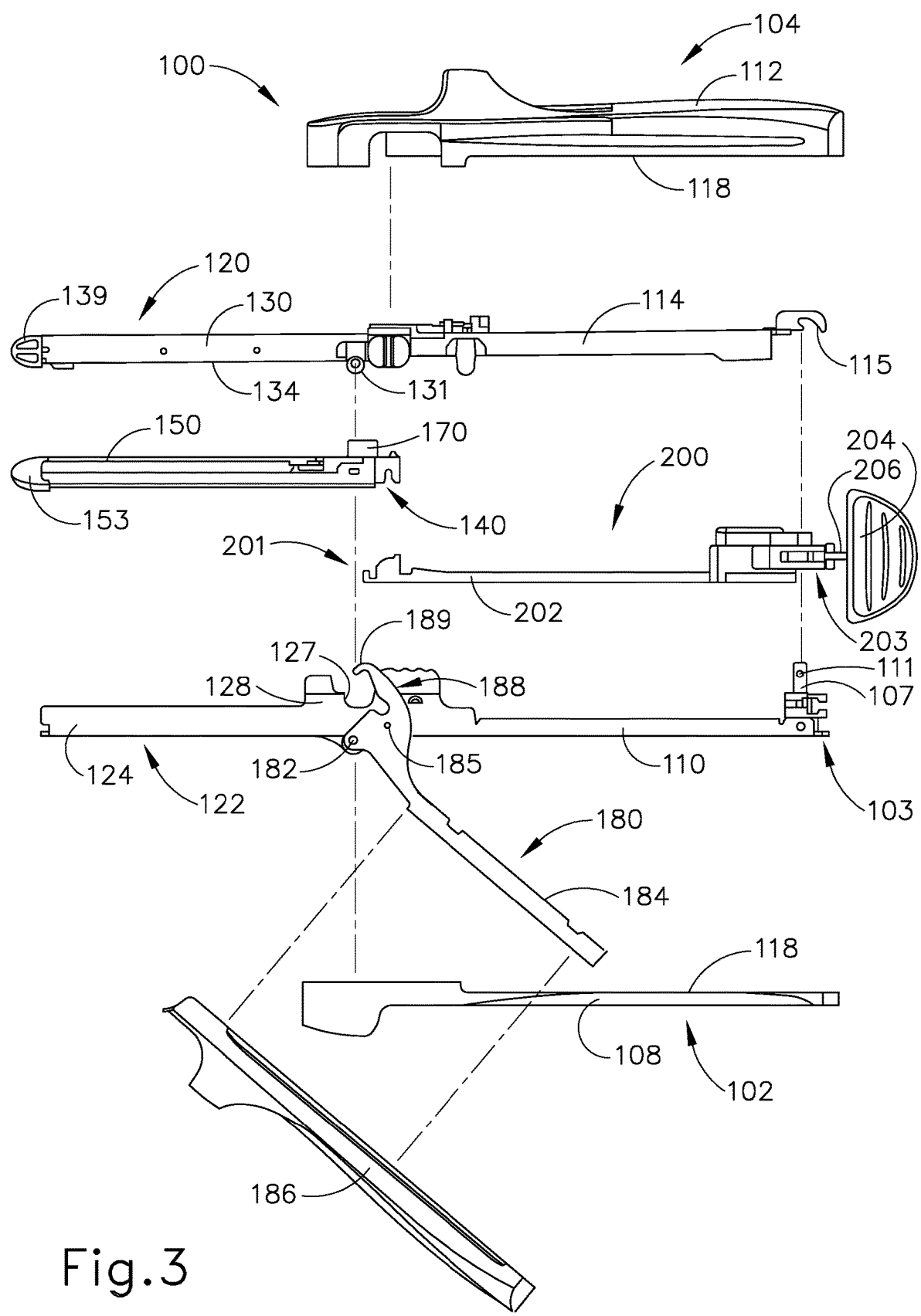
FIG. 3 depicts an exploded elevational side view of the surgical stapling instrument of FIG. 1.

As seen in FIG. 3, first portion (102) includes a first proximal frame (110), staple cartridge channel (122), and a latching lever (180). First proximal frame (110) extends from a proximal end (103) distally into staple cartridge channel (122). In the present example, first proximal frame (110) and staple cartridge channel (122) are formed integrally so as to define an elongate cartridge channel member having a unitary construction. Latching lever (180) is pivotably coupled to either staple cartridge channel (122) or first proximal frame (110) via a pin (182). First proximal frame (110) may be coupled with a handle cover (108) configured to promote sufficient grip such that an operator may control instrument (100) while the operator performs a suitable procedure. Handle cover (108) may couple with first proximal frame (110) by any suitable means as would be apparent to one having ordinary skill in the art in view of the teachings herein. Alternatively, handle cover (108) may be unitarily coupled with first proximal frame (110) or even omitted.

First proximal frame (110) defines a channel that slidably houses actuating beam (202) of firing assembly (200). Proximal end (103) includes one or more lateral pins, or projections (111). Projections (111) are configured to receive grooves (115) of second portion (104) in order to initially pivotably couple first and second portions (102, 104). In the current example, projections (111) are raised from the rest of first proximal frame (110) via a post (107), however this is merely optional. For instance, projections (111) may include a single pin extending laterally across side walls of first proximal frame (110). Of course, any suitable means of initially pivotably couplings first portion (102) and second portion (104) may be used as would be apparent to one having ordinary skill in the art in view of the teachings herein.

Figure 2:
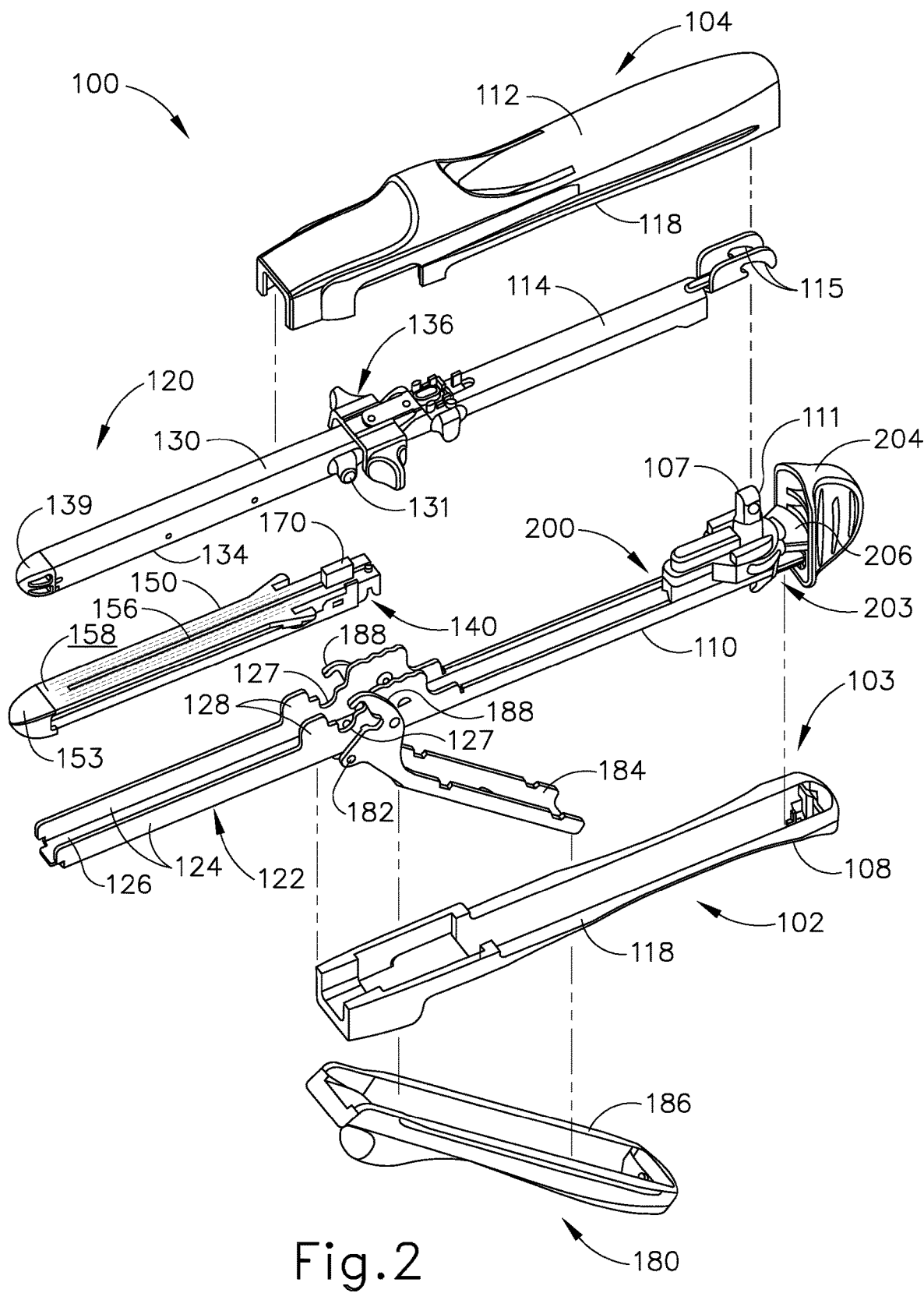
FIG. 2 depicts an exploded perspective view of the surgical stapling instrument of FIG. 1.
Figure 4:
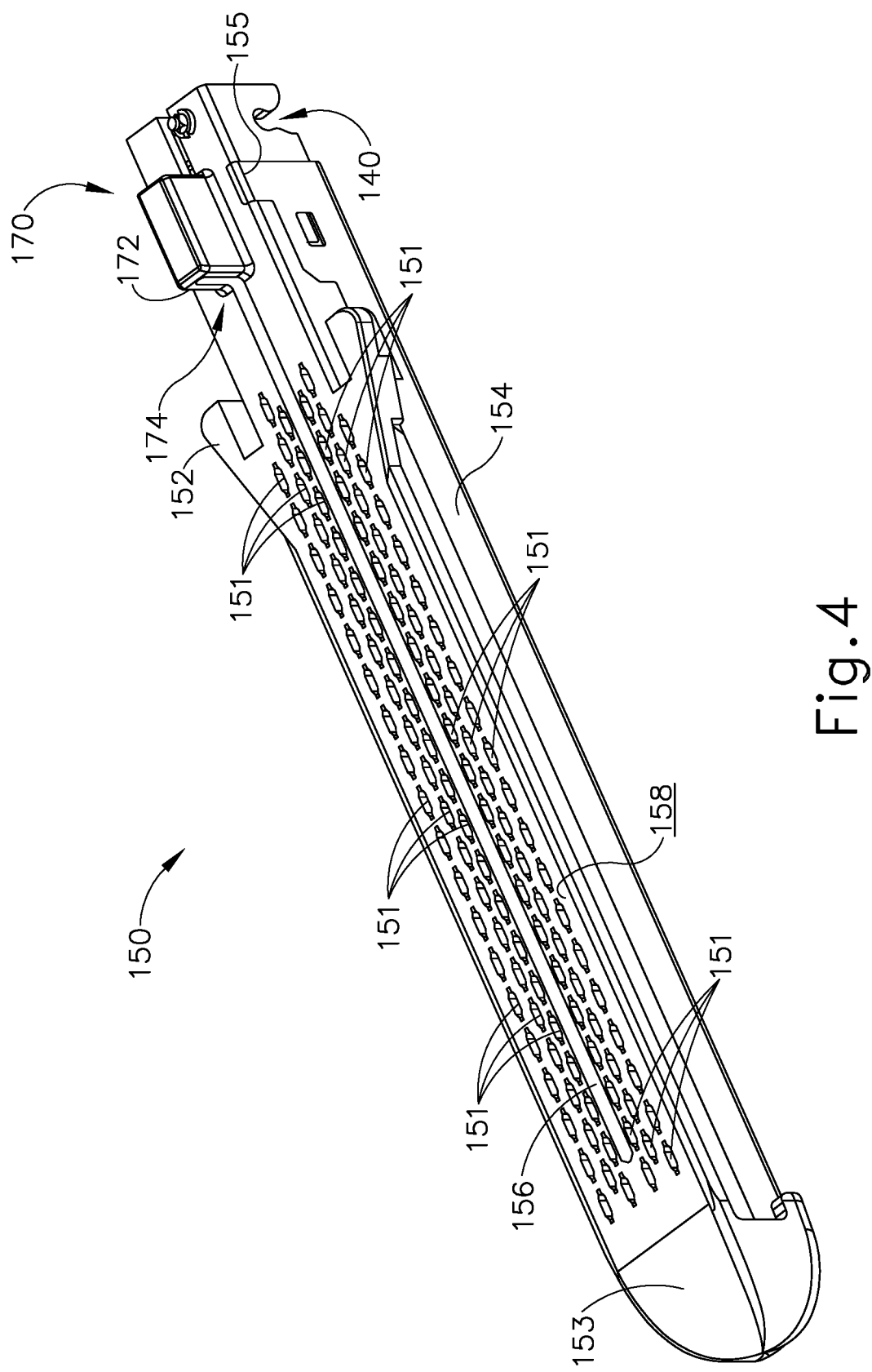
FIG. 4 depicts a perspective view of a staple cartridge assembly of the surgical stapling instrument of FIG. 1.

As briefly mentioned above, staple cartridge channel (122) extends distally from first proximal frame (110). As seen in FIG. 2, staple cartridge channel (122) is dimensioned to selectively couple and decouple with staple cartridge assembly (150). Staple cartridge channel (122) includes a bottom wall (126), and two opposed side walls (124) extending from opposite ends of bottom wall (126). Walls (124, 126) are dimensioned to receive at least a portion of staple cartridge assembly (150), as seen in FIG. 4. Additionally, side walls (124) include inwardly extending lateral projections (not shown) configured to receive coupling cutouts (140) defined by a proximal end of staple cartridge assembly (150). Coupling cutouts (140) may be dimensioned for a snap-fitting or press-fitting with inwardly extending lateral projections (not shown) of side walls (124) such that an operator may selectively attach and detach staple cartridge assembly (150) to staple cartridge channel (122). While coupling cutouts (140) and inwardly extending lateral projections (not shown) are used to selectively couple staple cartridge assembly (150) with staple cartridge channel (122), any other suitable coupling means may be used as would be apparent to one having ordinary skill in the art in view of the teachings herein. Side walls (124) of staple cartridge channel (122) also include side flanges (128) each defining a notch or recess (127). Recesses (127) are dimensioned to receive latch projections (131) of second portion (104) when second portion (104) pivots such that end effector (120) is in a fully closed position (as shown in FIG. 10D) relative to first portion (102).

As briefly mentioned above, latching lever (180) is pivotably coupled to the rest of first portion (102) via pivot pin (182). Latching lever (180) includes a proximal extending arm (184) and a distal latch body (188). Proximal extending arm (184) may be pivoted about pin (182) toward first proximal frame (110) in order to pivot distal latch body (188) toward staple cartridge channel (122) such that distal latch body (188) may engage and pivot second portion (104) toward first portion (102) to transition end effector (120) from a partially closed position (as shown in FIG. 10C) to a fully closed position (as shown in FIG. 10D).

Proximally extending arm (184) may be coupled with an arm cover (186) to promote sufficient grip such that an operator may grasp arm (184) while the operator performs a suitable procedure. Arm cover (186) may be coupled with proximal extending arm (184) by any suitable means as would be apparent to one having ordinary skill in the art in view of the teachings herein. Alternatively, arm cover (186) may be unitarily coupled with proximally extending arm (184) or even omitted.

Distal latch body (188) includes a pair of hooks (189) (or "jaws"). Distal latch body (188) also defines a corresponding pair of latch cutouts (185) located proximally relative to hooks (189). As will be described is greater detail below, each hook (189) is dimensioned to initially make contact with and then capture a respective latch projection (131) of second portion (104) such that distal latch body (188) may wrap around at least a portion of each latch projection (131) to further pivot second portion (104) toward first portion (102). As will also be described in greater detail below, each latch cutout (185) is dimensioned to receive a respective latch projection (131) when end effector (120) is in the closed position relative to first portion (102).

Figure 5:
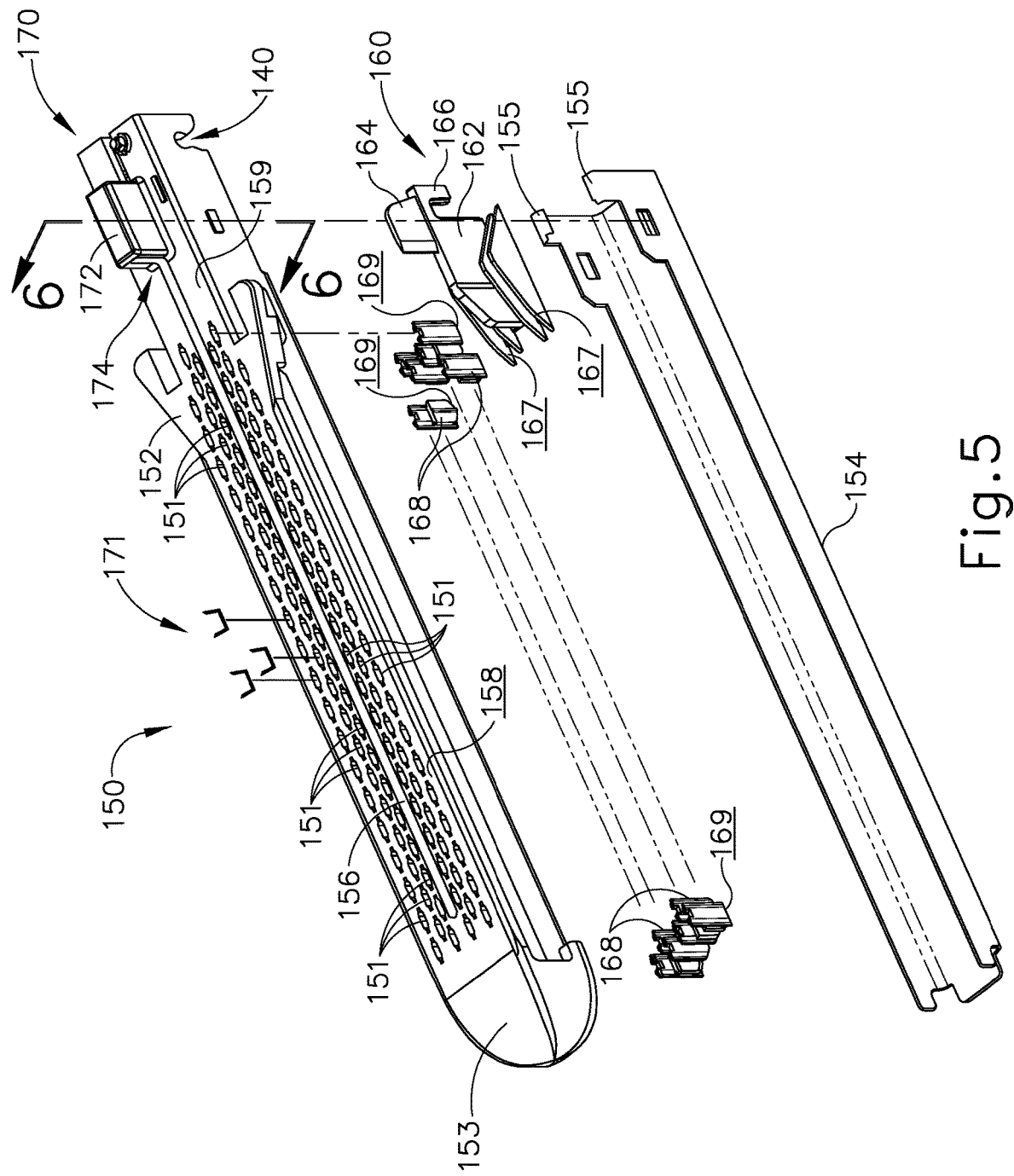
FIG. 5 depicts an exploded view of the staple cartridge assembly of FIG. 4.
Figure 6:
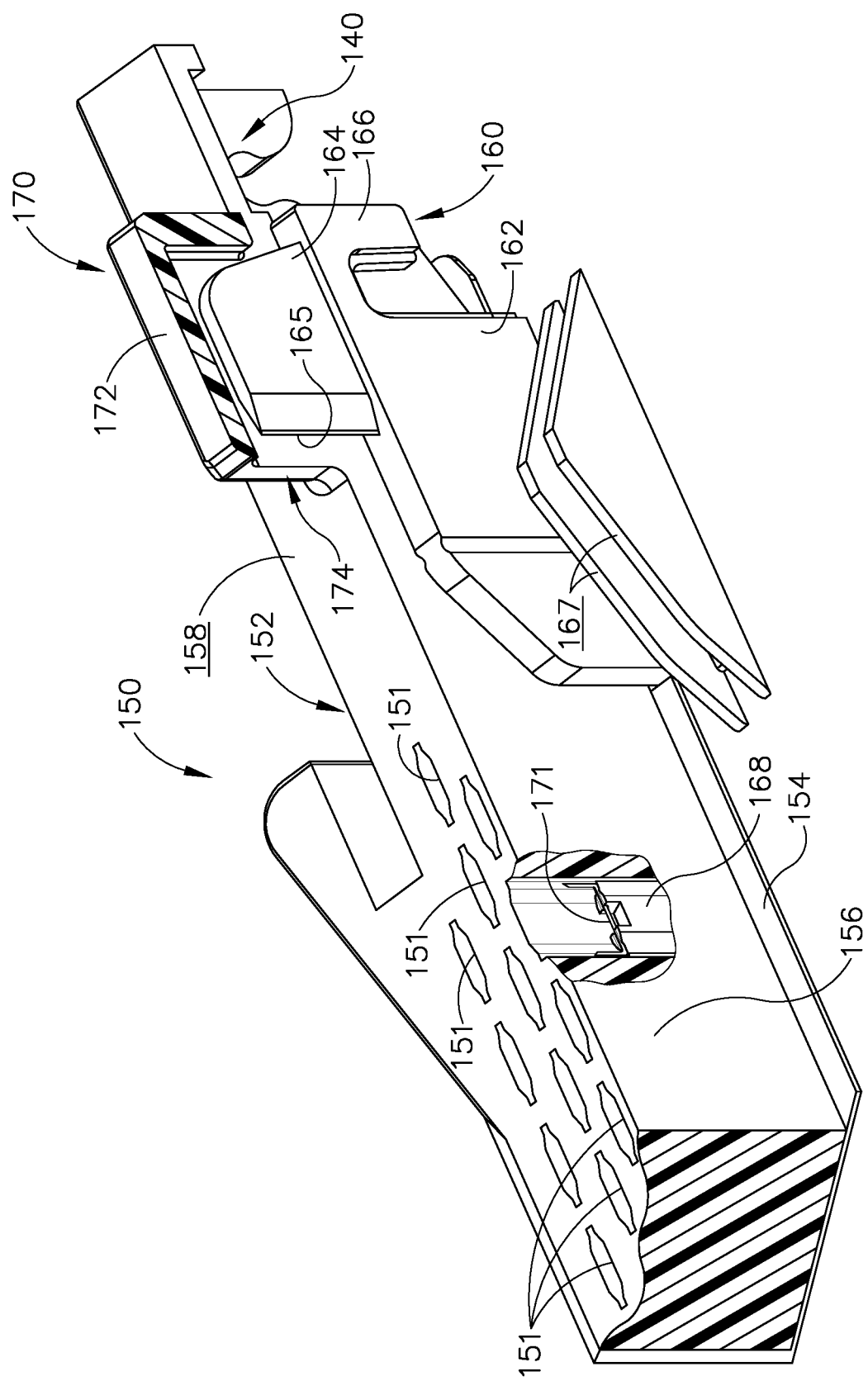
FIG. 6 depicts a cross-sectional perspective view of the staple cartridge assembly of FIG. 4, taken along line 6-6 of FIG. 5.

As best seen in FIGS. 4-6, staple cartridge assembly (150) includes a cartridge body (152), a pan (154), and a plurality of staple drivers (168), each configured to drive a respective staple (171). Cartridge body (152) defines a plurality of staple cavities (151), a slot (156), and coupling cutouts (140). Staple drivers (168) and respective staples (171) are slidably housed within a corresponding staple cavity (151). When first portion (102) and second portion (104) are coupled together, staple cartridge assembly (150) and staple cartridge channel (122) form a portion of end effector (120). As will be described in greater detail below, staple cartridge assembly (150) is configured to house or receive staple sled assembly (160) of firing assembly (200) such that staple sled assembly (160) may actuate through cartridge assembly (150) in order to simultaneously sever and staple tissue captured between the two halves of end effector (120).

As mentioned above, coupling cutouts (140) of cartridge body (152) may be dimensioned for a snap-fitting with inwardly extending lateral projections (not shown) of side walls (124) of staple cartridge channel (122) such that an operator may selectively attach and detach staple cartridge assembly (150) to staple cartridge channel (122). Cartridge body (152) includes a distal nose (153). When staple cartridge assembly (150) is properly coupled with cartridge channel (122), distal nose (153) may extend distally from cartridge channel (122) to provide an atraumatic tip.

Additionally, cartridge body (152) includes a staple deck (158). Staple deck (158) partially defines staple cavities (151) such that staple cavities (151) extend from an interior of cartridge body (152) toward an open end at staple deck (158). Staple cavities (151) each house a corresponding staple driver (168) and staple (171). Similarly, staple deck (158) partially defines slot (156) that extends from an interior of cartridge body (152) toward an open end at staple deck (158). Slot (156) is dimensioned to slidably receive a portion of a sled body (162) and cutting member (164) of staple sled assembly (160) such that cutting member (164) may sever tissue as staple sled assembly (160) slides distally through cartridge body (152).

Pan (154) may include flexible arms (155). Flexible arms (155) may be configured to engage cartridge body (152) such that pan (154) may couple with cartridge body (152) in a snap-fit or press-fit relationship. Pan (154) may couple with cartridge body (152) after staple drivers (168) and staples (171) have been inserted into respective staple cavities (151). Pan (154) may therefore act as a floor for staple drivers (168).

In the current example, cartridge body (152) includes a sled assembly housing (170) located near the proximal end of staple cartridge assembly (150). Sled assembly housing (170) is configured to initially house staple sled assembly (160) of firing assembly (200). Sled assembly housing (170) includes a body (172) defining a cavity (174) having a distally facing opening. Body (172) and cavity (174) are dimensioned to house a cutting member (164) of sled assembly (160) prior to firing, therefore acting as a sheath for cutting member (164). When fired, cutting member (164) may exit sled assembly housing (170) via the distally facing opening of cavity (174).

As seen best in FIGS. 7 and 8, sled assembly (160) includes a sled body (162) and a cutting member (164). Cutting member (164) includes a cutting edge (165) and a lock arm (166). Sled body (162) defines a cutout (161) and a slot (163). Slot (163) is dimensioned to receive a portion of cutting member (164) such that cutting member (164) and sled body (162) may actuate together. Cutting member (164) may couple with sled body (162) via an inference fit with slot (163), through use of adhesives, or any other suitable manner was would be apparent to one having ordinary skill in the art in view of the teachings herein. Alternatively, cutting member (164) may couple with sled body (162) though any suitable manner as would be apparent to one having ordinary skill in the art in view of the teachings herein, such as being unitarily connected, welding, etc. Cutout (161) is dimensioned to couple with distal end (201) of actuating beam (202) when staple cartridge assembly (150) is properly attached to staple cartridge channel (122). Therefore, when properly coupled, actuating beam (202) may drive sled assembly (160) longitudinally through cartridge body (152). It should be understood that since actuating beam (202) is coupled with sled assembly (160) during exemplary use, actuating beam (202) is also dimensioned to slide within slot (156) defined by cartridge body (152).

Sled body (162) also includes a plurality of cam surfaces (167) dimensioned to slide longitudinally within respective elongate grooves (not shown) that pass through staple cavities (151) of cartridge body (152). In particular, cam surface (167) are configured to engage and cam against sloped surfaces (169) of staple drivers (168) within staple cavities (151) in order to actuate staple drivers (168) toward staple deck (158). Staple drivers (168) then drive corresponding staples (171) through staple cavities (151) away from staple deck (158).

As mentioned above, staple sled assembly (160) is configured to couple with the rest of firing assembly (200) when staple cartridge assembly (150) is suitably coupled with staple cartridge channel (122). In the current example, staple sled assembly (160) of firing assembly (200) is associated with cartridge assembly (150) such that after cartridge assembly (150) is used and disposed of, so is staple sled assembly (160). Therefore, when an additional cartridge assembly (150) is loaded into staple cartridge channel (122), a new staple sled assembly (160) will be present. However, this is merely optional. For instance, staple sled assembly (160) may be fixed or otherwise coupled to the rest of firing assembly (200) such that the same staple sled assembly (160) may be used multiple times with multiple staple cartridge assemblies (150). In such examples, cartridge body (152) would not need a sled assembly housing (170). Various ways in which staple sled assembly (160) may be incorporated into either staple cartridge assembly (150), staple cartridge channel (122), or first proximal frame (110) will be apparent to one having ordinary skill in the art in view of the teachings herein.

As shown in FIGS. 2 and 3, second portion (104) of instrument (100) includes a second proximal frame (114), anvil channel (130), latch projections (131), and an anvil surface disposed along and supported by anvil channel (130) and shown in the form of anvil plate (134). Second proximal frame (114) extends from a proximal end defining grooves (115) in anvil channel (130). In the present example, second proximal frame (114) and anvil channel (130) are formed integrally so as to define an elongate anvil channel member having a unitary construction. Second proximal frame (114) may be coupled with a handle cover (112) configured to promote sufficient grip such that an operator may control instrument (100) while the operator performs a suitable procedure. Handle cover (112) and second proximal frame (114) may couple with each other by any suitable means as would be apparent to one having ordinary skill in the art in view of the teachings herein. Alternatively, handle cover (112) may be unitarily coupled with second proximal frame (114) or even omitted. Second proximal frame (114) may also define a channel configured to enable portions of firing assembly (200) to actuate relative to first portion (102) and second portion (104) when end effector (120) is in the fully closed position (as shown in FIG. 10D).

Figure 9:
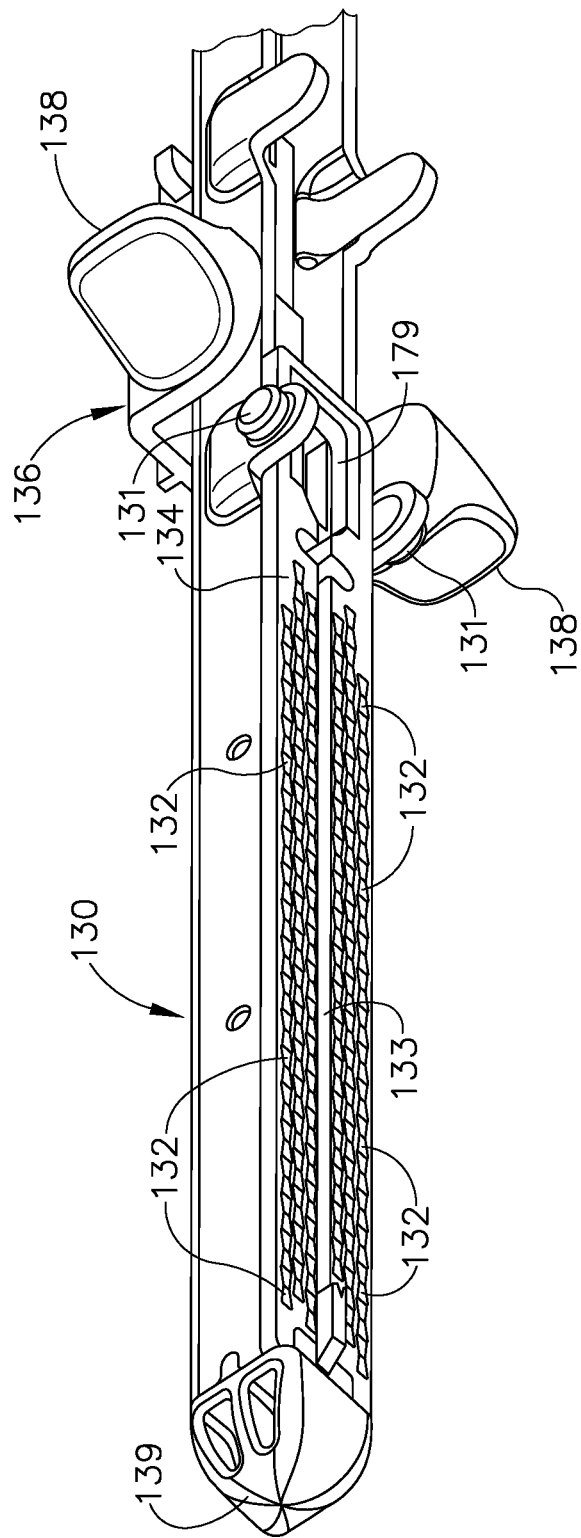
FIG. 9 depicts a perspective view of an anvil assembly of the surgical stapling instrument of FIG. 1.

Second portion (104) terminates distally in a distal nose (139). Distal nose (153) may extend distally from anvil channel (130) to provide an atraumatic tip. As shown in FIG. 9, proximal end of anvil plate (134) defines a recess (179) dimensioned to receive sled assembly housing (170) when first portion (102) and second portion (104) are pivoted toward each other. As will be described in greater detail below, latch projections (131) extend laterally away from anvil channel (130) and are dimensioned to interact with distal latch body (180) to draw anvil plate (134) toward staple cartridge assembly (150).

Anvil plate (134) defines a plurality of staple forming pockets (132) and a slot (133). Staple forming pockets (132) are positioned along anvil plate (134) such that each staple forming pocket (132) aligns with a corresponding staple cavity (151) when anvil channel (130) is pivoted toward staple cartridge channel (122) to the fully closed position (as shown in FIGS. 1, 10D, and 11A-B). Therefore, when cam surfaces (167) of sled body (162) actuate staple drivers (168) in accordance with the description above, staples (171) are driven through staple cavities (151) away from staple deck (158), through tissue, and against a corresponding staple forming pocket (132) such that staples (171) transform from a general "U" shape into a general "B" shape in order to suitably staple tissue. Slot (133) is dimensioned to laterally align with slot (156) of staple cartridge assembly (150) when anvil channel (130) is pivoted to the fully closed position (as shown in FIGS. 1, 10D, 11A-11B). Slot (133) is dimensioned to slidably receive a portion of cutting member (164) as staple sled assembly (160) is driven through staple cartridge assembly (150) such that cutting member (164) may sever tissue captured between anvil surface (134) and staple deck (158) during exemplary use.

As seen best in FIG. 9, second portion (104) of instrument (100) of the present example further includes a staple height adjustment mechanism (136). Adjustment mechanism (136) is operatively coupled with anvil plate (134), for example via one or more camming features (not shown), and includes a pair of user-engageable projections (138). Adjustment mechanism (136) is selectively movable relative to anvil channel (130) between two or more longitudinal positions to raise or lower anvil plate (134) relative to anvil channel (130), and thereby adjust a gap distance (or "tissue gap") between anvil plate (134) and staple deck (158) when first and second instrument portions (102, 104) are coupled together in a fully closed position. A larger gap distance, and thus a greater staple height, may be provided for stapling tissues of greater thicknesses. Similarly, a smaller gap distance, and thus a smaller staple height, may be provided for stapling tissues of lesser thicknesses. It will be appreciated that staple height adjustment mechanism (136) is merely optional and may be omitted in other versions. In some versions of instrument (100), the anvil surface, shown in the form of anvil plate (134), may be fixed relative to anvil channel (130). For instance, the anvil surface may be formed integrally with anvil channel (130).

Surgical linear cutting stapler (100) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Cutting Stapler

Figure 10A:
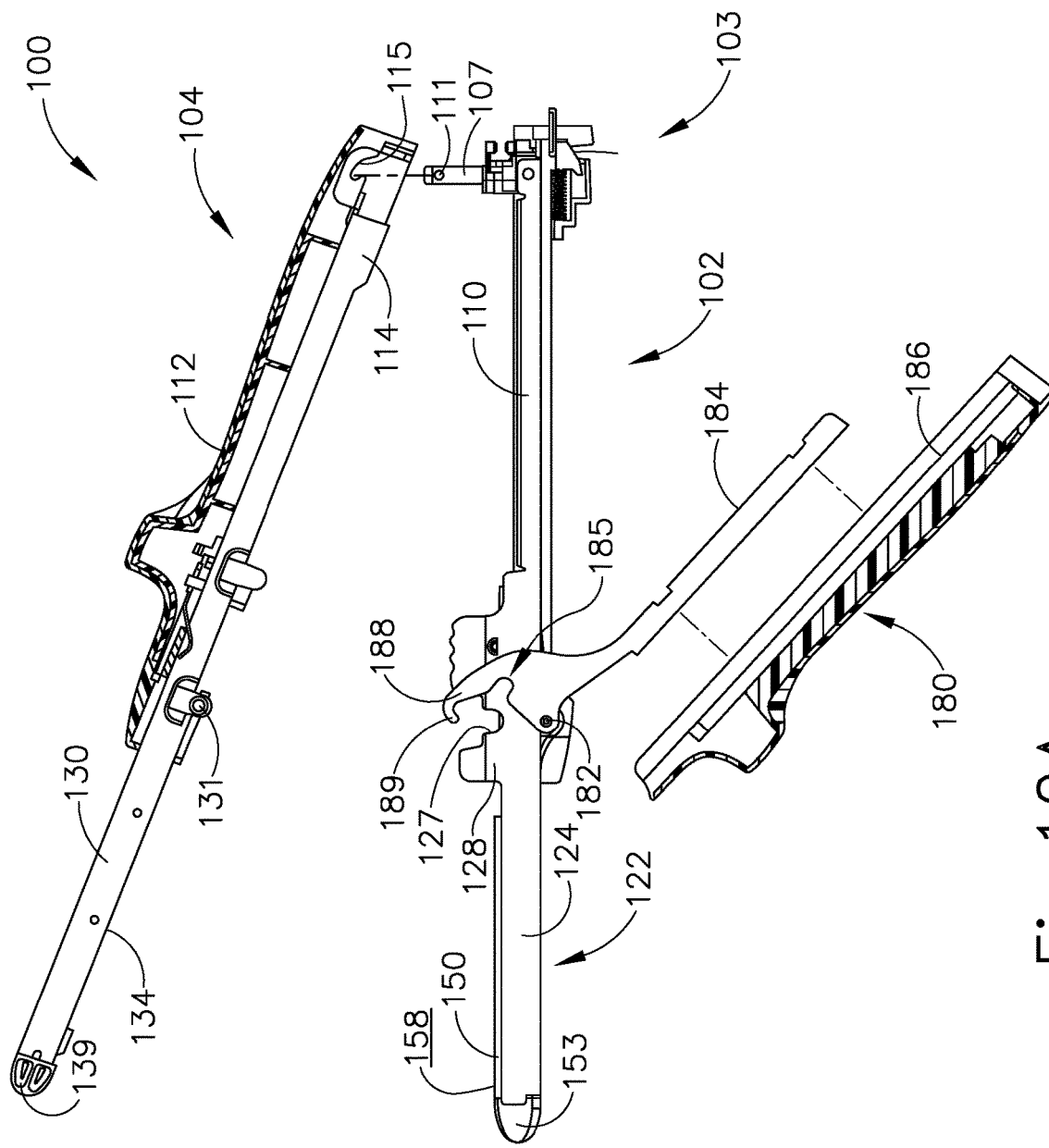
FIG. 10A depicts a cross-sectional side view of the surgical stapling instrument of FIG. 1, where a first portion and a second portion are decoupled from each other, and where an arm cover is shown detached from the first portion for illustrative purposes.
Figure 10B:
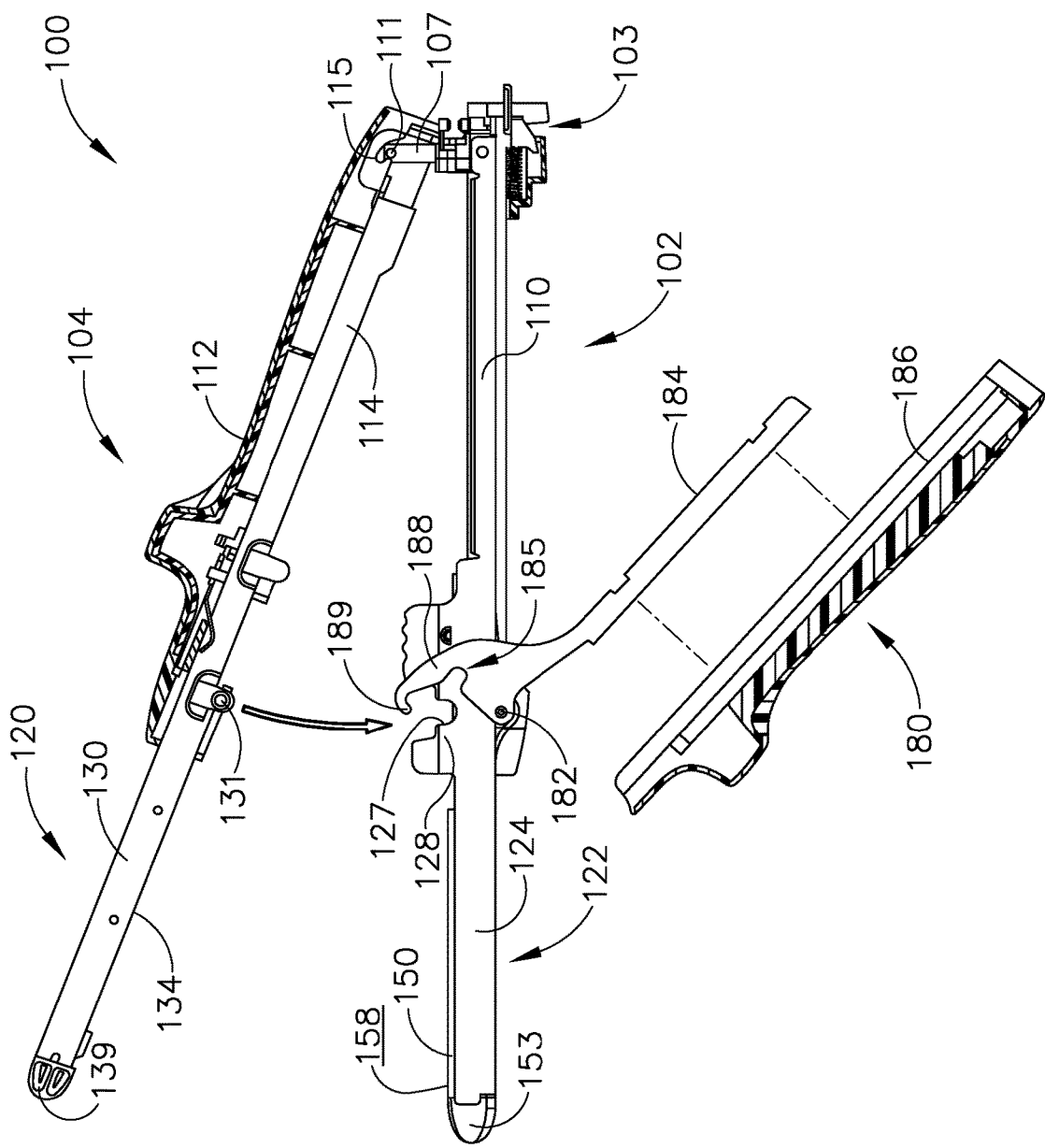
FIG. 10B depicts a cross-sectional side view of the surgical instrument of FIG. 1, where the first portion and second portion of FIG. 10A are coupled with each other in an opened position, and the arm cover is shown detached from the first portion for illustrative purposes.
Figure 10C:
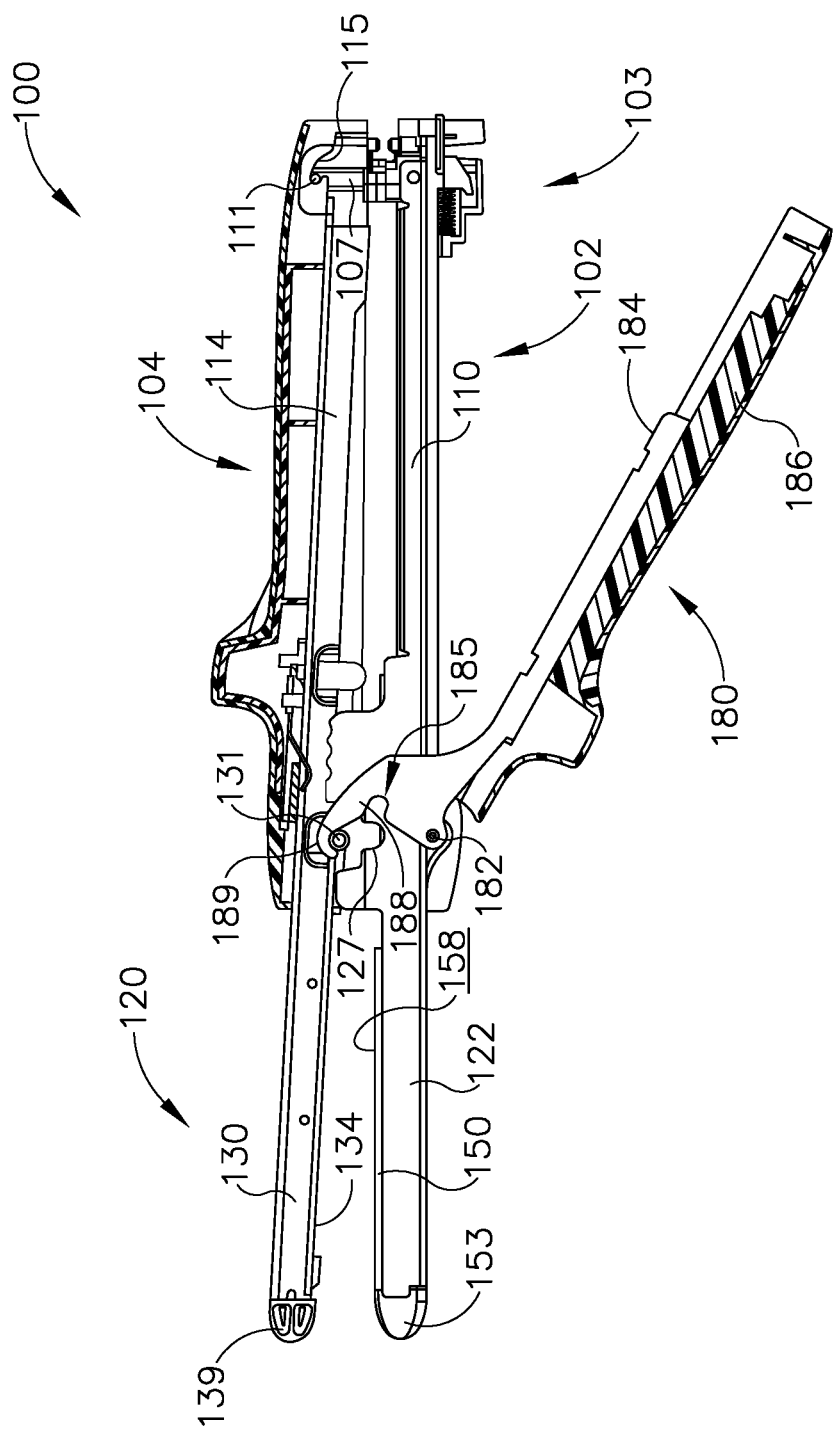
FIG. 10C depicts a cross-sectional side view of the surgical instrument of FIG. 1, where the first portion and the second portion of FIG. 10A are coupled with each other in a partially closed position, and where the arm cover is attached to the first portion.
Figure 10D:
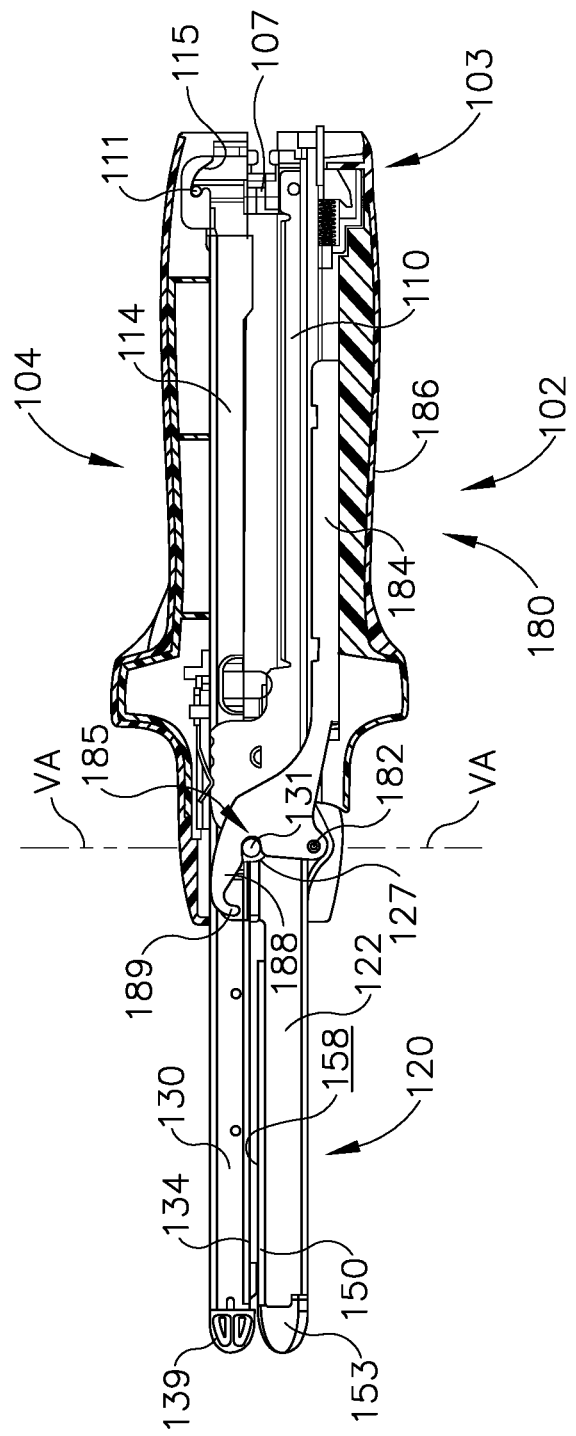
FIG. 10D depicts a cross-sectional side view of the surgical instrument of FIG. 1, where the first portion and the second portion of FIG. 10A are coupled with each other in a fully closed position.
Figure 11A:
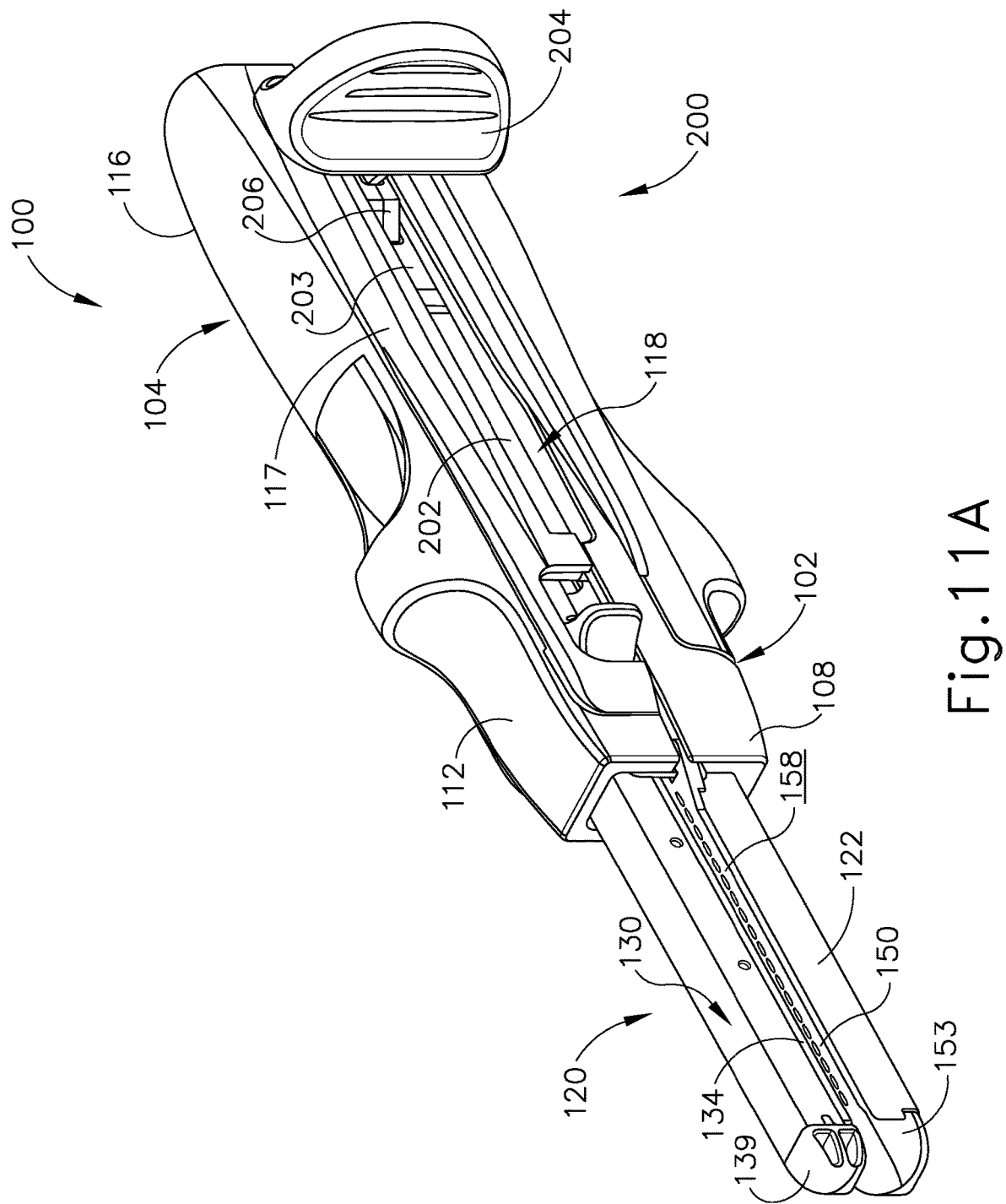
FIG. 11A depicts a perspective view of the surgical instrument of FIG. 1, where a firing assembly is in a pre-fired position.
Figure 11B:
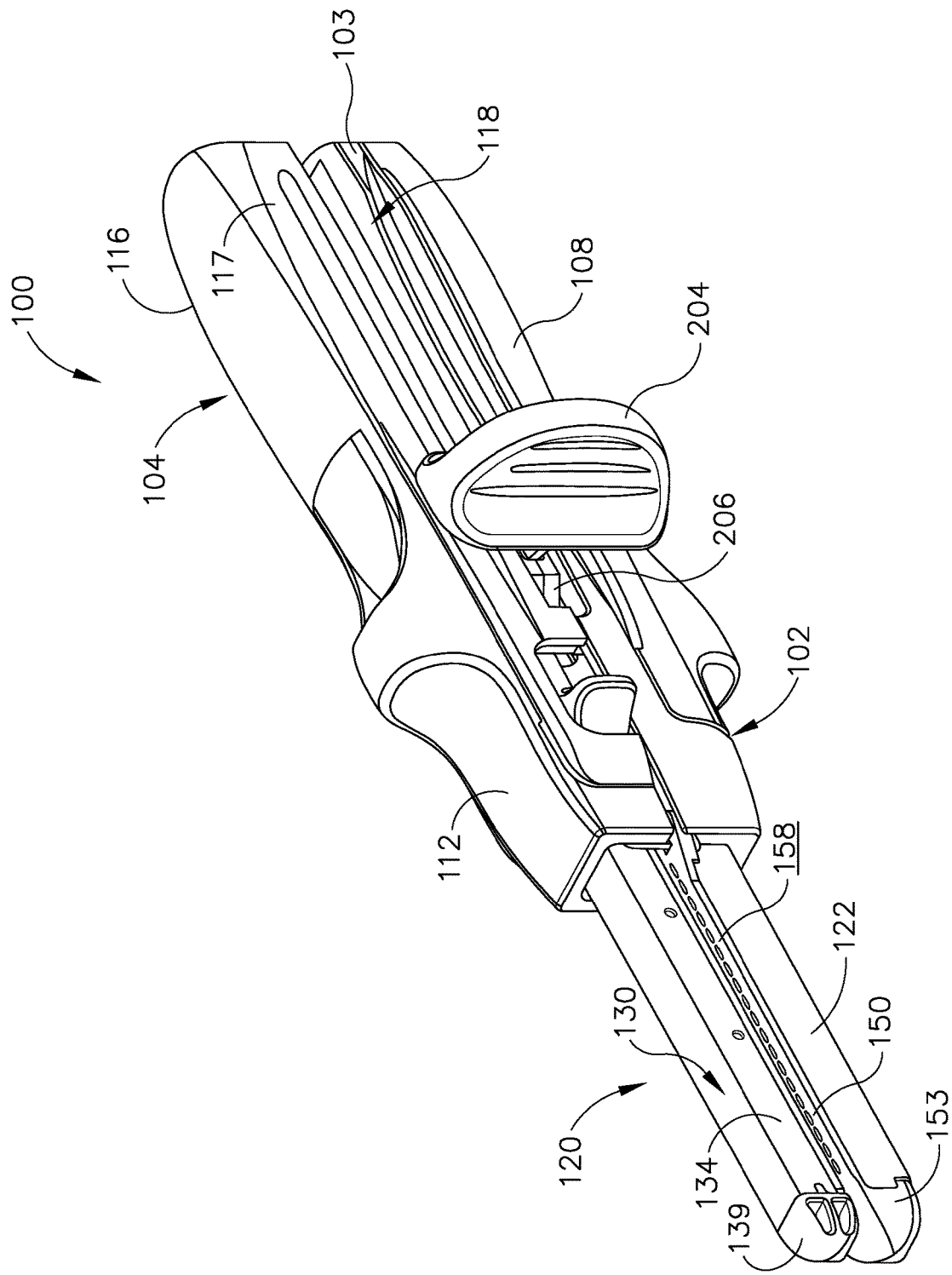
FIG. 11B depicts a perspective view of the surgical instrument of FIG. 1, where the firing assembly of FIG. 11A is in a fired position.

FIGS. 10A-11B show an exemplary use of linear cutting stapler (100). In particular, FIGS. 10A-10D show an exemplary coupling of first portion (102) with second portion (104), and pivoting first portion (102) and second portion (104) such that end effector (120) transitions from an open position (FIG. 10B), to a partially closed position (FIG. 10C), and finally to a fully closed position (FIG. 10D). FIGS. 11A-11B show an exemplary firing of instrument (100) when end effector (120) is in a fully closed position.

FIG. 10A shows first portion (102) completely detached from second portion (204). Additionally, staple cartridge assembly (150) is suitably attached to staple cartridge channel (122) in accordance with the description above. At this point during a procedure, such as during a gastrointestinal anastomosis, an operator may desire to place lumens of tissue over and past distal noses (139, 153) of second portion (104) and cartridge assembly (150), respectively, such that lumens of tissue are suitably associated with both anvil plate (134) and cartridge assembly (150). At this point, an operator may align grooves (115) of second portion (104) with corresponding lateral projections (111) of first portion (102) in preparation of initially pivotally coupling first portion (102) with second portion (104).

Next, as shown in FIG. 10B, an operator may insert lateral projections (111) into corresponding grooves (115) such that first portion (102) and second portion (104) are pivotally coupled, but end effector (120) is in an open position. First portion (102) and second portion (104) may pivot relative to each other about the axis defined by lateral projections (111). At this point, latching lever (180) is not in contact with any portion of second portion (104). Additionally, latching lever (180) is in an open position such that proximal extending arm (184) is pivoted away from first proximal frame (110).

Next, as shown in FIG. 10C, an operator may initially pivot anvil channel (130) and anvil plate (134) toward cartridge channel (122) and staple cartridge assembly (150), and partially pivot latching lever (180) such that hooks (189) initially contact latch projections (131). At this point, end effector (120) is in the partially closed position. As best shown between FIGS. 10C-10D, after hooks (189) initially contact latch projections (131), an operator may further rotate proximal extending arm (184) toward first proximal frame (110), causing distal latch body (188) to drive latch projections (131) along the surfaces of distal latch body (188) toward latch cutouts (185). As latch projections (131) are driven toward latch cutouts (185), anvil channel (130) and anvil plate (134) rotate further toward cartridge channel (122) and staple cartridge assembly (150) such that end effector (120) is in the closed position. Additionally, latch projections (131) are also driven toward recesses (127) of staple cartridge channel (122) such that each latch projection (131) is encompassed by a combination of the respective latch cutout (185) and recess (127), effectively latching end effector (120) into the closed position. Latch cutouts (185) and recesses (127) may be dimensioned to interface with latch projections (131) while end effector (120) is in the fully closed position such that latch projections (131) and pivot pin (182) extend along a vertical axis (VA) that is substantially perpendicular with the longitudinal axis of instrument (100). This may provide a mechanical advantage for an enhanced closure force during suitable use.

FIGS. 11A-11B show an exemplary firing of instrument (100) with end effector (120) in the fully closed position. As best seen in FIG. 11A, an operator may pivot actuator (204) to either side (116, 117) of instrument (100). In the present example, actuator (204) has been pivoted to second side (117) of instrument (100). Next, operator may push actuator (204) distally toward end effector (120) within slot (118), such that actuating beam (202) and sled (160) are fired, thereby stapling and severing tissue captured between stapling deck (158) and anvil plate (134) in accordance with the description above. Once instrument (100) has been fired, an operator may pull actuator (204) proximally back to the position shown in FIG. 11A, then rotate actuator (204) back to the position shown in FIG. 1. An operator may then pivot latching lever (180) such that proximally extending arm (184) is pivoted away from first proximal frame (110) in order to open end effector (120) from the fully closed position to the partially closed position. An operator may further pivot latching lever (180) such that distal latch body (188) no longer captures latch projections (131). Then an operator may decouple first portion (102) and second portion (104) from each other and replace staple cartridge assembly (150), if desired.

II. Exemplary Linear Cutting Stapler Having Releasable Locking Member

As described above in connection with surgical stapler (100), a pivotable coupling is established between the proximal ends of instrument halves (102, 104) when projections (111) of cartridge half (102) are received within grooves (115) of anvil half (104). As shown in FIGS. 10A and 10B, projections (111) and grooves (115) are fixed relative to their respective instrument half (102, 104), such that they establish a passive coupling with one another that automatically releases when anvil half (104) is pivoted away from cartridge half (102) by a minimum angle.

In some instances, it may be desirable to provide a more active coupling between the proximal ends of the first and second halves of a surgical stapler, such that the halves decouple only upon a specific user input. Such a configuration may protect against unintentional decoupling of the instrument halves, and enhance the suitability of the stapler for single handed manipulation during initial steps of a surgical procedure, such that the other hand of an operator is left free to manipulate tissue relative to the stapler. The exemplary surgical stapler (300) described below includes features that provide such a coupling between first and second halves of stapler (300).

A. Overview of Exemplary Linear Cutting Stapler

Figure 12:
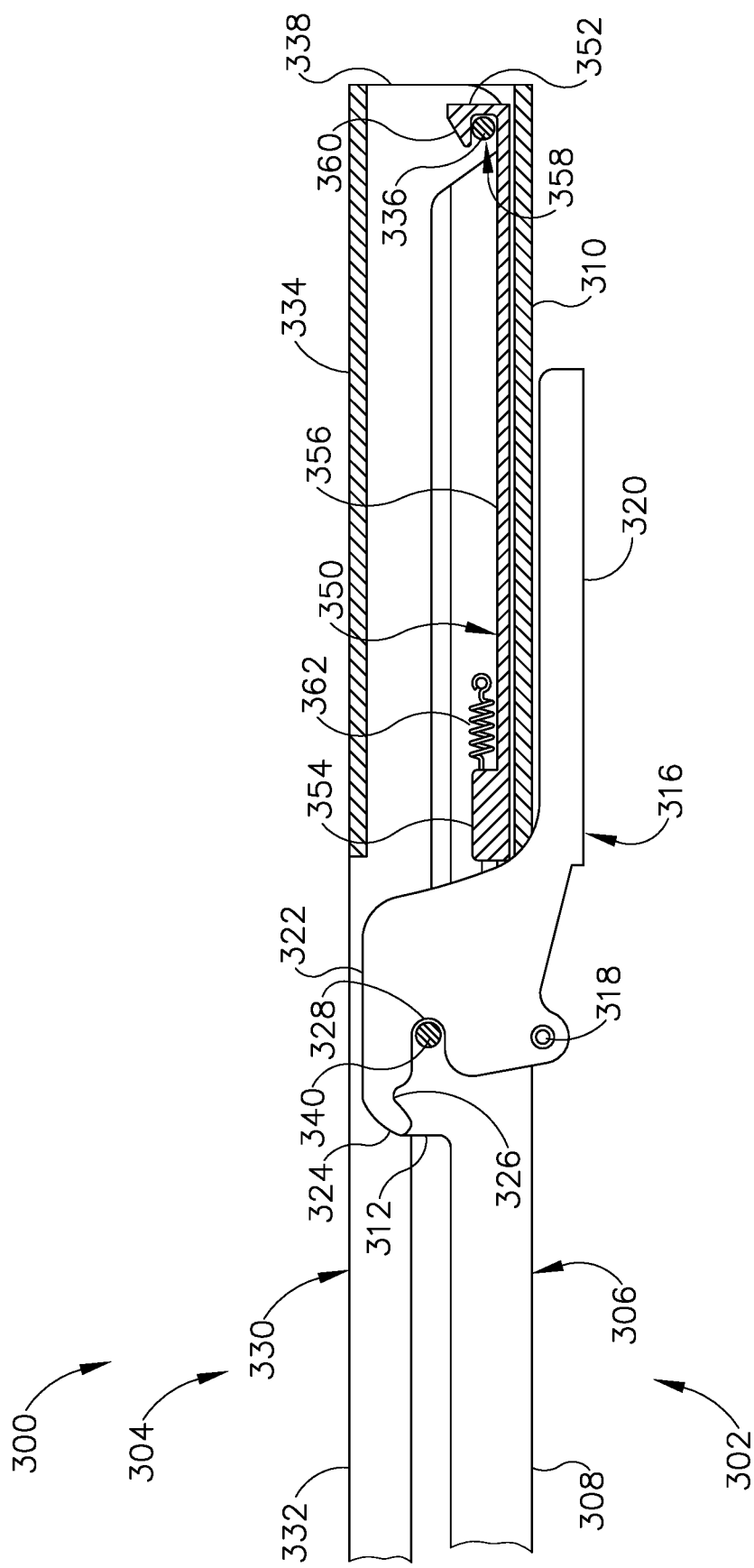
FIG. 12 depicts a cross-sectional side view of another exemplary surgical stapling instrument, showing a latching lever of the instrument in a closed position and a proximal locking member of the instrument in a locked position.
Figure 13A:
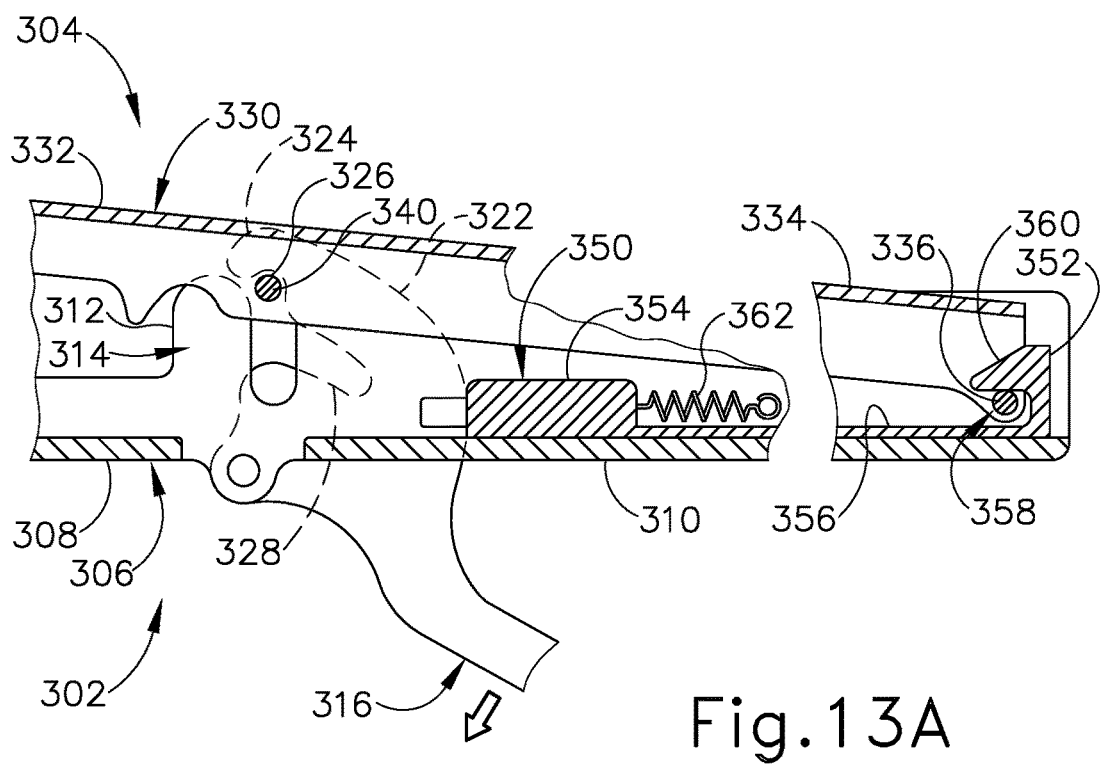
FIG. 13A depicts a cross-sectional side view of the surgical stapling instrument of FIG. 12, showing the latching lever in phantom in a partially closed position, and the proximal locking member in the locked position.
Figure 13B:
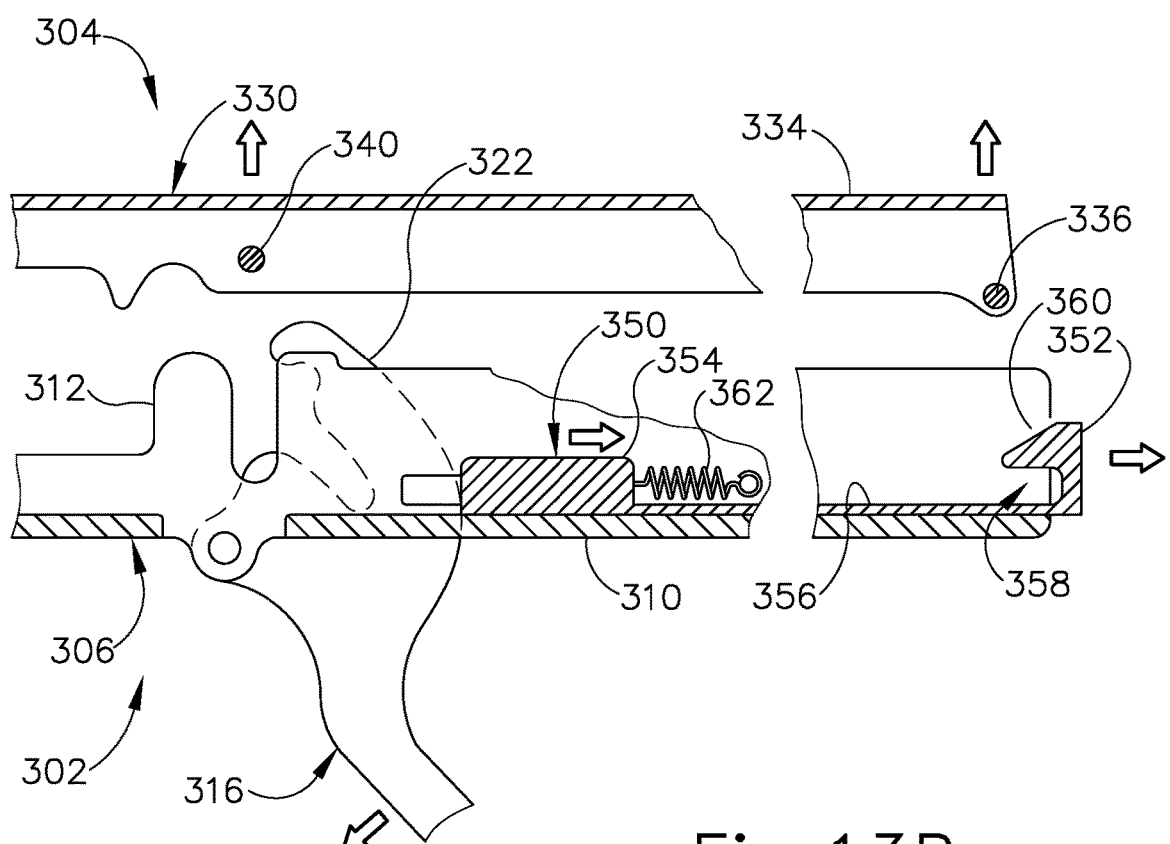
FIG. 13B depicts a cross-sectional side view of the surgical stapling instrument of FIG. 12, showing the latching lever in phantom in an open position and the proximal locking member in an unlocked position.

FIGS. 12-13B show another exemplary linear cutting stapler (300) that is similar to linear cutting stapler (100) described above, except as otherwise described below. Stapler (300) includes a cartridge half (302) and an anvil half (304) configured to releasably couple together. Cartridge half (302) includes an elongate cartridge channel member (306) having a distal channel portion (308) defining a distal end of cartridge channel member (306), and a proximal frame portion (310) defining a proximal end of cartridge channel member (306). Distal channel portion (308) is configured to receive a staple cartridge (not shown), which may be similar to staple cartridge (150) described above. Proximal frame portion (310) is configured to slidably retain components of a firing assembly (not shown), which may be similar to firing assembly (200) described above. As best seen in FIGS. 13A and 13B, cartridge channel member (306) further includes a pair of upright side flanges (312) arranged medially between distal channel portion (308) and proximal frame portion (310). Each medial side flange (312) includes a slot (314) that extends transversely to a longitudinal axis of cartridge channel member (306) and opens to a side of cartridge half (302) that faces anvil half (304).

Cartridge half (302) further includes a latching lever (316) pivotably coupled to cartridge channel member (306) with a pivot pin (318) arranged at a medial portion of cartridge channel member (306) corresponding to medial side flanges (312). In the present example, latch pivot pin (318) is approximately aligned with transverse slots (314) of medial side flanges (312), as seen in FIG. 13A. Latching lever (316) includes an elongate lever arm (320) and a pair of opposed jaws (322) extending distally from lever arm (320) and curving towards anvil half (304), as best seen in FIG. 12. Each jaw (322) of the present example includes a hook end (324) having a recessed cutout (326), and a slot (328) arranged proximal to cutout (326) and having a closed proximal end.

Similar to latching lever (180) described above, latching lever (316) is configured to pivot relative to cartridge channel member (306) to selectively clamp anvil half (304) against cartridge half (302). As described in greater detail below, latching lever (316) is pivotable relative to cartridge channel member (306) between a fully open position (see FIG. 13B) in which latching lever (316) permits cartridge channel member (306) and anvil channel member (330) to be separated from one another; a partially closed (or "partially open") position (see FIG. 13A) in which latching lever (316) couples channel members (306, 330) together but still permits some movement between channel members (306, 330); and a fully closed position (see FIG. 12) in which latching lever (316) fixes channel members (306, 330) together.

Anvil half (304) of linear cutting stapler (300) includes an elongate anvil channel member (330) having a distal channel portion (332) and a proximal frame portion (334). Distal channel portion (332) is configured to support an anvil surface (not shown) having a plurality of anvil forming pockets. In some examples, the anvil surface may be similar to anvil plate (134) described above. In other versions, the anvil surface may be integrally formed with or otherwise rigidly coupled to distal channel portion (332). In such other versions, it will be appreciated that the anvil surface is still "supported by" distal channel portion (336). Distal channel portion (332) is also configured to support a distal tip member (not shown) similar to distal tip member (139) described above defining a distal end of anvil half (304). Proximal frame portion (334) defines a proximal end of anvil channel member (330), and supports a laterally extending pin (336) at the proximal end. As described below, anvil channel member (330) is configured to pivot relative to cartridge channel member (306) about an axis defined by proximal pin (336).

In the present example, proximal frame portion (334) of anvil channel member (330) further includes a pair of upright flanges (338) arranged at its proximal end, and proximal pin (336) extends laterally between proximal flanges (338). Additionally, proximal frame portion (334) is formed with a smaller lateral width than proximal frame portion (310) of cartridge channel member (306). Accordingly, proximal frame portion (334) of anvil channel member (330) is configured to be received between opposing sidewalls of proximal frame portion (310) of cartridge channel member (306), as shown in FIGS. 12 and 13A, described in further detail below.

Anvil half (304) further includes a pair of latch projections configured to be engaged by latching lever (316) of cartridge half (302). In the present example, the latch projections are defined by opposed ends of a latch pin (340) extending laterally through opposing sidewalls of anvil channel member (330) at a medial location between distal channel portion (332) and proximal frame portion (334). In other examples, the latch projections of stapler (300) may be similar to latch projections (131) described above. Though not shown, cartridge channel member (306), latching lever (316), and anvil channel member (330) may each include a cover similar to covers (108, 112, 186) described above, to facilitate gripping of stapler halves (302, 304) by an operator. It will be appreciated that various other features of stapler (100) described above may be incorporated in stapler (300) as well.

During assembly of stapler halves (302, 304), latching lever (316) is maintained in the fully open position (FIG. 13B) while the proximal ends of halves (302, 304) are aligned with one another such that the proximal end of anvil channel member (330) is received by the proximal end of cartridge channel member (306), as shown in FIG. 13A and described in further detail below. Latching lever (316) is then pivoted from the fully open position (FIG. 13B) to the partially-closed position (FIG. 13A), such that hook ends (324) of lever jaws (322) capture the opposed ends of latch pin (340) within recessed cutouts (326). In this partially-closed position of latching lever (316), anvil channel member (330) is longitudinally fixed relative to cartridge channel member (306) but is still permitted to pivot further toward cartridge channel member (306) about proximal pin (336). This partially-closed position enables an operator to grasp stapler (300) with one hand while manipulating tissue between the distal portions of stapler halves (302, 304) with the other hand.

As latching lever (316) is rotated further from the partially-closed position (FIG. 13A) to the fully closed position (FIG. 12), lever jaws (322) draw the opposed ends of latch pin (340) into jaw slots (328), thereby causing anvil half (304) to pivot further toward cartridge half (302) to clamp tissue between the anvil surface (not shown) and the staple cartridge (not shown). In this fully closed position of latching lever (316), lever jaws (322) capture the ends of latch pin (340) against the closed proximal ends of jaw slots (328), thereby fixing anvil channel member (330) relative to cartridge channel member (306) and rendering the stapler (300) ready for firing to simultaneously staple and cut the clamped tissue with the firing assembly (not shown).

B. Exemplary Translating Locking Structure of Cartridge Half

Following stapling of tissue, stapler halves (302, 304) of stapler (300) may be separated from one another by returning the firing assembly (not shown) to its proximal home position, and pivoting the latching lever (316) to its fully open position (FIG. 13B). As described below, the proximal ends of stapler halves (302, 304) remain securely locked together while latching lever (316) is in the fully closed position (FIG. 12) and the partially-closed position (FIG. 13A), and release from one another only upon lever (316) reaching the fully open position (FIG. 13B). In the present example, latching lever (316) activates release of anvil half (304) from cartridge half (302), as described below.

As seen in FIGS. 12-13B, cartridge half (302) further includes a translating locking structure (350) configured to selectively lock and unlock the proximal end of anvil half (304) relative to the proximal end of cartridge half (302) in response to pivoting of latching lever (316) between the fully closed position (FIG. 12) and the fully open position (FIG. 13B). In the present example, translating structure (350) is slidably disposed within proximal frame portion (310) of cartridge channel member (306), and includes a proximal locking member (352), a distal sliding member (354), and an elongate actuating member (356) extending therebetween. Additionally, in the present example, members (352, 354, 356) are integrally coupled together so as to provide translating structure (350) with a unitary structure. In other examples, members (352, 354, 356) may be formed as separate components that are coupled together, such as by one or more movable couplings, to define translating structure (350).

Locking member (352) of the present example is shown in the form of a hook feature that projects distally over a proximal end of actuating member (356) so as to define a channel (358) between a lower surface of locking member (352) and an upper surface of the proximal end of actuating member (356). As shown in FIGS. 12 and 13A and as described below, locking member (352) is configured to hook over and capture proximal pin (336) of anvil half (304) within locking channel (358) to thereby secure anvil half (304) to cartridge half (302). Locking member (352) further includes a sloped upper surface (360) configured to funnel proximal pin (336) distally toward actuating member (356) and into locking channel (358) when the proximal ends of stapler halves (302, 304) are being initially coupled together.

As shown in FIGS. 12-13B, translating structure (350) is configured to translate along a longitudinal axis of proximal frame portion (310) of cartridge channel member (306) between a distal locked position and a proximal unlocked position. In the distal locked position (see FIGS. 12 and 13A), locking member (352) captures and retains proximal pin (336) of anvil half (304) within locking channel (358) to thereby prevent transverse separation of the proximal end of anvil half (304) from the proximal end of cartridge half (302), while still permitting anvil half (304) to pivot relative to cartridge half (302) about proximal pin (336). In the proximal unlocked position (see FIG. 13B), locking member (352) releases proximal pin (336) of anvil half (304) to thereby permit transverse separation of the proximal end of anvil half (304) from the proximal end of cartridge half (302). In the present example, translating structure (350) is resiliently biased toward the distal locked position by a resilient member shown in the form of a compression spring (362). A proximal end of spring (362) is anchored to proximal frame portion (310) of cartridge channel member (306), and a distal end of spring (362) is coupled to and movable with a proximal end of sliding member (354).

Sliding member (354) of the present example is shown in the form of a block-like structure having a distal face configured to contact a proximally facing edge of one or both jaws (322), or otherwise contact an element coupled to a proximal portion of one or both jaws (322). As shown in FIGS. 12-13B, jaws (322) are configured to couple with the distal face of sliding member (354), via direct or indirect contact, when latching lever (316) is pivoted from fully closed position (FIG. 12) to the partially-closed position (FIG. 13A). Upon further pivoting of latching lever (316) from the partially-closed position toward the open position (FIG. 13B), jaws (322) drive sliding member (354) proximally via a camming action. Accordingly, sliding member (354) of the present example is configured to operate as a cam follower. The proximal translation of sliding member (354) compresses spring (362) and is communicated proximally to locking member (352) via actuating member (356). Upon latching lever (316) reaching the fully open position (FIG. 13B), jaws (322) release latch pin (340) of anvil half (304) and drive locking member (352) proximally to its unlocked position so that locking member (352) releases proximal pin (336) of anvil half (304). Anvil half (304) is fully released from cartridge half (302) such that stapler halves (302, 304) may be separated from one another by the operator. Accordingly, the proximal ends of stapler halves (302, 304) remain securely coupled together until the operator specifically intends to release them by pivoting latching lever (316) to the fully open position.

In the present example, translating structure (350) remains in the proximal unlocked position while latching lever (316) is in the open position (FIG. 13B) via the camming engagement between lever jaws (322) and sliding member (354). The proximal ends of stapler halves (302, 304) may be recoupled together, or initially coupled together, by holding latching lever (316) in the fully open position and directing proximal pin (336) of anvil half (304) transversely toward actuating member (356) of translating structure (350). Latching lever (316) is then pivoted from the fully open position (FIG. 13B) to at least the partially-closed position (FIG. 13A) so that locking member (352) captures proximal pin (336) within locking channel (358).

As described above, sloped upper surface (360) of locking member (352) may operate to funnel proximal pin (336) distally toward actuating member (356) as the proximal ends of stapler halves (302, 304) are brought together by the operator. In the event latching lever (316) is not pivoted completely to the fully open position (FIG. 13B) during assembly of halves (302, 304), engagement of proximal pin (336) with sloped upper surface (360) may also provide a camming action that drives locking member (352) proximally to facilitate receipt of proximal pin (336) by locking member (352). Accordingly, translating structure (350) is free to translate proximally independently of the pivoting motion of latching lever (316).

C. Exemplary Alternative Stapler Having User-Engageable Locking Structure

Figure 14A:
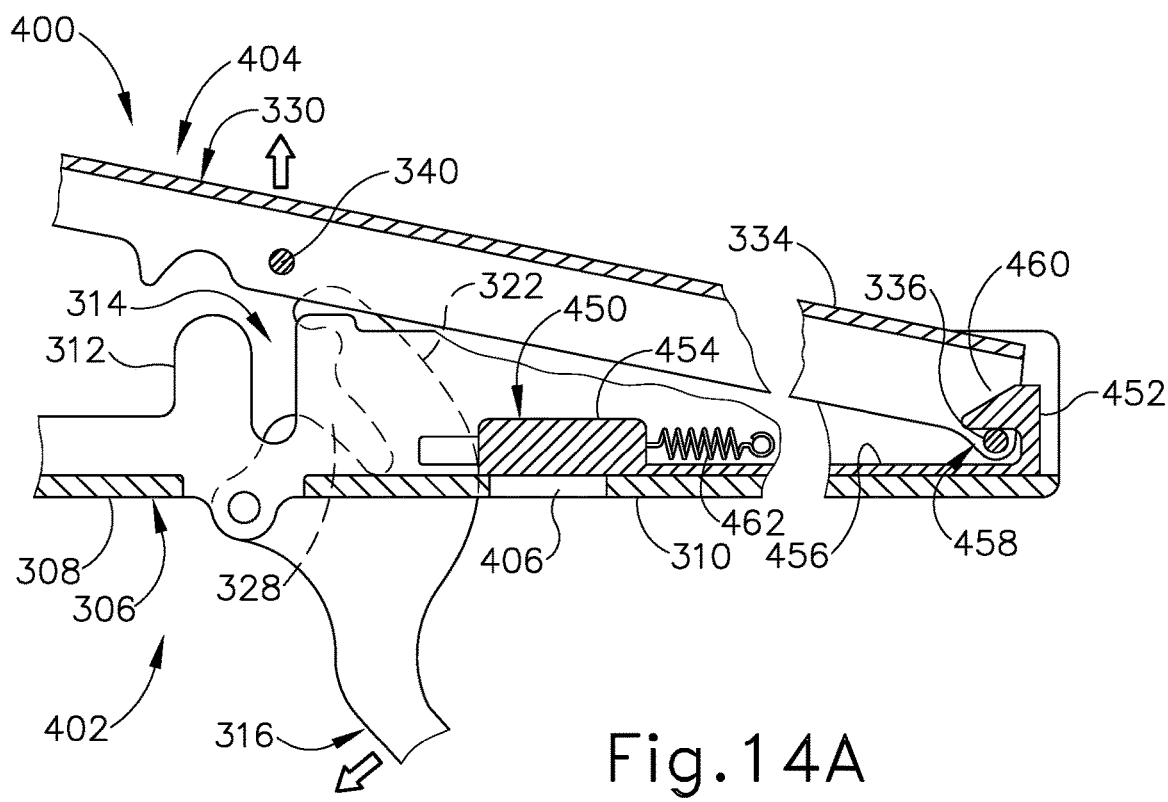
FIG. 14A depicts a cross-sectional side view of another exemplary surgical stapling instrument similar to the instrument of FIG. 12, showing a latching lever of the instrument in phantom in an open position and a proximal locking member of the instrument in a locked position.
Figure 14B:
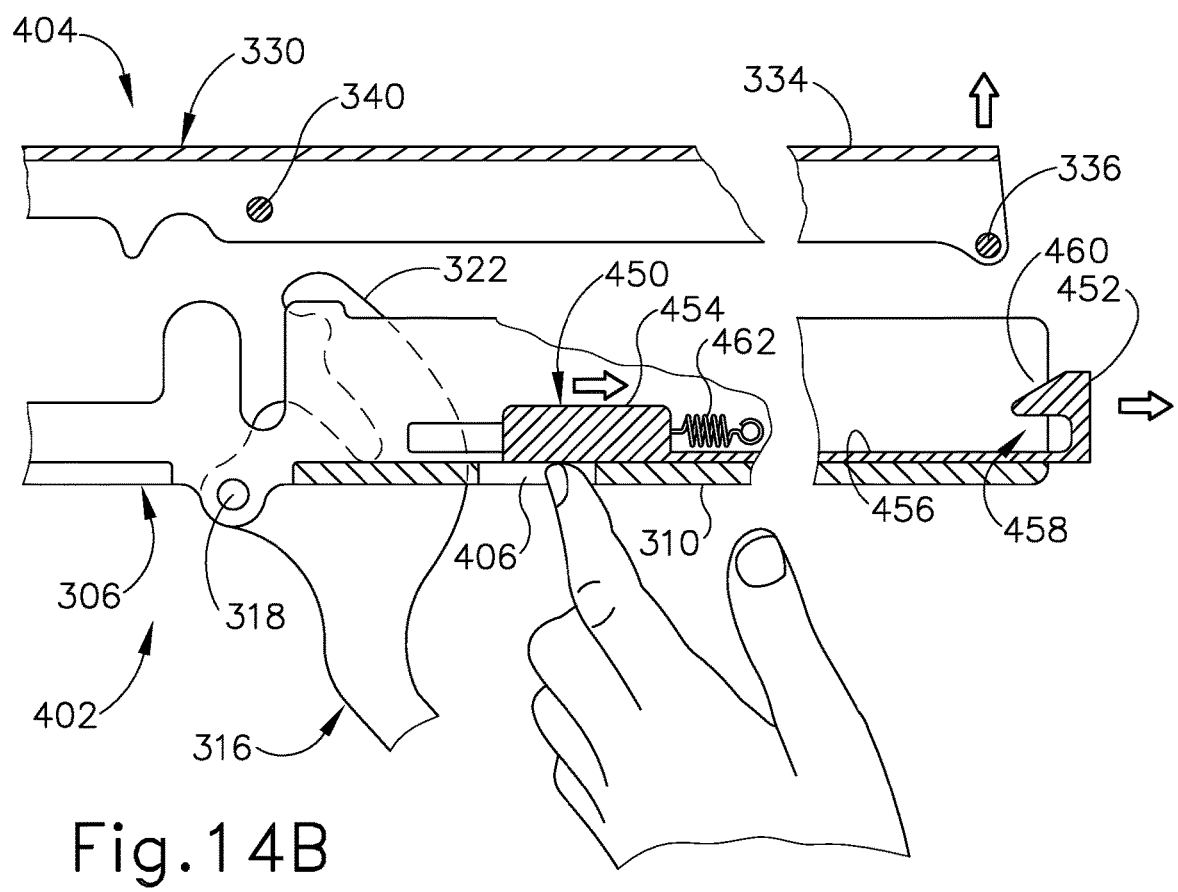
FIG. 14B depicts a cross-sectional side view of the surgical instrument of FIG. 14A, showing the latching lever in phantom in the open position and the proximal locking member in an unlocked position in response to manual actuation by an operator.
Figure 15:
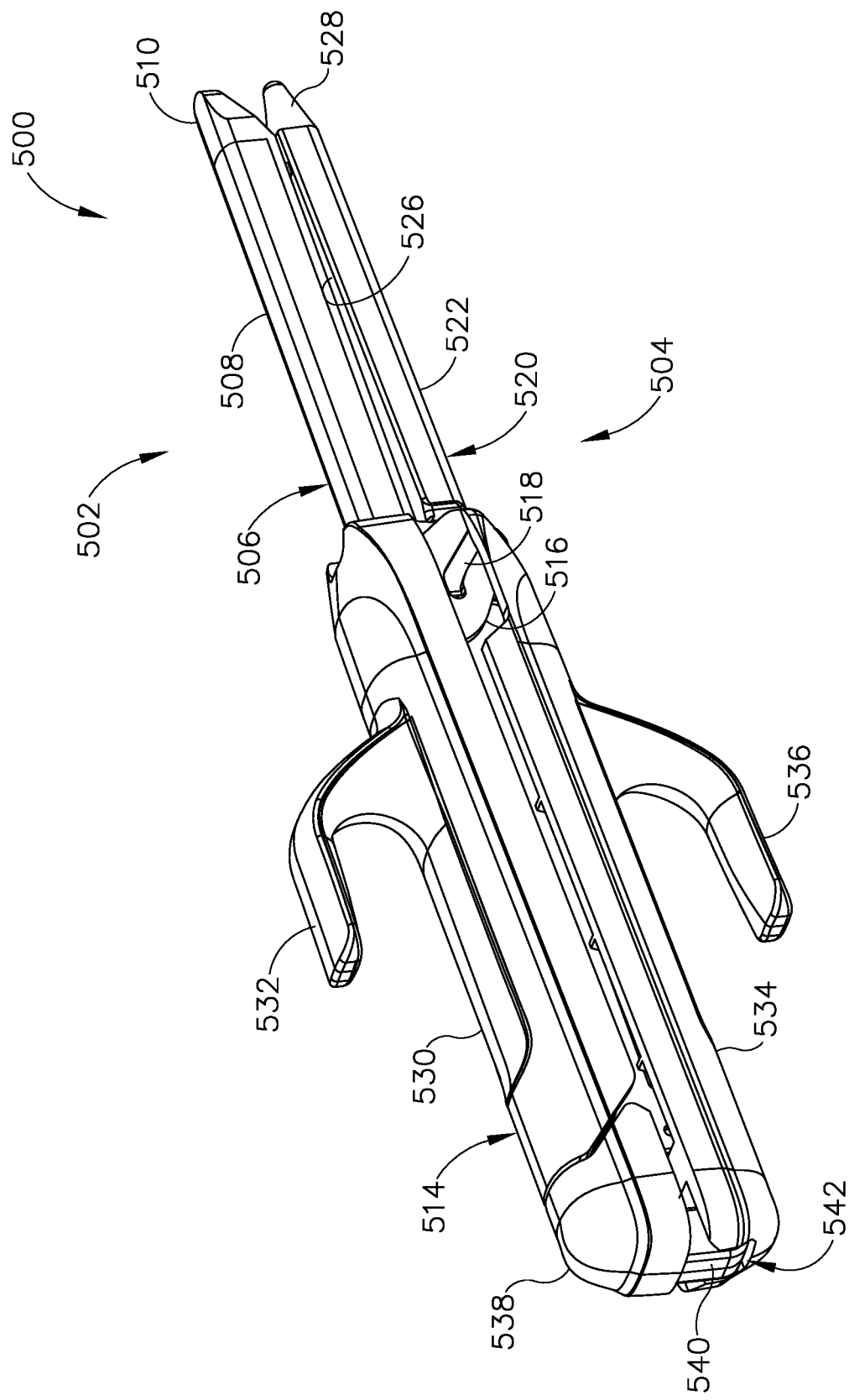
FIG. 15 depicts a perspective view of another exemplary surgical stapling instrument having first and second halves with magnetic alignment members arranged at their proximal ends.

FIGS. 14A and 14B show another exemplary stapler (400) having a cartridge half (402) and an anvil half (404) that are substantially similar to halves (302, 304) of stapler (300) described above, as indicated by use of like reference numerals, except as otherwise described below. In particular, cartridge half (402) includes a translating locking structure (450) that is configured to actuate proximally to the unlocked position in response to manual actuation by an operator rather than in response to opening of latching lever (316), as described below, thereby further protecting against unintended separation of stapler halves (402, 404) during use.

Translating locking structure (450) is similar to translating locking structure (350) described above in that translating locking structure (450) includes a proximal locking member (452), a distal sliding member (454), an elongate actuating member (456) extending therebetween, and a locking channel (458) configured to capture proximal pin (336) of anvil half (304). Additionally, translating structure (450) is resiliently biased distally to its locked position by a resilient member shown in the form of a compression spring (462).

As seen best in FIG. 14A, proximal frame portion (310) of cartridge channel member (306) of stapler (400) includes an opening (406) that is generally aligned with and configured to provide access to sliding member (454) of translating structure (450) when latching lever (316) is in the fully open position. Opening (406) is positioned on proximal frame portion (310) such that arm (320) of latching lever (316) covers and thereby obstructs access to opening (406) when latching lever (316) is in the fully closed position (see FIG. 12). As shown in FIG. 14A, translating structure (450) remains in its distal locked position even when latching lever (316) is pivoted to the fully open position in which lever jaws (322) of cartridge half (402) release latch pin (340) of anvil half (404). This configuration may be achieved through suitable sizing and/or shaping of lever jaws (322) and/or various portions of translating structure (450), such as sliding member (454).

As seen in FIG. 14B, once latching lever (316) is pivoted to the fully open position, an operator may access and insert one or more fingers through opening (406) to contact and manually actuate translating structure (450) proximally to its unlocked position. In the present example, FIG. 14B shows operator contacting a lower surface of sliding member (454), but it will be appreciated that opening (406) may be suitably positioned so that the operator may contact various other portions of translating structure (450). When translating structure (450) reaches its proximal unlocked position, locking member (452) releases proximal pin (336) and the proximal ends of stapler halves (402, 404) may be separated from one another.

As seen in FIG. 14A, translating structure (450) of stapler (400) remains resiliently biased distally toward its locked position by spring (362). Accordingly, translating structure (450) automatically returns to its distal position once the operator removes his or her finger from opening (406). Consequently, during assembly of stapler halves (302, 304), the operator may position translating structure (450) proximally to receive proximal pin (336) by either manually actuating structure (450) proximally via opening (406), or by pressing proximal pin (336) against sloped upper surface (460) of locking member (452) to thereby drive translating structure (450) proximally via camming action, as described above. Though not shown, an opposite configuration of proximal pin (336) and translating structure (450) may be provided in which proximal pin (336) is provided on cartridge half (402) and translating locking structure (450) is provided on anvil half (404).

In other variations of stapler (400), latching lever (316) and translating structure (450) may be configured such that lever jaws (322) couple with and drive translating structure (450) proximally by an initial distance as latching lever (316) is pivoted from the fully closed position (FIG. 12) to the fully open position (FIG. 14A), for example from the partially-closed position (FIG. 13A) to the fully open position (FIG. 14A). This initial distance may be enough to align the user-engageable portion of translating structure (450) with opening (406), while maintaining locking member (452) in locking engagement with proximal pin (336). The operator may then manually actuate translating structure (450) further proximally via opening (406) by the remaining distance required to place translating structure (450) in the unlocked position so that locking member (452) releases proximal pin (336). Accordingly, in such a variation of stapler (400), decoupling of the proximal ends of stapler halves (402, 404) is achieved with a combination of camming action provided by lever jaws (322) and manual actuation provided by the operator.

III. Exemplary Surgical Stapler Having Magnetic Alignment Members

In some instances, it may be desirable to provide the proximal ends of the cartridge half and the anvil half of a surgical stapler with features that facilitate quick alignment and coupling of the proximal ends without complex moving structures. FIGS. 15-19 show an exemplary surgical stapler (500) that includes proximal features configured to provide such functional benefits.

Stapler (500) is substantially similar to staplers (100, 300, 400) described above except as otherwise described below. Stapler (500) includes a cartridge half (502) and an anvil half (504) configured to releasably couple together. Cartridge half (502) includes an elongate cartridge channel member (506) having a distal channel portion (508) configured to receive a staple cartridge (510), and a proximal frame portion (512) configured to slidably house the components of a firing assembly (not shown), which may be similar to firing assembly (200) described above. A latching lever (514) is pivotably coupled to cartridge channel member (506) and includes a pair of opposed jaws (516) each having an elongate slot (518) configured to receive and capture a corresponding latch projection of anvil half (504) when latching lever (514) is in a closed position. Anvil half (504) of stapler (500) includes an elongate anvil channel member (520) having a distal channel portion (522) and a proximal frame portion (524). Distal channel portion (522) supports an anvil surface, shown in the form of anvil plate (526), and a distal tip member (528). In variations of stapler (500), the anvil surface may be integrally formed with distal channel portion (522). In the present example, latching lever (514) includes a first cover (530) having a first handguard (532), and anvil half (504) includes a second cover (534) having a second handguard (536). Additionally, a proximal housing (538) is coupled to a proximal end of cartridge channel member (506).

Figure 16A:
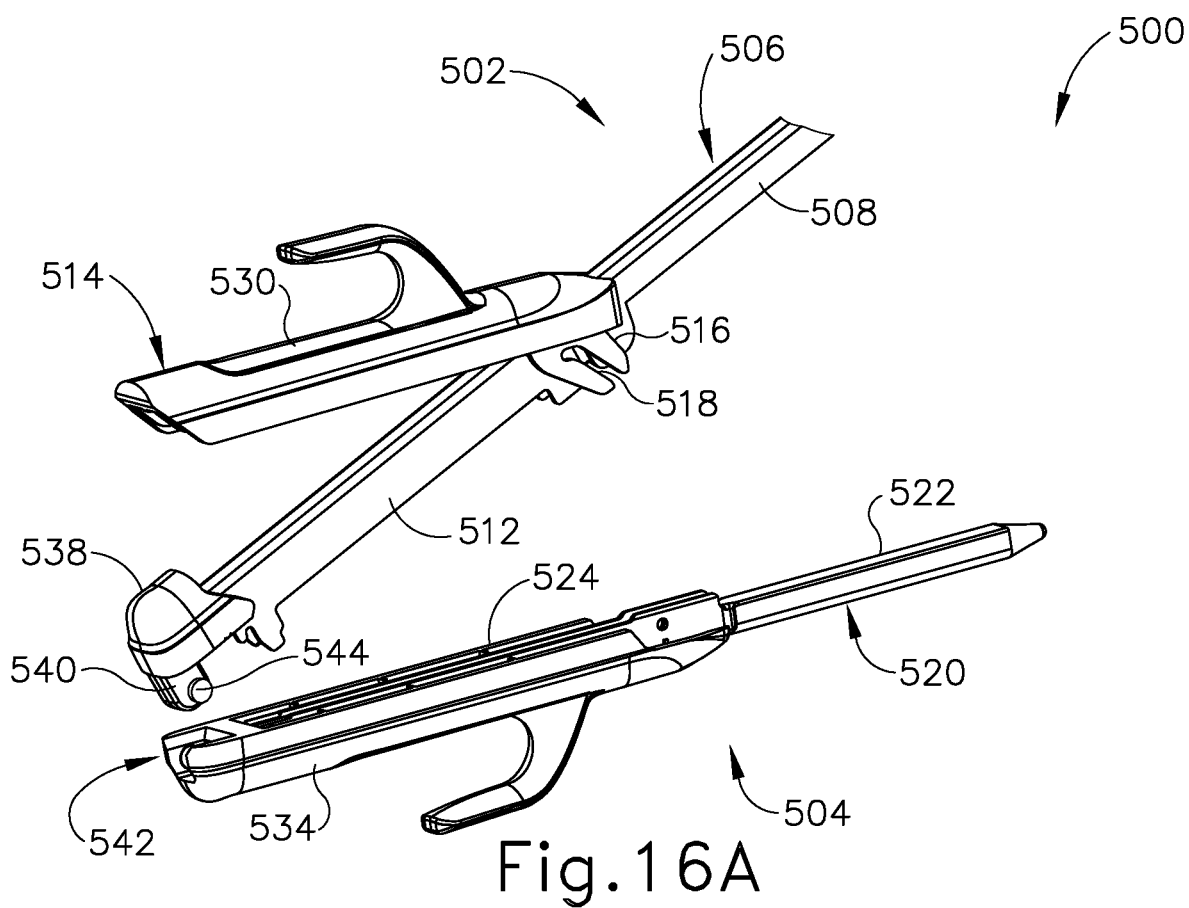
FIG. 16A depicts a perspective view of the surgical stapling instrument of FIG. 15, showing the first and second instrument halves in a decoupled state and with their proximal ends being aligned for coupling together.
Figure 16B:
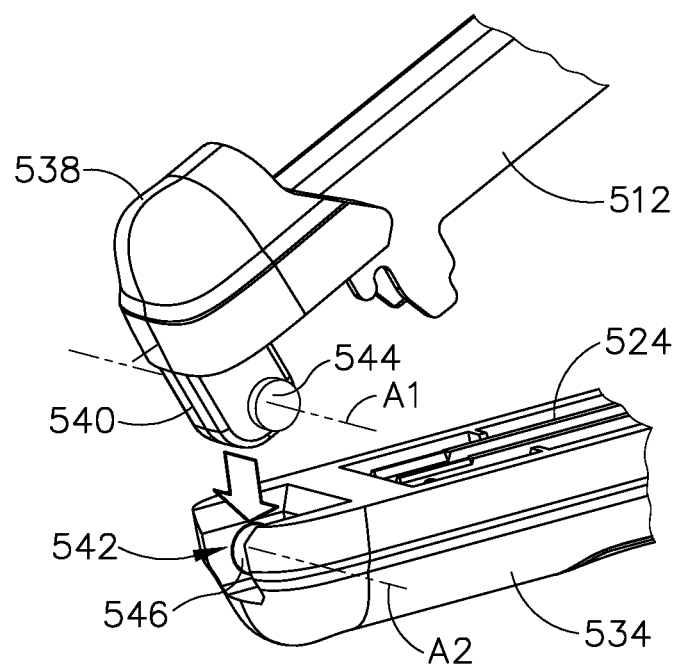
FIG. 16B depicts an enlarged perspective view of the proximal ends of the first and second halves of the surgical stapling instrument of FIG. 15, showing the proximal ends being drawn into alignment with one another by the magnetic alignment members.

As seen best in FIGS. 16A and 16B, a proximal end of cartridge half (502) includes a coupling projection (540) defined by proximal housing (538). A proximal end of anvil half (504) includes a coupling socket (542), defined by anvil cover (534), configured to receive coupling projection (540). Coupling projection (540) includes a pair of first magnetic members (544) arranged on laterally opposed faces of coupling projection (540), and coupling socket (542) includes a pair of second magnetic members (546) arranged on laterally opposed interior walls of socket (542). First magnetic members (544) are configured to magnetically attract second magnetic members (546) to thereby draw coupling projection (540) into coupling socket (542). In this manner, magnetic members (544, 546) enable the proximal ends of stapler halves (502, 504) to self-align and couple together once brought within a certain proximity of one another.

As seen best in FIG. 16B, first magnetic members (544) of cartridge half (502) are arranged along a first lateral axis A1, and second magnetic members (546) of anvil half (504) are arranged along a second lateral axis A2. Magnetic members (544, 546) are configured to draw coupling projection (540) into coupling socket (542), as shown in FIG. 16C, such that lateral axes A1, A2 align coaxially with one another to define a single axis about which cartridge half (502) and anvil half (504) are configured to pivot relative to one another. Magnetic members (544, 546) may be provided with a magnetic strength of any degree suitable to promote self-alignment of the proximal ends of stapler halves (502, 504). The magnetic strength may be sufficient to enable stapler halves (502, 504) to pivot relative to one another about the pivot axis without separating, unless a predetermined transverse separation force is applied to stapler halves (502, 504) by an operator. Though not shown, in some examples stapler (500) may additionally include a mechanism that further secures the proximal ends of stapler halves (502, 504) together once they have self-aligned via magnetic members (544, 546).

FIGS. 17-19 show exemplary features suitable to facilitate separation of the proximal ends of cartridge half (502) and anvil half (504) by overcoming the magnetic attraction forces of magnetic members (544, 546). FIG. 17 shows a first exemplary configuration (550) in which first magnetic members (544) of coupling projection (540) are positioned distally of a longitudinal centerline of coupling projection (540) that extends transversely to a longitudinal axis of cartridge channel member (506). This provides coupling projection (540) with a cam-like configuration that is configured to contact a confronting surface of anvil cover (534) and function as a fulcrum as anvil half (504) is pivoted away from cartridge half (502), thereby separating first magnetic members (544) from second magnetic members (546).

FIG. 18 shows a second exemplary configuration (560) in which coupling projection (540) includes a protrusion (562) on a proximal face thereof. Similar to the cam-like configuration (550) described above, protrusion (562) of configuration (560) is configured to contact a confronting surface of anvil cover (534) and function as a fulcrum as anvil half (504) is pivoted away from cartridge half (502), thereby separating first magnetic members (544) from second magnetic members (546).

FIG. 19 shows a third exemplary configuration (570) in which a proximal end of anvil cover (534) includes a protrusion (572). Protrusion (572) is configured to contact a confronting surface of coupling projection (540) and function as a fulcrum as anvil half (504) is pivoted away from cartridge half (502), thereby separating first magnetic members (544) from second magnetic members (546).

IV. Exemplary Tissue Retaining Features

Surgical procedures in which a surgeon performs a side-by-side anastomosis on first and second tissue structures may be performed with a surgical stapler having first and second stapler halves, such as any of staplers (100, 300, 400) described above. The surgeon positions the first half of the stapler relative to a first tissue structure, and the second stapler half relative to a second, separate tissue structure. While positioning the second stapler half relative to the second tissue structure, it can be difficult to maintain the first stapler half in proper position relative to the first tissue structure. Similarly, it can be difficult to maintain the stapler halves in proper position relative to their respective tissue structures when assembling the stapler halves together for clamping the tissue structures therebetween with the stapler end effector. In some instances, the aid of an assistant in addition to the surgeon may be required.

The exemplary tissue retaining features described below are configured to anchor a tissue structure to a corresponding half of a surgical stapler. This functionality enables a surgeon to more easily and efficiently position the stapler halves relative to tissue structures, and subsequently couple the stapler halves together, while keeping the halves properly positioned relative to their respective tissue structures without the aid of an assistant. Moreover, the exemplary tissue retaining features described below are suitable for use with any of the exemplary staplers described herein, and may be employed in any suitable combination with one another.

A. Tissue Retaining Members Retractable within Stapler Covers

Figure 20:
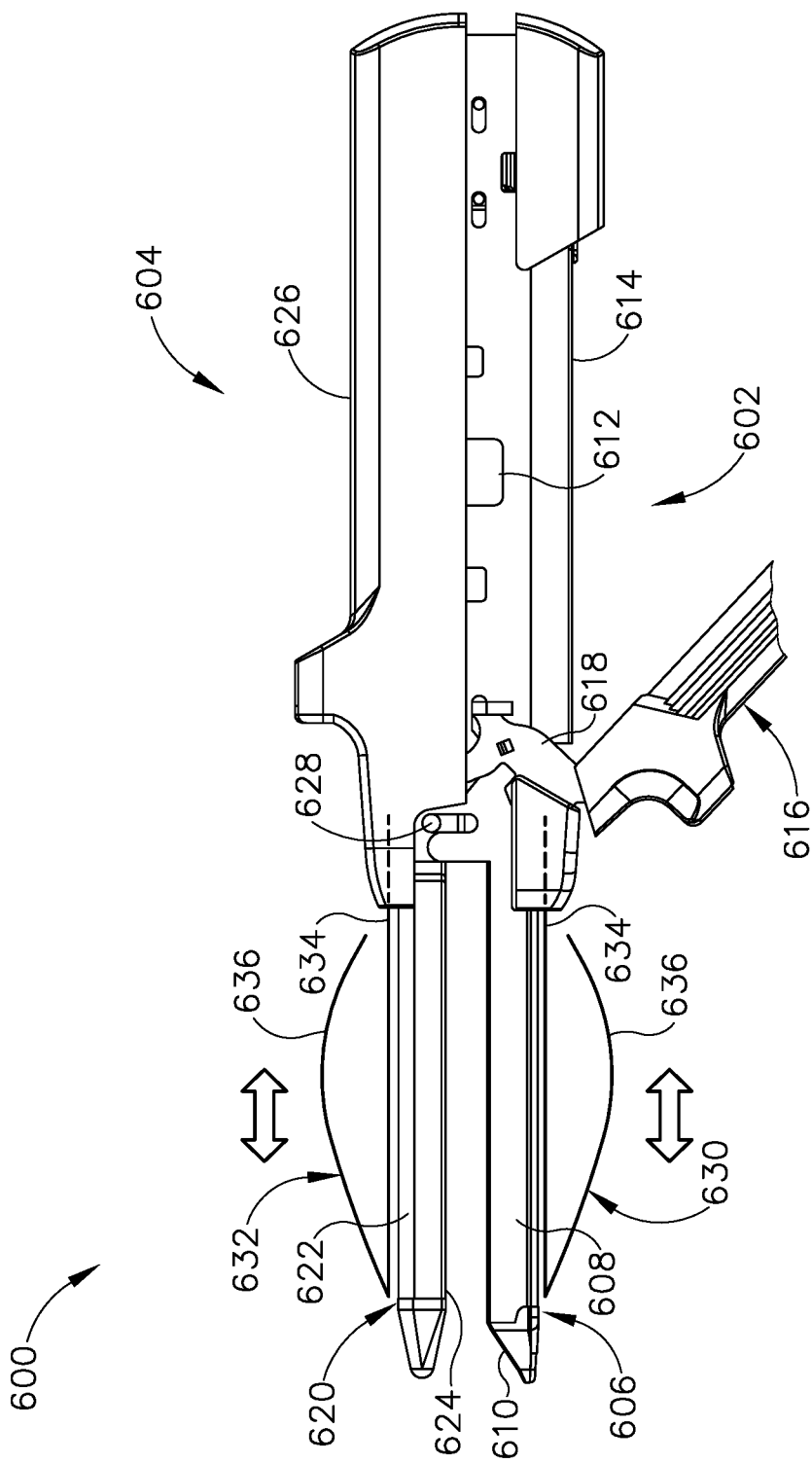
FIG. 20 depicts a side elevational view of another exemplary surgical stapling instrument, showing tissue retaining members of the instrument in extended positions.
Figure 21A:
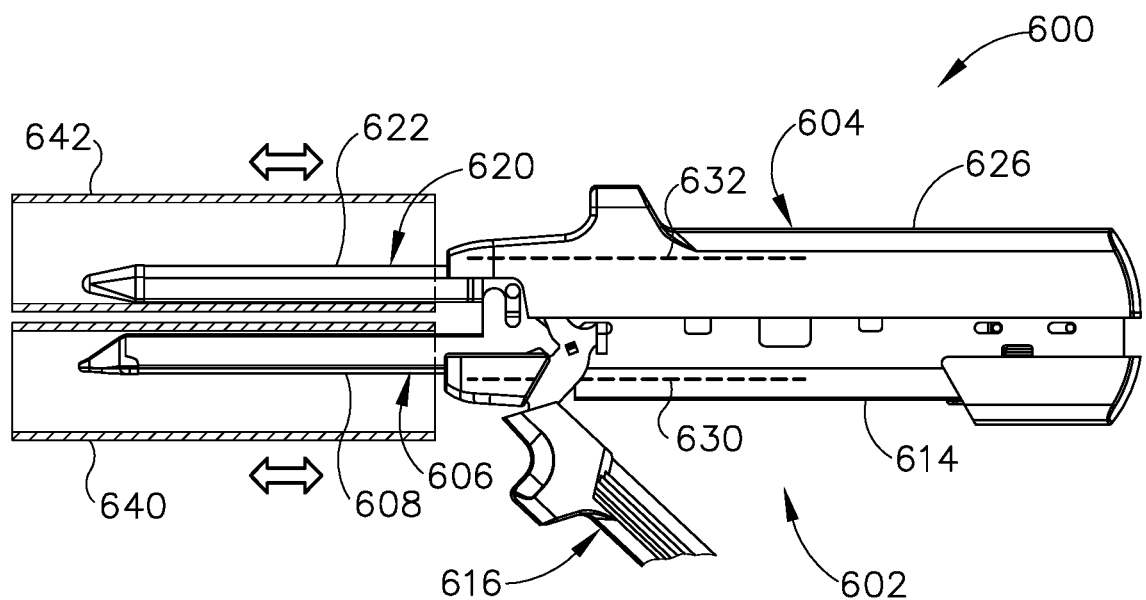
FIG. 21A depicts a side elevational view of the surgical stapling instrument of FIG. 20, showing distal portions of first and second halves of the instrument positioned within openings of respective tissue structures, and showing the tissue retaining members in retracted positions.
Figure 21B:
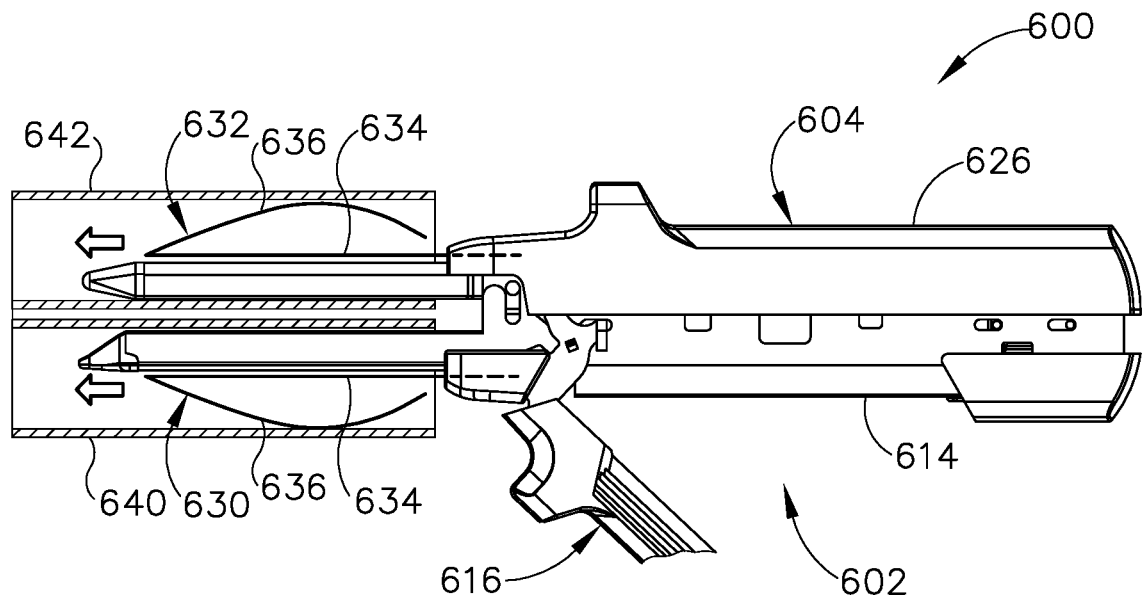
FIG. 21B depicts a side elevational view of the surgical stapling instrument of FIG. 20, showing the tissue retaining members in the extended positions within the respective tissue structures.

FIGS. 20-21B show another exemplary surgical stapler (600) that is similar to staplers (100, 300, 400) described above in that stapler (600) includes a cartridge half (602) and an anvil half (604) configured to releasably couple together. Cartridge half (602) includes an elongate cartridge channel member (606) having a distal channel portion (608) configured to receive a staple cartridge (610), and a proximal frame portion (612) configured to slidably house components of a firing assembly (not shown), which may be similar to firing assembly (200) described above. Proximal frame portion (612) is shrouded by a first frame cover (614). Cartridge half (602) further includes a latching lever (616) pivotably coupled to cartridge channel member (606) and having a pair of jaws (618).

Anvil half (604) includes an elongate anvil channel member (620) having a distal channel portion (622) that supports an anvil surface, shown in the form of anvil plate (624), and a proximal frame portion (not shown) shrouded by a second frame cover (626). In variations of stapler (600), the anvil surface may be integrally formed with distal channel portion (622). Anvil half (604) further includes a latch pin (628) supported by anvil channel member (620) at a medial location between the proximal frame portion and distal frame portion (622). Latching lever (616) of cartridge half (602) is selectively pivotable between an open position (shown) and a closed position (not shown) for capturing opposed ends of latch pin (628) with jaws (618) and thereby locking anvil half (604) against cartridge half (602) to clamp tissue between staple cartridge (610) and anvil plate (624).

Stapler (600) further includes a pair of retractable tissue retaining members (630, 632). First retractable tissue retaining member (630) is slidably coupled to cartridge half (602), and is configured to slidably retract proximally within and extend distally from first frame cover (614). Second retractable tissue retaining (632) is slidably coupled to anvil half (604), and is configured to slidably retract proximally within and extend distally from second frame cover (626). As shown in FIG. 20, each retractable tissue retaining member (630, 632) includes a straight base leg (634) and a convexly curved spring leg (636) coupled to a distal end of base leg (634). Spring leg (636) includes a free proximal end and is configured to resiliently flex inwardly toward base leg (634) when engaging an inner surface of a respective tissue structure, as described below.

As seen in FIGS. 21A and 21B, each tissue retaining member (630, 632) is configured to translate longitudinally between a proximal retracted position (FIG. 21A) and a distal extended position (FIG. 21B). In the proximal retracted position, each retaining member (630, 632) is at least partially (e.g., fully) housed within the respective frame cover (614, 626). In the distal extended position, each retaining member (630, 632) is exposed from its respective frame cover (614, 626) and overlies the distal channel portion (608, 622) of the respective channel member (606, 620).

In use, retractable tissue retaining members (630, 632) are first placed in their proximal retracted positions, as shown in FIG. 21A. The distal portion of cartridge half (602) is then positioned within the opening of a first tissue structure (640) such that an inner surface of first tissue structure (640) is draped across a deck of staple cartridge (610). Independently, the distal portion of anvil half (604) is positioned with the opening of a second tissue structure (642) such that an inner surface of second tissue structure (642) is draped across anvil plate (624). Then, before or after assembling together the two stapler halves (602, 604), retractable tissue retaining members (630, 632) are actuated distally to their extended positions, as shown in FIG. 21B. Actuation of retaining members (630, 632) may be performed using one or more user-engageable actuation features (not shown), such as one or more knobs, wheels, or other such actuation mechanisms that will be readily apparent to those of ordinary skill in the art.

As seen in FIG. 21B, as tissue retaining members (630, 632) extend distally into tissue structures (640, 642), curved spring legs (636) engage the inner surfaces of tissue structures (640, 642). Spring legs (636) may be suitably shaped such that a maximum distance measured between spring legs (636) in their relaxed state and the respective staple deck of staple cartridge (610) or anvil plate (624) is greater than an inner diameter of tissue structures (640, 642). Consequently, as each tissue retaining member (630, 632) is extended distally into its respective tissue structure (640, 642), its spring leg (636) resiliently deflects inwardly toward base leg (634), thereby exerting an outwardly directed spring force on the inner surface of the respective tissue structure (640, 642). This outwardly directed spring force functions to retain tissue structure (640, 642) in place relative to the respective stapler half (602, 604) via friction. Accordingly, tissue retaining members (630, 632) aid in keeping tissue structures (640, 642) securely coupled with stapler halves (602, 604) during a surgical procedure, such that an operator need not hold tissue structures (640, 642) to stapler halves (602, 604) by hand during assembly of stapler halves (602, 604), and/or during subsequent stapling and cutting of tissue structures (640, 642). This allows the operator to use his or her free hand to manipulate other features of stapler (600) or anatomical structures of the patient as needed, without requiring an assistant.

B. Tissue Retaining Members Fixed at Distal Portion of Channel Member

Figure 22:
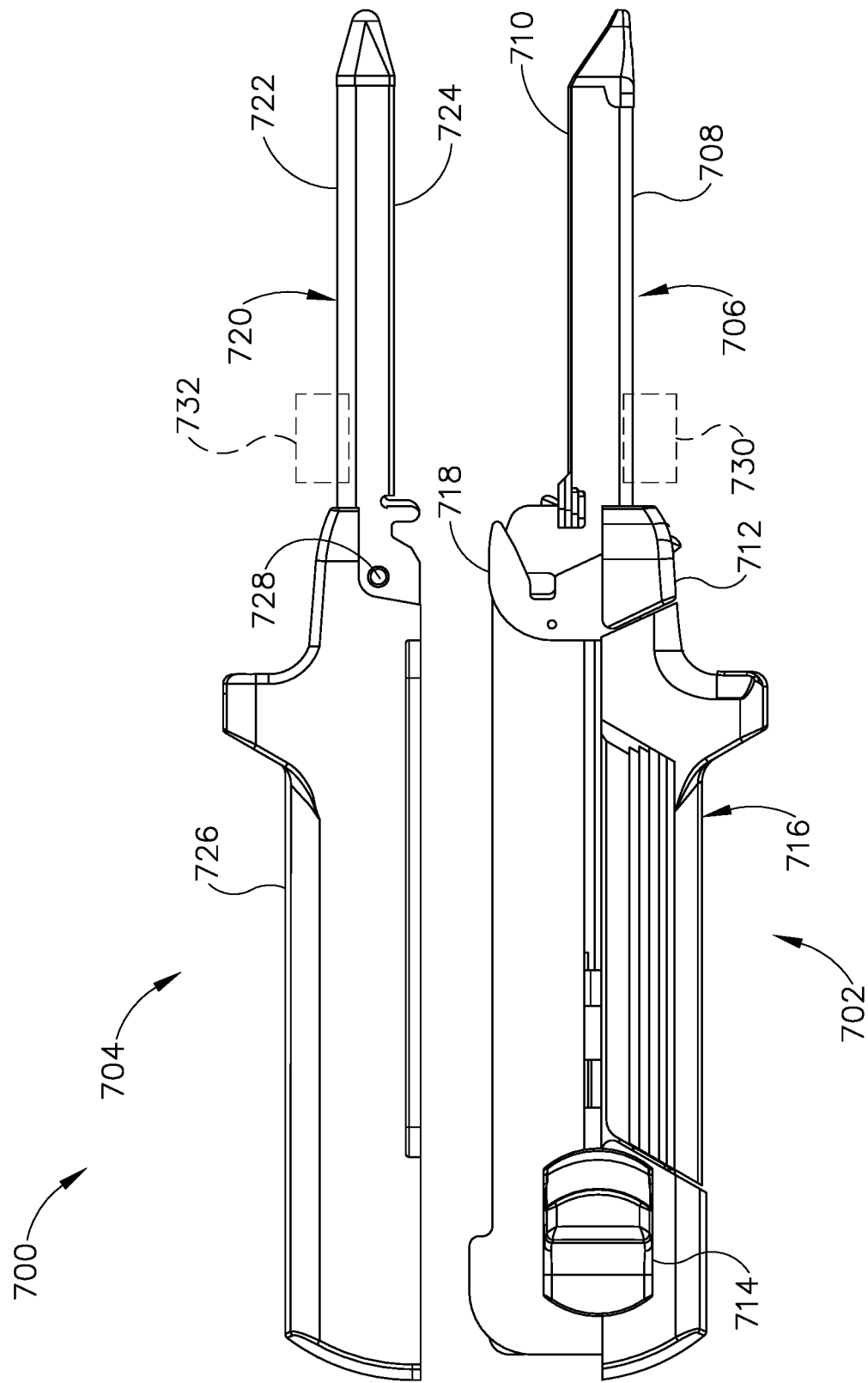
FIG. 22 depicts a side elevational view of another exemplary surgical stapling instrument, schematically showing a tissue retaining feature on a distal portion of each of the instrument halves.

FIG. 22 shows another exemplary surgical stapler (700) that is similar to staplers (100, 300, 400, 600) described above in that stapler (700) includes a cartridge half (702) and an anvil half (704) configured to releasably couple together. Cartridge half (702) includes an elongate cartridge channel member (706) having a distal channel portion (708) configured to receive a staple cartridge (710), and a proximal frame portion (not shown) shrouded by a first frame cover (712). The proximal frame portion of cartridge channel member (706) is configured to slidably house components of a firing assembly that is generally similar to firing assembly (200) described above and includes a translatable firing knob (714). Cartridge half (702) further includes a latching lever (716) pivotably coupled to cartridge channel member (706) and having a pair of jaws (718).

Anvil half (704) includes an elongate anvil channel member (720) having a distal channel portion (722) that supports an anvil surface, shown in the form of anvil plate (724), and a proximal frame portion (not shown) shrouded by a second frame cover (726). In variations of stapler (700), the anvil surface may be integrally formed with distal channel portion (722). Anvil half (704) further includes a latch pin (728) supported by anvil channel member (720) at a medial location between the proximal frame portion and distal frame portion (722). Latching lever (716) of cartridge half (702) is selectively pivotable between an open position and a closed position for capturing opposed ends of latch pin (728) with jaws (718) and thereby locking anvil half (704) against cartridge half (702) to clamp tissue between staple cartridge (710) and anvil plate (724).

As shown schematically in FIG. 22, a first tissue retaining feature (730) is arranged at a proximal end of distal channel portion (708) of cartridge channel member (706). Similarly, a second tissue retaining feature (732) is arranged at a proximal end of distal channel portion (722) of anvil channel member (720). Each tissue retaining feature (730, 732) is configured to anchor a respective tissue structure, such as tissue structures (640, 642) described above, to a respective half (702, 704) of stapler (700).

FIGS. 23-29, described below, show exemplary configurations of first and second tissue retaining features (730, 732). In some instances, first and second tissue retaining features (730, 732) may be provided with the same configuration. In other instances, first and second tissue retaining features (730, 732) may be provided with different configurations. In that regard, it will be appreciated that any suitable combination of the exemplary configurations of tissue retaining features (730, 732) described below may be provided on the first and second halves of a surgical stapler, such as halves (702, 704) of stapler (700).

FIG. 23 shows a first exemplary configuration of tissue retaining feature (730, 732) in the form of a rigid bulb element (740) coupled to a proximal end of distal channel portion (708, 722) of channel member (706, 720). Rigid bulb element (740) is configured to frictionally engage the inner surface of a tissue structure mounted to stapler half (702, 704).

FIG. 24 shows a second exemplary configuration of tissue retaining feature (730, 732) in the form of an expandable bulb element (742) coupled to a proximal end of distal channel portion (708, 722) of channel member (706, 720). In one example, expandable bulb element (742) may be inflated with a fluid provided by an inflation fluid source (not shown) operatively coupled to expandable bulb element (742). For instance, distal channel portion (708, 722) may be inserted into the opening of a tissue structure with expandable bulb element (742) in a deflated state, and then bulb element (742) may be inflated to thereby frictionally engage an inner surface of the tissue structure.

FIG. 25 shows a third exemplary configuration of tissue retaining feature (730, 732) in the form of radially projecting threads (744) provided on the exterior surface of a proximal end of distal channel portion (708, 722) of channel member (706, 720). Similar to rigid bulb element (740) and expandable bulb element (742) described above, threads (744) are configured to frictionally engage the inner surface of a tissue structure mounted to stapler half (702, 704).

FIG. 26 shows a fourth exemplary configuration of tissue retaining feature (730, 732) in the form of a pair of angular projections (746) extending outwardly from opposed sidewalls of a proximal end of distal channel portion (708, 722) of channel member (706, 720). In the present example, each angular projection (746) flares outwardly in a proximal direction and is configured to frictionally engage the inner surface of a tissue structure, for example in a manner similar to a barb. In some examples, angular projections (746) may be stamped outwardly from the material forming the lateral sidewalls of distal channel portion (708, 722).

Figure 27:
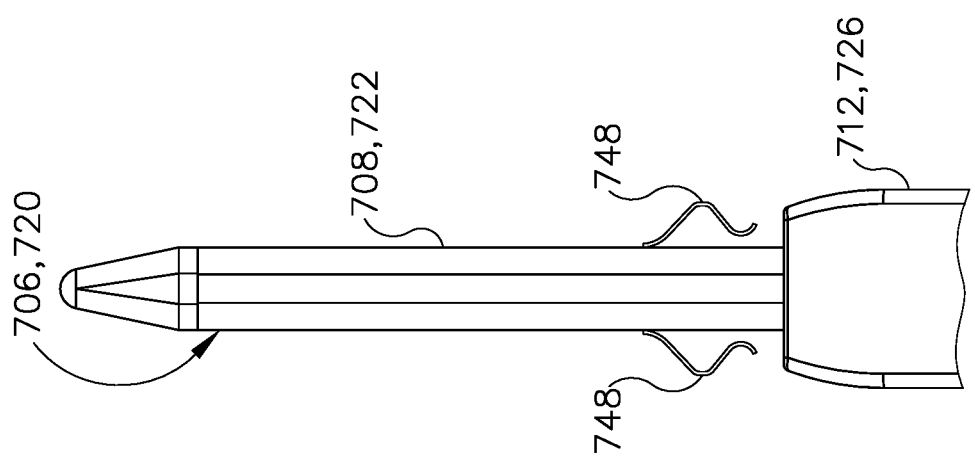
FIG. 27 depicts a bottom elevational view of a distal portion of a half of the surgical stapling instrument of FIG. 22, showing the instrument half with the respective tissue retaining feature according to a fifth exemplary configuration.

FIG. 27 shows a fifth exemplary configuration of tissue retaining feature (730, 732) in the form of a pair of convexly curved spring legs (748) coupled to laterally opposed sidewalls of a proximal end of distal channel portion (708, 722) of channel member (706, 720). Each spring leg (748) is configured to engage an inner surface of a tissue structure and resiliently deflect inwardly in a manner similar to spring legs (636) of retractable tissue retaining members (630, 632) described above.

Figure 28:
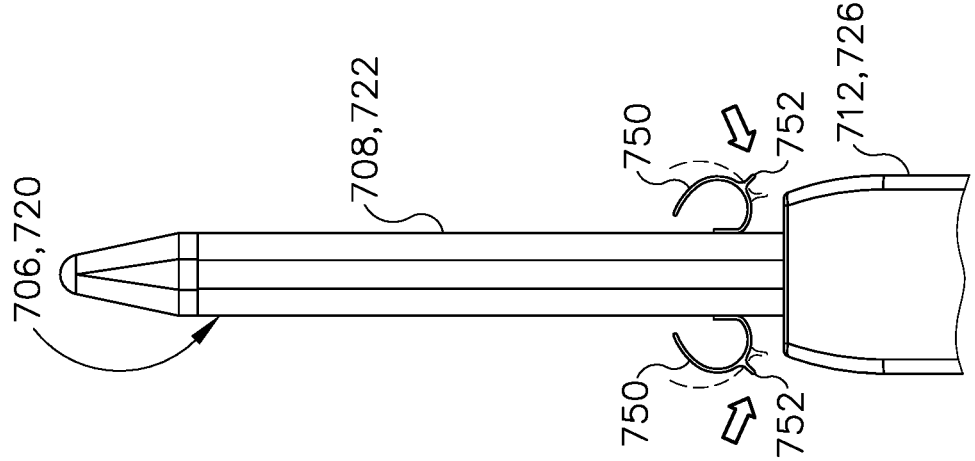
FIG. 28 depicts a bottom elevational view of a distal portion of a half of the surgical stapling instrument of FIG. 22, showing the instrument half with the respective tissue retaining feature according to a sixth exemplary configuration.

FIG. 28 shows a sixth exemplary configuration of tissue retaining feature (730, 732) in the form of a pair of actuatable spring clips (750) coupled to laterally opposed sidewalls of a proximal end of distal channel portion (708, 722) of channel member (706, 720). Unlike tissue retaining features (740, 742, 744, 746, 748) described above, actuatable spring clips (750) are configured to engage an outer surface of a tissue structure. In the present example, each clip (750) is generally C-shaped and includes a proximal protrusion (752) configured to be depressed by an operator to resiliently deflect a free distal end of spring clip (750) in a direction away from distal channel portion (708, 722) so the wall of a tissue structure may be received beneath the distal end. Once the tissue structure is suitably positioned, the operator releases protrusions (752) to allow the free terminal ends of spring clips (750) to engage and compress an outer surface of the tissue structure via spring force.

Figure 29:
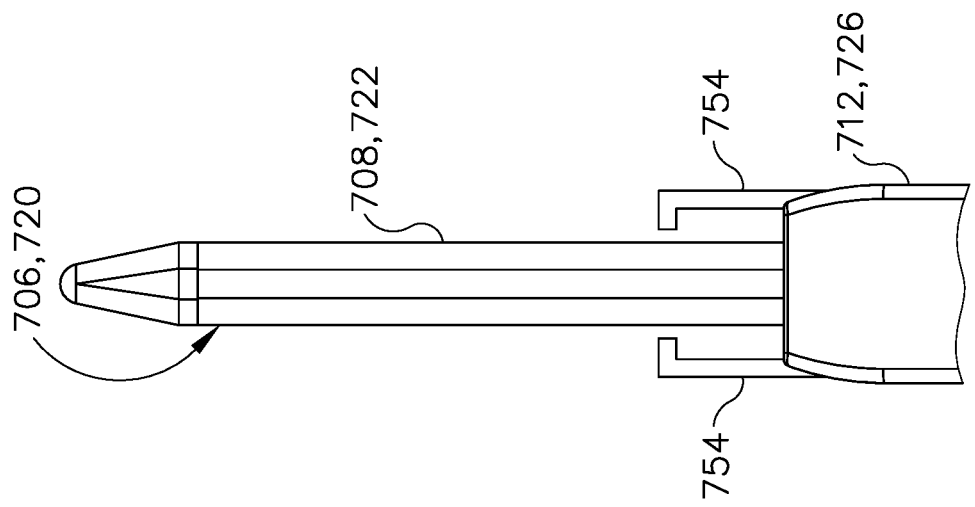
FIG. 29 depicts a bottom elevational view of a distal portion of a half of the surgical stapling instrument of FIG. 22, showing the instrument half with the respective tissue retaining feature according to a seventh exemplary configuration.

FIG. 29 shows a seventh exemplary configuration of tissue retaining feature (730, 732) in the form of a pair of clips (754) coupled to laterally opposed distal ends of frame cover (712, 726). Similar to spring clips (750) described above, clips (754) are configured to engage an outer surface of a tissue structure mounted to stapler half (702, 704). In the present example, each spring clip (754) is generally L-shaped and includes a proximal end coupled to a distal end of frame cover (712, 726), and a free distal end that overlies distal channel portion (708, 722). In some examples, the proximal ends of clips (754) may be fixed to frame cover (712, 726), and the body of each clip (754) may be resilient or rigid. In other examples, the proximal ends of clips (754) may be movably coupled to frame cover (712, 726) such that clips (754) may be articulated relative to frame cover (712, 726) between two or more positions.

C. Tissue Retaining Clips on Staple Cartridge

Figure 30:
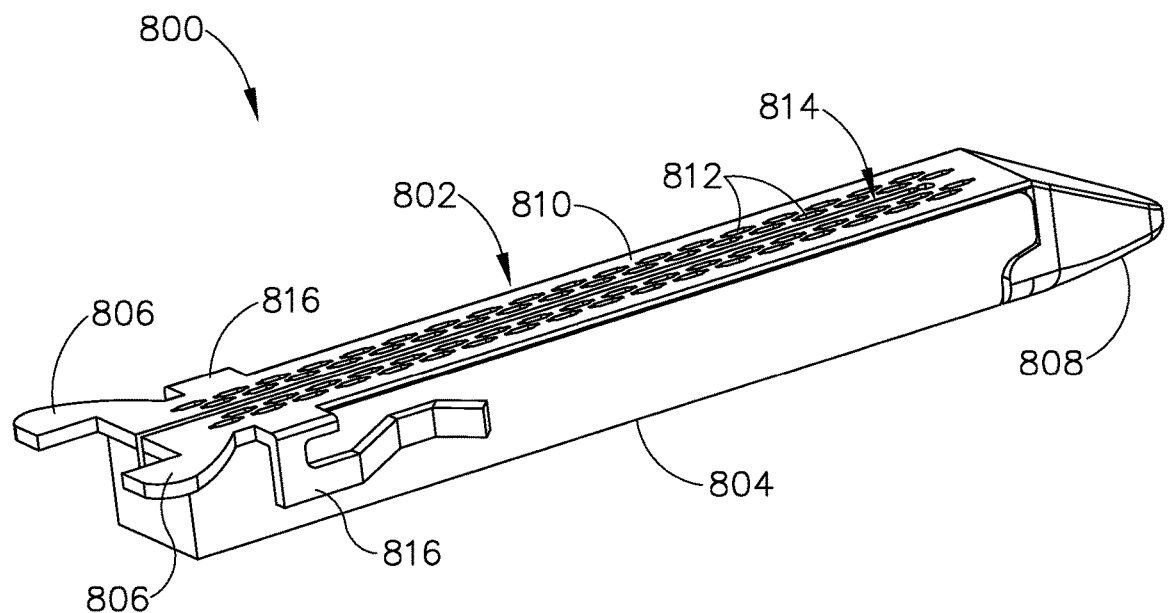
FIG. 30 depicts a perspective view of an exemplary staple cartridge having a tissue retaining feature.
Figure 31:
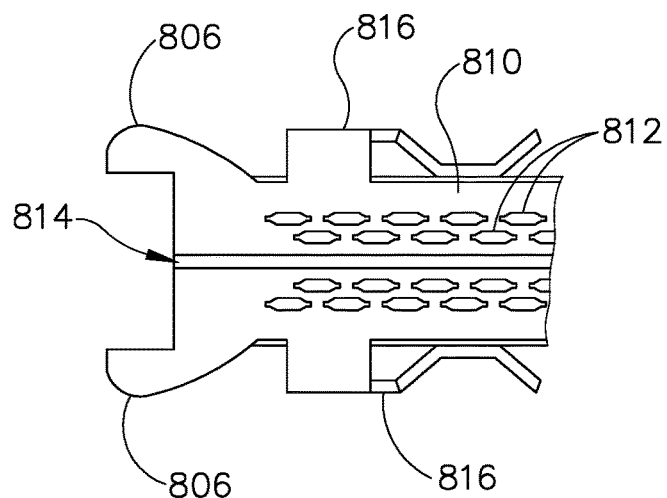
FIG. 31 depicts a top elevational view of the staple cartridge of FIG. 30, showing additional details of the tissue retaining feature.

In some instances, it may be desirable to incorporate a tissue retaining feature on the staple cartridge of a surgical stapler, rather than on other components of the cartridge half of a stapler. FIGS. 30 and 31 show a staple cartridge (800) having a tissue retaining feature of an exemplary configuration, described in greater detail below. Staple cartridge (800) is similar to staple cartridge (150) described above except as otherwise described below.

Staple cartridge (800) includes a cartridge body (802) and a pan (804) (or "tray") coupled to and extending longitudinally along an underside of cartridge body (802). Cartridge body (802) includes a proximal end having a pair of proximally projecting coupling elements (806) configured to facilitate coupling of staple cartridge (800) to a cartridge channel member, and a distal end defining a tapered nose (808). An upper side of cartridge body (802) defines a staple deck (810) having a plurality of staple openings (812) configured to receive staples and respective staple drivers (not shown) similar to staple drivers (168) described above.

Cartridge body (802) further includes a longitudinally extending slot (814) configured to slidably receive a translating member (not shown) of a stapler firing assembly, which may be similar to sled (160) of firing assembly (200) described above. Though not shown, stapler cartridge (800) may further include a sled assembly housing similar to sled assembly housing (170) described above. Staple cartridge (800) is operable to interact with a firing assembly (not shown) similar to firing assembly (200) described above to eject staples upwardly through staple deck (810) and overlying tissue, and against an anvil surface.

In the present example, staple cartridge (800) includes a tissue retaining feature in the form of a pair of spring clips (816) coupled to a proximal end of cartridge body (802) and extending distally along the opposed lateral sides of staple cartridge (800). As seen in FIG. 30, the proximal ends of clips (816) are formed flush with staple deck (810) and extend perpendicularly downward from staple deck (810) before projecting distally. Each clip (816) is configured to resiliently flex and clamp against an outer surface of a tissue structure mounted to the cartridge half of a surgical stapler in which staple cartridge (800) is received.

Figure 32:
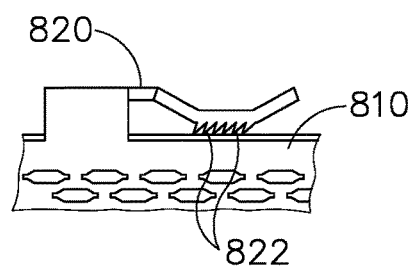
FIG. 32 depicts a top elevational view of a tissue retaining feature according to another exemplary variation suitable for use with the staple cartridge of FIG. 30.

FIG. 32 shows exemplary alternative spring clips (820) that are suitable for use with staple cartridge (800). Clips (820) are substantially similar to clips (816) described above, except that each clip (820) includes a plurality of teeth (822) disposed longitudinally along an inner surface of clip (820) that confronts a lateral side of staple cartridge (800). Teeth (822) are configured to at least partially embed within the outer surface of a tissue structure and thereby enhance retention of the tissue structure relative to the cartridge half of a surgical stapler.

D. Exposed Staple Legs of Staple Cartridge

Figure 33:
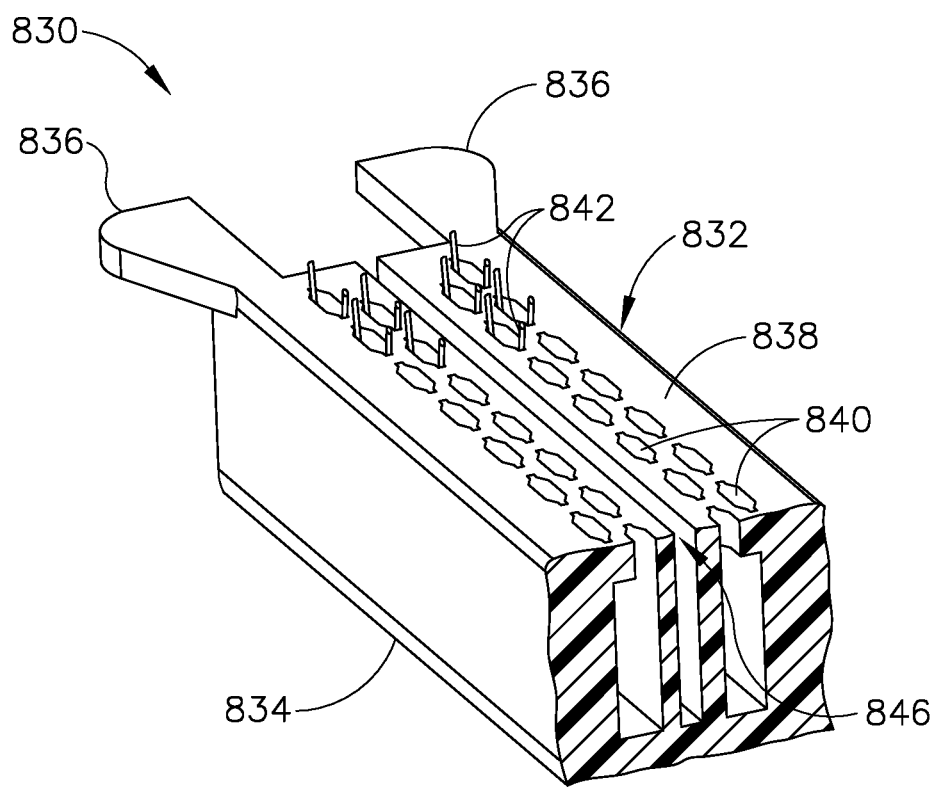
FIG. 33 depicts a perspective view of a proximal portion of another exemplary staple cartridge having a tissue retaining feature.
Figure 34:
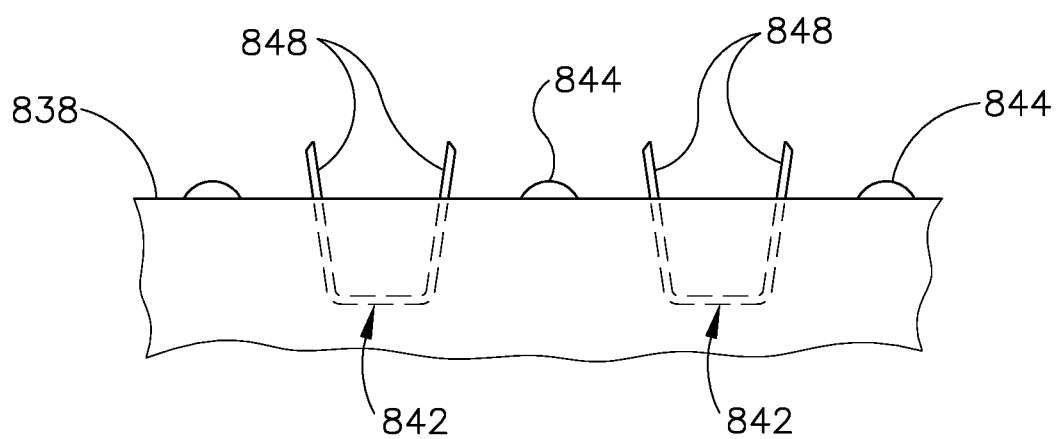
FIG. 34 depicts a schematic side elevational view of a portion of the staple cartridge of FIG. 33 and its tissue retaining feature.

FIGS. 33 and 34 show another staple cartridge (830) having a tissue retaining feature of another exemplary configuration, described in greater detail below. Staple cartridge (830) is similar to staple cartridges (150, 800) described above in that staple cartridge (830) includes a cartridge body (832) and a pan (834) coupled to cartridge body (832). Cartridge body (832) includes a proximal end having a pair of proximally projecting coupling elements (836), and a distal end defining a tapered nose (not shown). Cartridge body (832) further includes a staple deck (838) having a plurality of staple openings (840) that receive a corresponding plurality of staples (842) and respective staple drivers (not shown) similar to staple drivers (168) described above. As shown in FIG. 34, staple deck (838) may include a plurality of protrusions (844) configured to enhance retention of a tissue structure (not shown) clamped against staple deck (838). Cartridge body (832) further includes a longitudinally extending slot (846) configured to slidably receive a translating member (not shown) of a stapler firing assembly, which may be similar to sled (160) of firing assembly (200) described above.

FIGS. 33 and 34 show staple cartridge (830) in a pre-fired state in which staples (842) are positioned within staple openings (840) such that staple legs (848) of staples (842) protrude upwardly through staple openings (840) beyond staple deck (838). These exposed staple legs (848) are configured to at least partially embed within tissue overlaid on staple deck (838), and thereby retain the tissue relative to staple cartridge (830). Thus, these exposed staple legs (848) operate to anchor a tissue structure relative to staple cartridge (830) and the cartridge half in which cartridge (830) is received. In the present example, only a proximal grouping of staples (842) are positioned within staple openings (840) such that their staple legs (848) are exposed beyond staple deck (838) in the pre-fired state of staple cartridge (830). In other examples, any selected quantity and arrangement of staples (842) of cartridge (830) may be positioned such that their legs (848) are exposed when cartridge (830) is in the pre-fired state, so as to function as a tissue retaining feature.

E. Cutaway Barb on Staple Cartridge

Figure 35:
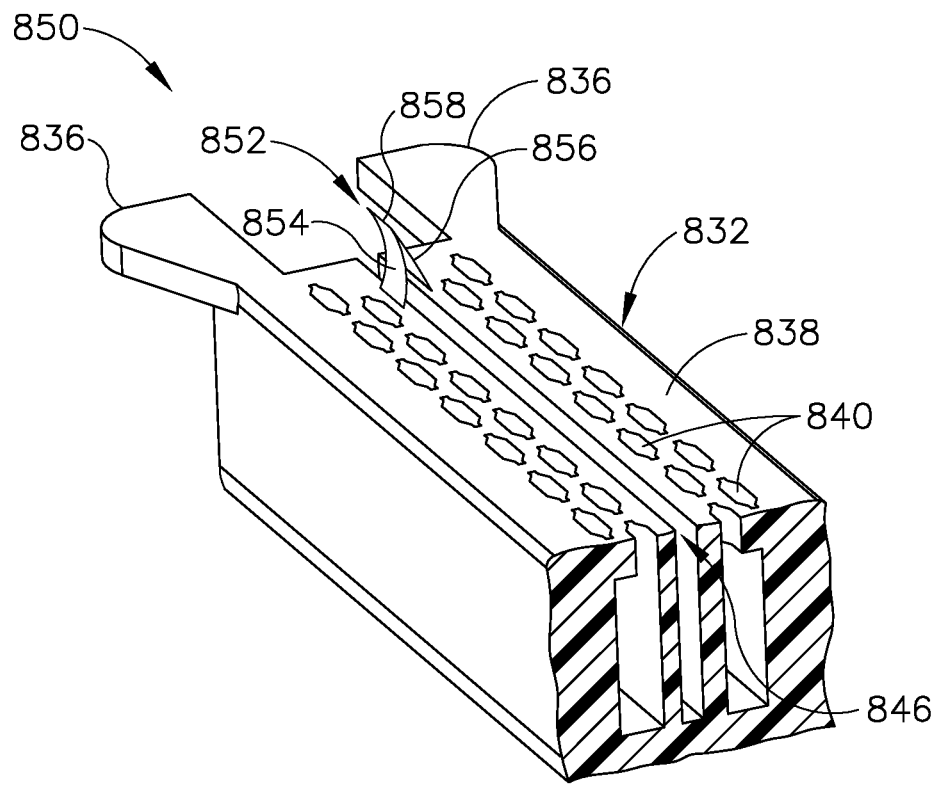
FIG. 35 depicts a perspective view of a proximal portion of another exemplary staple cartridge having a tissue retaining feature.
Figure 36A:
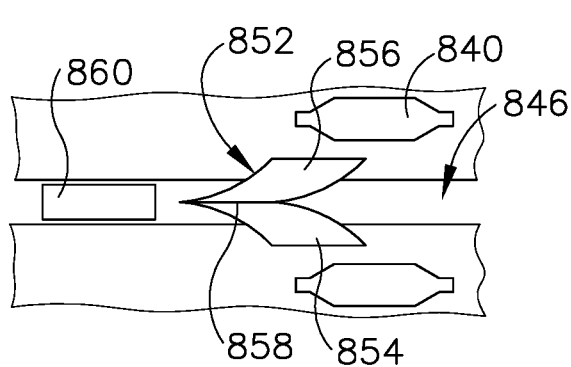
FIG. 36A depicts a schematic top elevational view of the staple cartridge of FIG. 35, showing the tissue retaining feature in a first state in which the feature is configured to retain tissue.
Figure 36B:
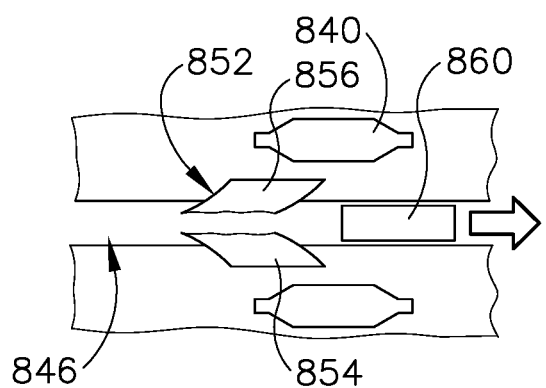
FIG. 36B depicts a schematic top elevational view of the staple cartridge of FIG. 36A, showing the tissue retaining feature in a second state in which the feature is configured to release tissue.

FIGS. 35-36B show another staple cartridge (850) having a tissue retaining feature of another exemplary configuration. Staple cartridge (850) is substantially similar to staple cartridge (830) described above, as indicated by use of like reference numerals, except as otherwise described below. In particular, staple cartridge (850) includes a tissue retaining feature in the form of a cutaway barb (852) coupled to staple deck (838).

In the present example, cutaway barb (852) is arranged at a proximal end portion of staple deck (838) and includes first and second barb halves (854, 856) that couple together at an upward tip (858). Lower base ends of barb halves (854, 856) are coupled to staple deck (838) on laterally opposed sides of longitudinal slot (846), and barb halves (854, 856) extend upwardly and toward one another such that upward tip (858) is positioned generally above longitudinal slot (846), as seen in FIG. 36A. Upward tip (858) is in the form of a frangible connection or any other connection configured to be severed by a cutting member that translates distally through longitudinal slot (846), as described below. Additionally, cutaway barb (852) sweeps proximally to enable upward tip (858) to at least partially embed within tissue. Cutaway barb (852) may be formed with a height sufficient to promote such gripping of tissue without interfering with the anvil surface of the opposing half of a stapler with which staple cartridge (850) is used. Moreover, while only one cutaway barb (852) is shown in the present example, two or more cutaway barbs (852) may be provided in other examples, and such barbs (852) may be arranged longitudinally at any suitable locations along longitudinal slot (846).

FIGS. 35 and 36A show cutaway barb (852) in an intact state prior to firing of staple cartridge (850). In this intact state, barb (852) is configured to at least partially embed within tissue overlaid over staple deck (838), and thereby retain tissue relative to staple cartridge (850) and the corresponding stapler half. Additionally, in the pre-fired state of staple cartridge (850), a cutting member (860) of the firing assembly of the stapler is positioned proximal to barb (852). Cutting member (860) is similar to cutting member (164) described above in that cutting member (860) is coupled to a translating structure, such as a sled similar to sled (160), configured to translate longitudinally through longitudinal slot (846) and thereby cut tissue when the firing assembly is actuated.

As seen in FIG. 36B, as the firing assembly of the stapler is actuated distally, cutting member (860) translates distally through longitudinal slot (846) and severs upward tip (858) of cutaway barb (852), thereby separating barb halves (854, 856) from one another. Simultaneously, cutting member (860) cuts the tissue retained by barb (852). The separation of barb halves (854, 856) from one another facilitates release of the tissue by barb (852), so that the stapler may be more easily withdrawn from the tissue after firing.

F. Slidable Recessing Barb Coupled to Staple Cartridge

Figure 37A:
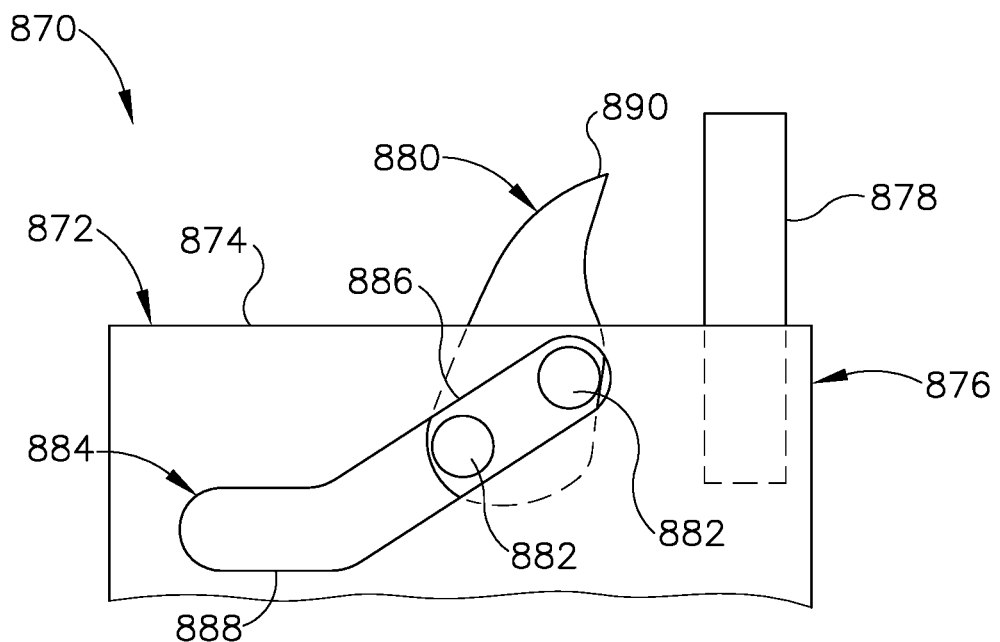
FIG. 37A depicts a schematic side elevational view of a portion of another exemplary staple cartridge having a tissue retaining feature, showing the tissue retaining feature in a first position in which the feature is configured to retain tissue.
Figure 37B:
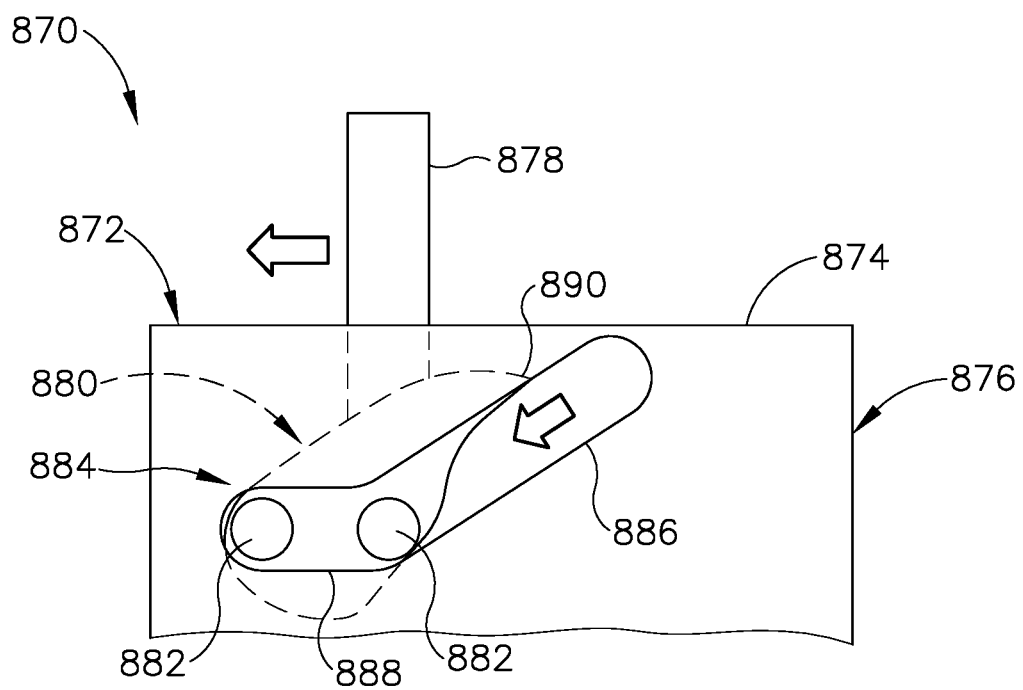
FIG. 37B depicts a schematic side elevational view of the staple cartridge of FIG. 37A, showing the tissue retaining feature in a second position in which the feature is configured to release tissue.

FIGS. 37A and 37B show another staple cartridge (870) having a tissue retaining feature of another exemplary configuration. Staple cartridge (870) is similar to staple cartridges (150, 800, 830) described above in that staple cartridge (870) includes, among other features, a cartridge body (872) having a staple deck (874) and a longitudinal slot (876) that slidably receives a translating member (878) of a stapler firing assembly. Staple cartridge (870) differs from staple cartridges (150, 800, 830) in that staple cartridge (870) includes a tissue retaining feature in the form of a slidable recessing barb (880) coupled to cartridge body (872).

Slidable recessing barb (880) includes a pair of laterally extending pins (882) that are slidable within a slot (884) formed in cartridge body (872). In the present example, slot (884) includes a proximal slot portion (886) that angles downwardly in a distal direction, and a distal slot portion (888) that extends generally parallel with a longitudinal axis of cartridge body (872). Barb (880) is movably received within a recess of cartridge body (872) that opens upwardly to staple deck (874) and communicates laterally with slot (884). Barb (880) is slidable between a proximal exposed position (FIG. 37A) in which an upward tip (890) of barb (880) is exposed upwardly beyond staple deck (874) for engaging and retaining tissue relative to staple cartridge (870), and a distal recessed position (FIG. 37B) in which barb (880) is recessed below staple deck (874) for releasing the tissue from staple cartridge (870). Slot (884) is configured to guide barb pins (882) from the proximal slot portion (886) to the distal slot portion (888) to thereby effect a transition of barb (880) from the exposed position to the recessed position.

Barb (880) is configured to slidably transition between the proximal exposed position (FIG. 37A) and the distal recessed position (FIG. 37B) in response to distal actuation of a firing assembly of the stapler in which staple cartridge in received. The firing assembly may be similar to firing assembly (200) described above, and includes a translating member (878) (shown schematically), which may be a sled structure similar to sled (160) described above. Translating member (878) translates distally through longitudinal slot (876) of staple cartridge (870) when the firing assembly is actuated. As shown in FIG. 37B, as translating member (878) advances distally through staple cartridge (870), translating member (878) contacts and drives barb (880) distally to its distal recessed position. This configuration enables the tissue to be released by barb (880) as the tissue is being cut and stapled. In the present example, barb (880) is configured to remain in the distal recessed position after staple cartridge (870) is fired. Though not shown, in some examples barb (880) may be returend proximally from the recessed position to the exposed position in response to proximal retraction of translating member (878) of the firing assembly.

While only one slidable recessing barb (880) is shown in the present example, it will be appreciated that staple cartridge (870) may include any suitable quantity of slidable recessing barbs (880), arranged at any suitable locations along a length of staple cartridge (870).

G. Pivotable Recessing Barb Coupled to Staple Cartridge

Figure 38A:
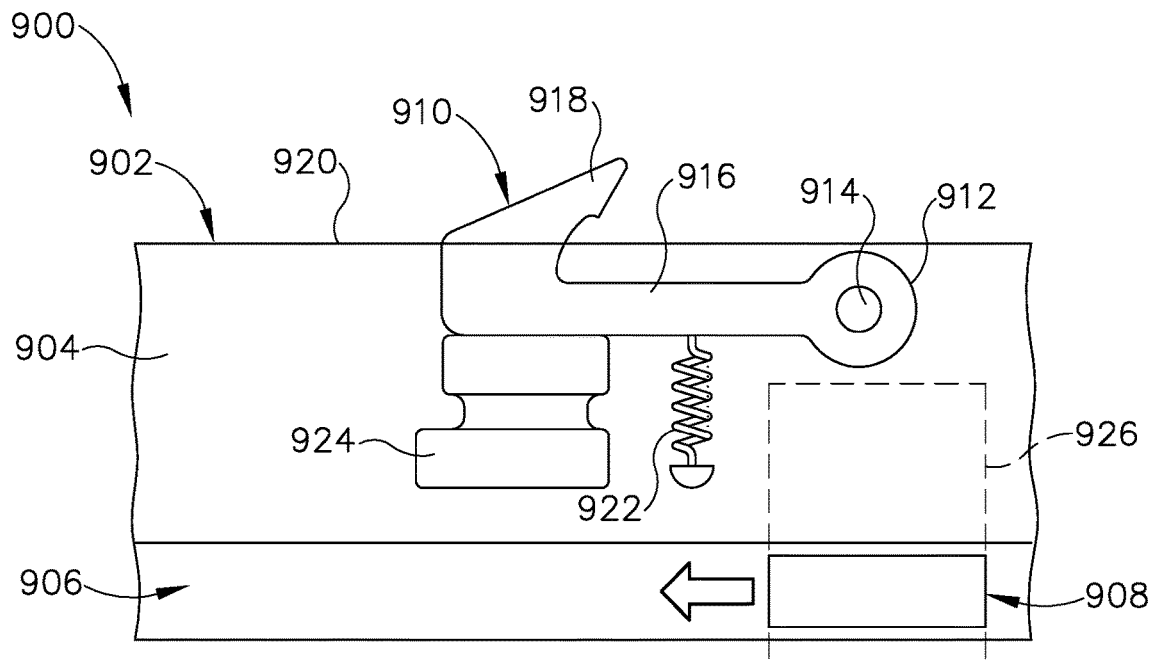
FIG. 38A depicts a schematic top elevational view of a portion of another exemplary staple cartridge having a tissue retaining feature, showing the tissue retaining feature in a first position in which the feature is configured to retain tissue.
Figure 38B:
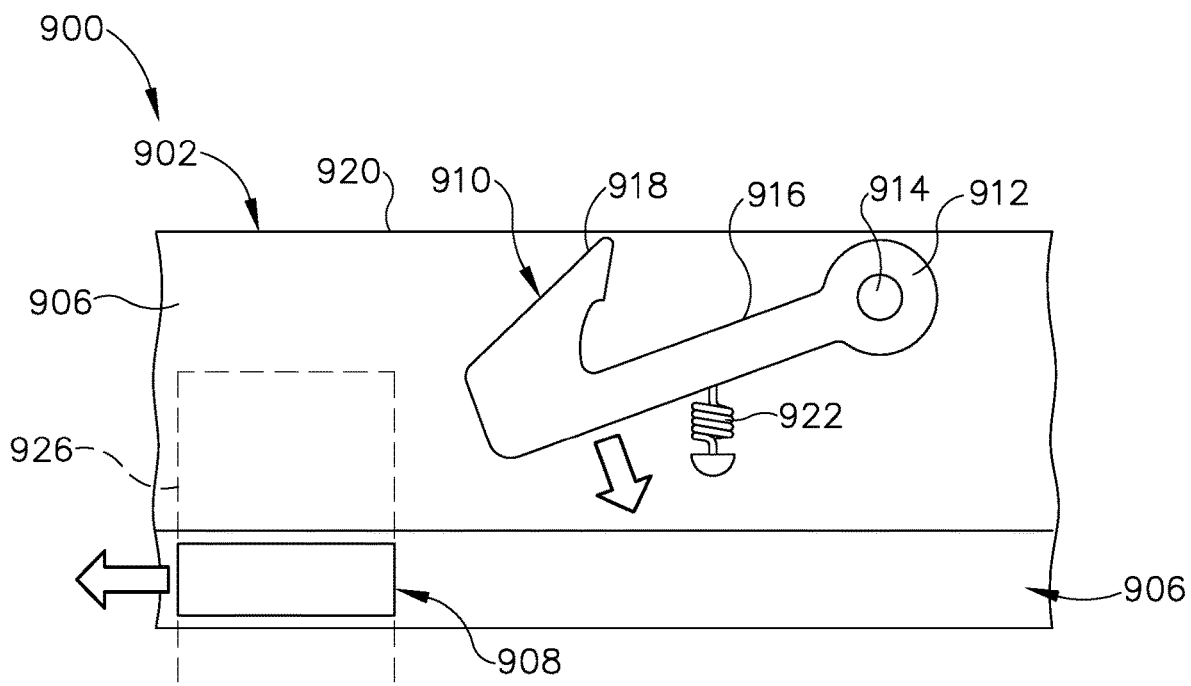
FIG. 38B depicts a schematic top elevational view of the staple cartridge of FIG. 38A, showing the tissue retaining feature in a second position in which the feature is configured to release tissue.

FIGS. 38A and 38B show another staple cartridge (900) having a tissue retaining feature of another exemplary configuration. Staple cartridge (900) is similar to staple cartridge (870) described above in that staple cartridge (900) includes, among other features, a cartridge body (902) having a staple deck (904) and a longitudinal slot (906) that slidably receives a translating member (908) (shown schematically) of a stapler firing assembly. Staple cartridge (900) differs from staple cartridge (870) in that staple cartridge (900) includes a tissue retaining feature in the form of a pivotable recessing barb (910) coupled to cartridge body (902).

Pivotable recessing barb (910) includes a pivot end (912) pivotably coupled to cartridge body (902) with a pivot pin (914), an arm (916) extending from pivot end (912), and a barb tip (918) that sweeps back toward pivot end (912) and is configured to engage and retain tissue. In the present example, barb (910) is orientable such that pivot end (912) is located proximally and barb tip (918) is located distally. It will be appreciated, however, that barb (910) may be oriented differently in alternative examples. Barb (910) is movably received within a recess formed within cartridge body (902) that opens to a lateral side (920) of cartridge body (902). Barb (910) is configured to pivot relative to cartridge body (902) between an exposed position (FIG. 38A) in which barb tip (918) is exposed laterally outward beyond lateral side (920), and a recessed position (FIG. 38B) in which barb tip (918) is fully recessed within cartridge body (902). In the present example, barb (910) is configured to pivot between the exposed and recessed positions about a pivot axis defined by pivot pin (914) that extends perpendicularly to a longitudinal axis of staple cartridge (900). In other examples, barb (910) may be configured to pivot about a vertically oriented pivot axis such that barb tip (918) extends through an opening formed in staple deck (904) when in the exposed position, for example.

Pivotable recessing barb (910) of the present example is biased toward the recessed position (FIG. 38B) by a resilient member shown in the form of an extension spring (922). A first end of spring (922) is coupled to barb (910), and a second end of spring (922) is anchored to cartridge body (902). As seen in FIG. 38A, showing staple cartridge (900) in a pre-fired state, a movable support structure shown in the form of a staple driver (924) is configured to hold barb (910) in the exposed position by overcoming the spring force exerted by extension spring (922) until the stapler is fired. Staple driver (924) may be similar in structure and function to staple drivers (168) described above. In other examples, the movable support structure may be provided separately from staple drivers (924) of staple cartridge (900), yet still configured to interact with the firing assembly of the stapler in which staple cartridge (900) in received.

FIG. 38A shows staple cartridge (900) in a first state in which pivotable recessing barb (910) is in the exposed position such that barb tip (918) is configured to engage and retain tissue relative to staple cartridge (900). As the stapler firing assembly is actuated distally, translating member (908) of the firing assembly advances distally through longitudinal slot (906) of staple cartridge (900). Translating member (908) is similar to sled (160) of firing assembly (200) described above in that translating member (908) includes a side portion (926) configured to contact and drive staple driver (924) upwardly through cartridge body (902) when the firing assembly is actuated distally. As shown in FIG. 38B, translating member (908) drives staple driver (924) upwardly toward staple deck (904) such that staple driver (924) disengages barb (910), thereby enabling extension spring (922) to draw barb (910) laterally inward into the recessed position. Upon reaching the recessed position, barb tip (918) releases the previously retained tissue from staple cartridge (900), such that the tissue is released while being simultaneously cut and stapled.

While only one pivotable recessing barb (910) is shown in the present example, it will be appreciated that staple cartridge (900) may include any suitable quantity of pivotable recessing barbs (910), arranged at any suitable locations along a length of staple cartridge (900).

V. Exemplary Combinations

The following examples relate to various non-exhaustive ways in which the teachings herein may be combined or applied. The following examples are not intended to restrict the coverage of any claims that may be presented at any time in this application or in subsequent filings of this application.

No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler, comprising: (a) an anvil half comprising: (i) an anvil channel member, (ii) an anvil surface having a plurality of staple forming pockets, and (iii) a projection coupled to a proximal portion of the anvil half; and (b) a cartridge half configured to releasably couple with the anvil half, wherein the cartridge half comprises: (i) a cartridge channel member having a distal portion configured to receive a staple cartridge, (ii) a latching lever pivotably coupled to the cartridge channel member, wherein the latching lever is pivotable between a closed position in which the latching lever engages and fixes the anvil channel member relative to the cartridge channel member, and an open position in which the latching lever disengages and permits movement of the anvil channel member relative to the cartridge channel member, and (iii) a locking member coupled to a proximal portion of the cartridge half, wherein the locking member is movable between a locked position in which the locking member captures the projection and thereby locks the proximal portion of the anvil half to the proximal portion of the cartridge half, and an unlocked position in which the locking member releases the projection and permits separation of the proximal portions, wherein the locking member is configured to assume the locked position when the latching lever is in the closed position, and the unlocked position when the latching lever is in the open position.

Example 2

The surgical stapler of Example 1, wherein the projection comprises a pin.

Example 3

The surgical stapler of any of the preceding Examples, wherein the locking member is configured to translate along a longitudinal axis of the cartridge channel member between the unlocked position and the locked position.

Example 4

The surgical stapler of any of the preceding Examples, wherein the locking member is positioned distally in the locked position and proximally in the unlocked position.

Example 5

The surgical stapler of any of the preceding Examples, wherein the locking member comprises a hook, wherein the hook is configured to capture the projection in the locked position.

Example 6

The surgical stapler of any of the preceding Examples, wherein the cartridge half further comprises a resilient member, wherein the resilient member is configured to bias the locking member toward the locked position.

Example 7

The surgical stapler of any of the preceding Examples, wherein the locking member is configured to move from the locked position to the unlocked position in response to movement of the latching lever from the closed position toward the open position.

Example 8

The surgical stapler of Example 7, wherein the locking member is operatively coupled to the latching lever by a movable structure, wherein the movable structure is configured to contact the latching lever and actuate the locking member in response to movement of latching lever.

Example 9

The surgical stapler of any of Example 8, wherein the movable structure is configured to translate along a longitudinal axis of the cartridge channel member

Example 10

The surgical stapler of any of Examples 8 through 9, wherein the movable structure comprises a follower member positioned to contact a proximally facing portion of the latching lever, wherein the follower member is configured to drive the movable structure proximally and thereby actuate the locking member to the unlocked position in response to pivoting of the latching lever from the closed position to the open position.

Example 11

The surgical stapler of Example 10, wherein the cartridge half further comprises a resilient member coupled to the movable structure, wherein the resilient member is configured to bias the movable structure distally so that the follower member contacts the proximally facing portion of the latching lever.

Example 12

The surgical stapler of any of Examples 10 through 11, wherein the proximally facing portion is coupled to a jaw of the latching lever, wherein the jaw is configured to capture a latch projection of the anvil channel member when the latching lever is in the closed position.

Example 13

The surgical stapler of any of the preceding Examples, wherein the locking member is coupled to a movable structure having a user-engageable portion, wherein the cartridge channel member includes an opening configured to provide access to the user-engageable portion when the latching lever is in the open position, wherein the locking member is movable to the unlocked position in response to manual actuation of the user-engageable portion by a user via the opening.

Example 14

The surgical stapler of Example 13, wherein the latching lever is configured to obstruct the opening when in the closed position.

Example 15

The surgical stapler of any of the preceding Examples, wherein the locking member includes a sloped upper surface.

Example 16

A surgical stapler, comprising: (a) an anvil half comprising: (i) an anvil channel member, and (ii) an anvil surface having a plurality of staple forming pockets; and (b) a cartridge half configured to releasably couple with the anvil half, wherein the cartridge half comprises: (i) a cartridge channel member having a distal portion configured to receive a staple cartridge, (ii) a latching member coupled to the cartridge channel member, wherein the latching member is movable between a closed position in which the latching member engages and fixes the anvil channel member relative to the cartridge channel member, and an open position in which the latching member disengages and permits movement of the anvil channel member relative to the cartridge channel member, and (iii) a locking member arranged at a proximal end of the cartridge half, wherein the locking member is configured to move from a locked position to an unlocked position in response to movement of the latching member from the closed position to the open position, wherein in the locked position the locking member is configured to lock a proximal end of the anvil half to the proximal end of the cartridge half, wherein in the unlocked position the locking member is configured to release the proximal end of the anvil half from the proximal end of the cartridge half.

Example 17

The surgical stapler of Example 16, wherein the latching member comprises a latching lever pivotably coupled to the cartridge channel member.

Example 18

The surgical stapler of any of Examples 16 through 17, wherein the locking member is operatively coupled to the latching member with an actuating member, wherein the actuating member is configured to translate and thereby actuate the locking member from the locked position to the unlocked position in response to movement of the latching member from the closed position to the open position.

Example 19

A surgical stapler, comprising: (a) an anvil half comprising: (i) an anvil channel member, and (ii) an anvil surface having a plurality of staple forming pockets, (b) a cartridge half configured to releasably couple with the anvil half, wherein the cartridge half comprises: (i) a cartridge channel member having a distal portion configured to receive a staple cartridge, and (ii) a latching member coupled to the cartridge channel member, wherein the latching member is movable between a closed position in which the latching member engages and fixes the anvil channel member relative to the cartridge channel member, and an open position in which the latching member disengages and permits movement of the anvil channel member relative to the cartridge channel member, and (c) a projection arranged at a proximal end of one of the anvil half or the cartridge half; and (d) a locking member arranged at a proximal end of the other of the anvil half or the cartridge half, wherein the locking member is movable from a locked position toward an unlocked position in response to movement of the latching member from the closed position toward the open position, wherein in the locked position the locking member is configured to engage the projection and thereby lock the proximal end of the anvil half to the proximal end of the cartridge half, wherein in the unlocked position the locking member is configured to disengage the projection and thereby release the proximal end of the anvil half from the proximal end of the cartridge half.

Example 20

The surgical stapler of Example 19, wherein the locking member is resiliently biased toward the locked position.

VI. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. App. Ser. No. 15/889,363, entitled "Release Mechanism for Linear Surgical Stapler," filed on Feb. 6, 2018, issued as U.S. Pat. No. 10,631,866 on Apr. 28, 2020; U.S. App. Ser. No. 15/889,370, entitled "Lockout Assembly for Linear Surgical Stapler," filed on Feb. 6, 2018, issued as U.S. Pat. No. 10,667,818 on Jun. 2, 2020; U.S. App. Ser. No. 15/889,374, entitled "Features to Align and Close Linear Surgical Stapler," filed on Feb. 6, 2018, published as U.S. Pub. No. 2019/0239886 on Aug. 8, 2019; U.S. App. Ser. No. 15/889,388, entitled "Firing Lever Assembly for Linear Surgical Stapler," filed on Feb. 6, 2018, published as U.S. Pub. No. 2019/0239884 on Aug. 8, 2019; and U.S. App. Ser. No. 15/889,390, entitled "Clamping Mechanism for Linear Surgical Stapler," filed on Feb. 6, 2018, issued as U.S. Pat. No. 10,687,819 on Jun. 23, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler, comprising:
   (a) a first stapler half comprising:
      (i) a first elongate member,
      (ii) an anvil surface having a plurality of staple forming pockets, and
      (iii) a projection coupled to a proximal portion of the first stapler half; and
   (b) a second stapler half configured to releasably couple with the first stapler half, wherein the second stapler half comprises:
      (i) a second elongate member having a distal portion configured to support a plurality of staples,
      (ii) a latching lever pivotably coupled to the second elongate member, wherein the latching lever is pivotable between a closed position in which the latching lever engages and fixes the first elongate member relative to the second elongate member, and an open position in which the latching lever disengages and permits movement of the first elongate member relative to the second elongate member, and
      (iii) a locking member coupled to a proximal portion of the second stapler half,
   wherein the locking member is longitudinally movable relative to the second elongate member between a locked position in which the locking member captures the projection and thereby locks the proximal portion of the first stapler half to the proximal portion of the second stapler half, and an unlocked position in which the locking member releases the projection and permits separation of the proximal portions.

2. The surgical stapler of claim 1, wherein the projection comprises a pin.

3. The surgical stapler of claim 1, wherein the locking member is configured to translate along a longitudinal axis of the second elongate member between the unlocked position and the locked position.

4. The surgical stapler of claim 3, wherein the locking member is positioned distally in the locked position and proximally in the unlocked position.

5. The surgical stapler of claim 1, wherein the locking member comprises a hook, wherein the hook is configured to capture the projection in the locked position.

6. The surgical stapler of claim 1, wherein the second stapler half further comprises a resilient member, wherein the resilient member is configured to bias the locking member toward the locked position.

7. The surgical stapler of claim 1, wherein the locking member is configured to move from the locked position to the unlocked position in response to movement of the latching lever from the closed position toward the open position.

8. The surgical stapler of claim 7, wherein the locking member is operatively coupled to the latching lever by a movable structure, wherein the movable structure is configured to contact the latching lever and actuate the locking member in response to movement of latching lever.

9. The surgical stapler of claim 8, wherein the movable structure is configured to translate along a longitudinal axis of the second elongate member.

10. The surgical stapler of claim 8, wherein the movable structure comprises a follower member positioned to contact a proximally facing portion of the latching lever, wherein the follower member is configured to drive the movable structure proximally and thereby actuate the locking member to the unlocked position in response to pivoting of the latching lever from the closed position to the open position.

11. The surgical stapler of claim 10, wherein the second stapler half further comprises a resilient member coupled to the movable structure, wherein the resilient member is configured to bias the movable structure distally so that the follower member contacts the proximally facing portion of the latching lever.

12. The surgical stapler of claim 10, wherein the proximally facing portion is coupled to a jaw of the latching lever, wherein the jaw is configured to capture a latch projection of the first elongate member when the latching lever is in the closed position.

13. The surgical stapler of claim 1, wherein the locking member is coupled to a movable structure having a user-engageable portion, wherein the second elongate member includes an opening configured to provide access to the user-engageable portion when the latching lever is in the open position, wherein the locking member is movable to the unlocked position in response to manual actuation of the user-engageable portion by a user via the opening.

14. The surgical stapler of claim 13, wherein the latching lever is configured to obstruct the opening when in the closed position.

15. The surgical stapler of claim 1, wherein the locking member is configured to assume the locked position when the latching lever is in the closed position, and the unlocked position when the latching lever is in the open position.

16. A surgical stapler, comprising:
 (a) an anvil half comprising:
  (i) an anvil channel member, and
  (ii) an anvil surface having a plurality of staple forming pockets; and
 (b) a cartridge half configured to releasably couple with the anvil half, wherein the cartridge half comprises:
  (i) a cartridge channel member having a distal portion configured to receive a staple cartridge,
  (ii) a latching member coupled to the cartridge channel member, wherein the latching member is movable between a closed position in which the latching member engages and fixes the anvil channel member relative to the cartridge channel member, and an open position in which the latching member disengages and permits movement of the anvil channel member relative to the cartridge channel member, and
  (iii) a locking member arranged at a proximal end of the cartridge half,
 wherein the locking member is configured to move from a locked position to an unlocked position in response to movement of the latching member from the closed position to the open position, wherein the locking member is resiliently biased toward the locked position, wherein in the locked position the locking member is configured to lock a proximal end of the anvil half to the proximal end of the cartridge half, wherein in the unlocked position the locking member is configured to release the proximal end of the anvil half from the proximal end of the cartridge half.

17. The surgical stapler of claim 16, wherein the latching member comprises a latching lever pivotably coupled to the cartridge channel member.

18. The surgical stapler of claim 16, wherein the locking member is operatively coupled to the latching member with an actuating member, wherein the actuating member is configured to translate and thereby actuate the locking member from the locked position to the unlocked position in response to movement of the latching member from the closed position to the open position.

19. A surgical stapler, comprising:
 (a) an anvil half comprising:
  (i) an anvil channel member, and
  (ii) an anvil surface having a plurality of staple forming pockets,
 (b) a cartridge half configured to releasably couple with the anvil half, wherein the cartridge half comprises:
  (i) a cartridge channel member having a distal portion configured to receive a staple cartridge, and
  (ii) a latching member coupled to the cartridge channel member, wherein the latching member is movable between a closed position in which the latching member engages and fixes the anvil channel member relative to the cartridge channel member, and an open position in which the latching member disengages and permits movement of the anvil channel member relative to the cartridge channel member, and
 (c) a projection arranged at a proximal end of one of the anvil half or the cartridge half; and
 (d) a locking member arranged at a proximal end of the other of the anvil half or the cartridge half, wherein the locking member is axially movable along a longitudinal axis of the one of the anvil half or the cartridge half from a locked position toward an unlocked position in response to movement of the latching member from the closed position toward the open position,
 wherein in the locked position the locking member is configured to engage the projection and thereby lock the proximal end of the anvil half to the proximal end of the cartridge half,
 wherein in the unlocked position the locking member is configured to disengage the projection and thereby release the proximal end of the anvil half from the proximal end of the cartridge half.

20. The surgical stapler of claim 19, wherein the locking member is resiliently biased toward the locked position.

* * * * *